US008603467B2

(12) United States Patent
Chen et al.

(10) Patent No.: US 8,603,467 B2
(45) Date of Patent: Dec. 10, 2013

(54) MONOCLONAL ANTIBODIES BINDING TO AVIAN INFLUENZA VIRUS SUBTYPE H5 HAEMAGGLUTININ AND USES THEREOF

(75) Inventors: Yixin Chen, Xiamen (CN); Wenxin Luo, Xiamen (CN); Jun Zhang, Xiamen (CN); Ningshao Xia, Xiamen (CN); Yi Guan, Xiamen (CN); Honglin Chen, Xiamen (CN)

(73) Assignees: Xiamen University, Fujiman Province (CN); Yang Sheng Tang Company, Haikou, Hainan (CN)

( * ) Notice: Subject to any disclaimer, the term of this patent is extended or adjusted under 35 U.S.C. 154(b) by 500 days.

(21) Appl. No.: 12/664,696

(22) PCT Filed: Jun. 16, 2008

(86) PCT No.: PCT/CN2008/001153

§ 371 (c)(1), (2), (4) Date: Jun. 21, 2010

(87) PCT Pub. No.: WO2008/154813

PCT Pub. Date: Dec. 24, 2008

(65) Prior Publication Data

US 2011/0311522 A1 Dec. 22, 2011

(30) Foreign Application Priority Data

Jun. 15, 2007 (CN) .......................... 2007 1 0111167

(51) Int. Cl.
*A61K 39/42* (2006.01)

(52) U.S. Cl.
USPC .................. 424/130.1; 424/133.1; 424/147.1; 530/350; 530/387.1; 530/387.3; 530/388.3; 435/5; 435/7.1; 435/339; 536/23.5

(58) Field of Classification Search
USPC ............. 530/350, 387.1, 387.3, 388.3; 435/5, 435/7.1, 339; 536/23.5; 424/130.1, 133.2, 424/147.1
See application file for complete search history.

(56) References Cited

FOREIGN PATENT DOCUMENTS

| | | | |
|---|---|---|---|
| CN | 1978634 | A | 6/2007 |
| CN | 1814623 | A | 8/2007 |
| CN | 101220097 | A | 7/2008 |
| WO | 2007/089753 | A2 | 8/2007 |

OTHER PUBLICATIONS

Rudikoff et al (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Winkler et al. (J. Immunol. Oct. 15, 2000; 165 (8): 4505-4514.*
Hanson et al.; "Passive immunoprophylaxis and therapy with humanized monoclonal antibody specific for influenza A H5 hemagglutinin in mice"; Respiratory Research; Oct. 14, 2006; vol. 7; No. 126.
Luo et al.; "Characterization of a broad spectrum neutralization monoclonal antibody against haemagglutinin of H5 subtype avian influenza virus"; Chinese Journal of Virology; Mar. 2007; pp. 85-90; vol. 23; No. 2; pp. 85-90.
He et al; "Detection of H5 Avian Influenza Viruses by Antigen-Capture Enzyme-Linked Immunosorbent Assay Using H5-Specific Monoclonal Antibody"; Clinical and Vaccine Immunology; May 2007; pp. 617-623; vol. 14; No. 5.
Fang et al.; "Preparation and Identification of a Single-chain Antibody Fragment Against High Pathogenic H5N1 Avian Influenza Virus", Chinese Journal of Biotechnology; Mar. 2007; pp. 292-296; vol. 23; No. 2.
Philpott et al.; "Neutralizing epitopes of the H5 hemagglutinin from a virulent avian influenza virus and their relationship to a pathogenicity"; Journal of Virology; Aug. 1989; pp. 3453-3458; vol. 63; No. 8.
Huang et al.; "Different neutralization efficiency of neutralizing monoclonal antibodies against avian influenza H5N1 virus to virus strains from different hosts"; Molecular Immunology; Feb. 1, 2007; vol. 44; No. 5.
Smirnov et al.; "Prevention and treatment of bronchopneumonia in mice caused by mouse-adapted variant of avian H5N2 influenza A virus using monoclonal antibody against conserved epitope in the HA stem region"; Archives of Virology; 2000; pp. 1733-1741; vol. 145; No. 8.
Hinshaw et al.; "Specific Antibody Responses and Generation of Antigenic Variants in Chickens Immunized Against a Virulent Avian Influenza Virus"; Avian Diseases; 1990; pp. 80-86; vol. 34; No. 1.
Chen et al.; "A latex agglutination test for the rapid detection of avian influenza virus subtype H%N1 and its clinical application"; Journal of Veterinary Diagnostic Investigation; 2007; pp. 155-160; vol. 19.
Kaverin et al.; "Structure of antigenic sites on the haemagglutinin molecule of H5 avian influenza virus and pheotypic variation of escape mutants"; Journal of General Virology; 2002; pp. 2497-2505; vol. 83.

(Continued)

*Primary Examiner* — Stephen Rawlings
(74) *Attorney, Agent, or Firm* — Banner and Witcoff, Ltd

(57) ABSTRACT

The present invention provides monoclonal antibodies that bind specifically to H5 subtype avian influenza virus hemagglutinin (HA) proteins, and can block the binding activity of at least 50% of the known monoclonal antibodies to the H5 subtype avian influenza virus hemagglutinin (HA) protein. The monoclonal antibodies can be used for the detection, diagnosis, prevention, and treatment of avian influenza viruses, especially the H5 subtype of avian influenza viruses. The present invention also provides the related hybridoma cell lines, isolated nucleic acid molecules and short peptides, as well as medical composition and medical diagnostic equipment and kit containing the monoclonal antibody.

21 Claims, 5 Drawing Sheets

(56) References Cited

OTHER PUBLICATIONS

Cleveland et al.; "Selection of neutralizing antibody escape mutants with type A influenza virus HA-specific polyclonal anti sera: possible significance for antigenic drift"; Epidemiology and Infection; 1997; pp. 149-154; vol. 118; No. 2.

Qin, A.J. et al. "Development and application of monoclonal antibodies specific to hemagglutinin of subtype H5 and H9 avian influenza virus." Chinese Journal of Preventive Veterinary Medicine. May 2003, vol. 25, No. 3, pp. 161-163 ISSN 1008-0589.

Tapryal et al.; "Anti-rhGM-CSF heavy chain variable domain Feb. 7, 2006"; GenBank [online]; [retrieved on Sep. 9, 2008]. Retrieved from: NCBI, Bethesda, USA. GenBank accession No. ABC94918.

Office Action issued in related European Application No. 08772961.2, dated Dec. 17, 2012.

Cao, Zhen, et al, "Preparation and Characterization of Monoclonal Antibody Specific to Hemagglutinin of Subtype H5 Avian Influenza Virus," Acta Laboratorium Animalis Scientia Sinica, Dec. 2004, vol. 12, No. 4, pp. 197-199. (with English language abstract).

* cited by examiner

FIG. 1
EcoR I
Xba I
Pcmv
8G9 VK
Human CL
f1 ori
pcDNA3.1- Ak8G9
6091 bp
SV40 ori
Amp
Neo
pMB1
SV40 pA
BamH I
Pcmv
8G9 VH
Human CH
Xba I
pcDNA3.1- AH8G9
6972 bp
f1 ori
Amp
SV40 ori
Hyg
pMB1
SV40 pA
EcoR I
Xba I
Pcmv
13D4 VK
Human CL
f1 ori
pcDNA3.1-Ak13D4
6082bp
SV40 ori
Amp
Neo
pMB1
SV40 pA
BamH I
Pcmv
13D4 VH
Human CH
Xba I
pcDNA3.1-AH13D4SV
6981 bp
f1 ori
Amp
SV40 ori
Hyg
pMB1
SV40 pA
BamH I
Pcmv
13D4 VH
Human CH
Xba I
pcDNA3.1-AH13D4LV
6981 bp
f1 ori
Amp
SV40 ori
Hyg
pMB1
SV40 pA

MONOCLONAL ANTIBODIES BINDING TO AVIAN INFLUENZA VIRUS SUBTYPE H5 HAEMAGGLUTININ AND USES THEREOF

FIELD OF THE INVENTION

The present invention relates to monoclonal antibodies specifically binding to avian influenza virus subtype H5 hemagglutinin (HA) and the conservative variant or active fragment thereof, or the related coding sequence of polypeptide or polypeptide analog, or cell lines producing such monoclonal antibodies, and methods of using the antibodies and fragments thereof for purposes of diagnosis, prevention and treatment.

BACKGROUND OF THE INVENTION

Research indicates that the H5N1 avian influenza virus that infected human in Hong Kong in 1997 has 8 gene fragments, all derived from Eurasian avian influenza and has the capacity of binding the receptor of $\alpha(2,3)$ saliva acid, showing the typical characters of avian influenza viruses (Matrosovich, M. et al., J Virol, 1999, 73(2):1146-55). And the H5N1 avian influenza viruses of 1997 were cleared away after slaughtering all the poultry in Hong Kong. However, the virus A/goose/Guangdong/1/96(H5N1) from which the H5N1 in 1997 is derived was prevalent successively in the southeast of China (Cauthen, A. N. et al., J. Virol., 2000, 74(14):6592-9; Webster, R. G. et al., J. Virol., 2002, 76(1):118-26), and soon the virus was substituted by different kinds of genotypes (Guan, Y. et al., Proc Natl Acad Sci USA, 2002, 99(13):8950-5) which were lethal for chicken but not for duck. And these H5N1 viruses were cleared away again by slaughtering all the poultry until substituting viruses of new genotypes came up in 2002. Between 1997 and 2001, HA of these virus strains of different genotypes have similar immunogenicity. But obvious antigen drift occurred in 2002 (Guan, Y. et al., Proc Natl Acad Sci USA, 2004, 101(21): 8156-61; Sturm-Ramirez, K. M. et al., J. Virol., 2004, 78(9): 4892-901). It is rare that the typical character of the H5N1 virus of late 2002 is resulting in high mortality for duck and other waterfowl. Death of large number of waterfowl happened last time in 1961 when lots of terns died because of A/tern/South Africa/61(H5N3).

In early February of 2003, a family of Hong Kong was infected by H5N1 virus (Peiris, J S et al., Lancet, 2004, 363 (9409):617-9). The daughter of the family died of respiratory tract infection of unknown reason during her visit to Fujian, the father and the son had acute respiratory illness after returning to Hong Kong. Eventually the father died but the son recovered from the disease. Both the father and the son have been diagnosed as infected by the H5N1 influenza viruses that are highly similar in antigenecity and molecular level with the viruses which are highly lethal for chicken and duck after antigen drifting. (Guan, Y. et al., Proc Natl Acad Sci USA, 2004, 101 (21):8156-61).

Unprecedented large-scale avian influenza occurred in Asia in 2004 including the H5N1 appeared in China, Japan, Korea, Thailand, Vietnam, Indonesia, Cambodia and Laos, the H7N3 in Pakistan, and the H5N2 in Taiwan. A large number of poultry especially chicken were slaughtered because of the pandemic infection of avian influenza. Up to now, cases of human infection of avian influenza appeared in those countries where large-scale epidemic spread happened, and many of those infected died. These H5N1 viruses were first found in dead migratory waterfowl including egrets, gray herons and Canada geese in Hong Kong in November 2002. After analyzing the viruses obtained from the dead birds, it was found that comparing to the previous virus in Hong Kong, the antigenecity of these viruses has severely changed and these viruses have got the capacity of causing the death of large number of infected duck. (Sturm-Ramirez, K. M. et al., J. Virol., 2004, 78(9): 4892-901). The unusual aspect of this event is that all the high pathogenic H5N1 viruses were isolated from the migratory birds flying to Hong Kong in the winter of 2002-2003. And at that time some people predicted that the migratory birds will spread the virus after they fly back in summer (Sturm-Ramirez, K. M. et al., J. Virol., 2004, 78(9): 4892-901). This was true, large number of migratory birds were infected with H5N1 in Qinghai Lake, and according to research, all the present H5N1 viruses in Europe and Africa were brought from Asia by migratory birds.

Genetically, the pandemic H5N1 virus in Asia in 2004 was very similar to the Z-genotype of the virus that appeared in Hong Kong in 2003 and became the mainly spreading virus. At this time the Asia pandemic virus was very similar to A/Vietnam/1203/04(H5N1) in antigenic and genetic level and have all 8 gene fragments derived from Eurasian avian influenza. In both Vietnam and Thailand, cases of human infected by virus of this genotype appeared.

The pandemic H5N1 viruses have the potential of successfully transmitting to mammals. Because of successive evolution and the tendency of recombination, a variety of different genotypes of H5N1 viruses were produced, antigenic drift of the HA of H5N1 viruses occurred and the viruses have already had high pathogenic capacity for waterfowl.

The WHO (World Health Organization, WHO) statistics shows that currently Asia, Africa, Europe and North America all have reported poultry infected with highly pathogenic avian influenza virus [Organization, WH, H5N1 avian influenza: Timeline of major events. 2007]. From 2003 to Apr. 2, 2007, in 12 countries located in East Asia, Southeast Asia, Middle East, Africa and Europe infected cases of human infection with H5N1 virus were confirmed by laboratory diagnose, the total number of infected people is 288 and 170 of them died [Organization, W.H., Cumulative Number of Confirmed Human Cases of Avian Influenza A/(H5N1) Reported to WHO. 2007]. The epidemic spreading tendency did not cease, raising the entire world's attention.

Combining with the spread of H5N1 in recent years, its outbreak in poultry, its transmission to various mammals, its infection of human and its possible spread in mammals (Thanawongnuwech, R. et al., Emerg Infect Dis, 2005, 11 (5):699-701; Ungchusak, K. et al., N Engl J Med, 2005, 352 (4):333-40), large-scale outbreak of H5N1 viruses in humans is only a matter of time (Hien, T. T. et al., N Engl J Med, 2004, 351 (23):2363-5; Stohr, K. et al., N Engl J Med, 2005, 352 (4): 405-7).

The first line of preventing the flu is neutralizing antibody, and the most effective antibody is produced by HA, so influenza H5N1 vaccine can be developed based on HA protein. However, the vaccine need to constantly "upgrade" in order to catch up with the pace of virus mutation, because the HA gene has high variability and antigenic drift can make the vaccine ineffective. In order to overcome it, each year, WHO needs to select new vaccine strains as vaccines for next year's epidemic season according to the monitoring result of the mutation of previous year's epidemic virus strains, and new vaccine needs to be injected each year to ensure the maintenance of effective protection against current epidemic virus strain. Large amount of traditional influenza vaccines were produced by chicken embryo culture method or cell culture method, they mainly are inactivated whole-virus vaccines, lytic vaccines or subunit vaccines. These traditional influenza vaccines continue to occupy the current market, but their immunogenicity, safety, and side effects are still not credible. Because H5N1 viruses have high toxicity to the chicken embryo, the original limited production capacity of vaccine manufacturers can't meet the requirements of the market at the global outbreak state. And the application of different kinds of live attenuated influenza vaccines was limited because of safety problems and side effects (Horimoto T. et al., Trends in Molecular medicine, 2006, 12(11):506-514). With the development of science and technology, using the new molecular biology technique to study new influenza vaccines has become a new trend of the present research of influenza vaccines, such as nucleic acid vaccine, genetically engineered vaccine, epitope vaccine.

At present, after long-term usage, two kinds of drugs have been confirmed to be able to treat influenza effectively, they are divided into two types: M2 ion channel inhibitors such as amantadine (amantadine) and rimantadine (rimantadine), and neuraminidase inhibitors such as oseltamivir (oseltamivir) and zanamivir (zanamivir) (Monto, A S Vaccine, 2003. 21 (16): 1796-800). The first two ones showed their anti-viral effects by suppressing the virus M2 ion channel protein, and the latter two can selectively inhibit the activity of neuraminidase on the virus surface, prevent the replication and release of progeny virus in host cells, prevent cold and alleviate the symptoms effectively. So, neuraminidase inhibitors are the relatively effective anti-influenza drugs. However, resistance to neuraminidase inhibitors in H5N1 have been continually discovered. And if taken within the first 2 days, it can shorten the course of diseases, even save the life of the patient. Although ion-channel inhibitors are very useful for some subtypes of influenza viruses (Dolin, R. et al., *N Engl J Med,* 1982. 307(10):580-4), it also causes serious side-effect, and thus, resistant strains appear soon (Shiraishi, K. et al., *J Infect Dis,* 2003, 188(1):57-61). And the resistant strains haven't shown weakened transmitting ability and pathogenicity. By now, resistance of ion-channel inhibitors appeared broadly over the world (Bright, R. A. et al., Lancet, 2005, 366(9492): 1175-81), so ion-channel inhibitors were opposed for being used as therapeutic and preventive drugs against influenza by CDC of the United State in the 2005-2006 influenza season. However, considering many advantage of ion-channel inhibitors, it should be used for further treatment, but in combination with other drugs. The dosage shall be reduced as well as side-effect, and meanwhile, the risk of drug resistance shall be reduced (Tsiodras, S. et al., Bmj, 2007, 334 (7588):293-4). In 2005, Oseltamivir-resistant H5N1 virus strain was reported (Le, Q. M. et al., Nature, 2005, 437:1108; de Jong, M. D. et al., *Engl J Med.,* 2005, 353:2667-2672).

Some infected and recovered patients of H5N1 have antibodies able to neutralize viruses in iv-vitro assay, which indicates that antibody may be one of the methods used for treating influenza virus infection (de Jong, M. D. et al., Nat. Med., 2006, 12: 1203-1207). Clinically, polyclonal and monoclonal antibodies are effectively used for preventing HAV, HBV, rabies and RSV infection (Sawyer, L. A., Antiviral Res., 2000, 47:57-77). During the 1918 spa-influenza, mortality was reduced by 50% by treatment using convalescent serum of human (Luke, T. C. et al., Ann Intern Med., 2006, 145:599-609). In China, the successful treatment experience of SARS and H5N1 patients also show that, patient convalescent serum could inhibit viral in-vivo replication effectively, so that dying patients could recover. In mouse models, H5N1 specific humanized mouse monoclonal antibodies, entirely humanized monoclonal antibodies and F(ab')2 fragment have been proved to have efficacy for the prevention and treatment of H5N1 infection (Lu, J. et al., Respir Res., 2006, 7:43; Simmons, C. P. et al., PLOS Medicine, 2007, 4(5):928-936; Hanson, B. J. et al., Respir Res., 2006, 7:126). The persistent antigen mutation of highly pathogenic avian influenza H5N1 at receptor-binding site, namely antigenic drift, challenges the broad-spectrum anti-virus treatment ability of these antibodies. Thus, obtaining monoclonal antibodies with broad-spectrum neutralization ability becomes the hope for H5N1 treatment, and the use of high quality anti-H5N1 broad-spectrum neutralization monoclonal antibodies to treat H5N1 patients may inhibit in vivo replication of H5N1 virus and obtain ideal treatment effects. This is a brand new way of anti-virus treatment.

Furthermore, the study of molecular epidemiology shows that, about 30% of positively infected ducks do not have any symptom, 10% of the epidemic virus carrying chickens show no symptom. These infected animals can continually cause new infections for human, which causes huge threat to human health. All the related experts regard that, the spread of the H5 type highly pathogenic avian influenza virus in the entire eastern Asia, southeastern Asia and Europe shall be well controlled. Early phase diagnosis is the precondition, and then early quarantine, early handling can be done and human should be treated early.

It takes 4-5 days to diagnose avian influenza virus with traditional viral separation and serum diagnosis method, besides, the majority human and animal disease control system labs lack $3^{rd}$ level biosafety lab, so the diagnose of H5 outbreak in southeastern Asia countries and regions is apparently lagging. The common situation is that there is still no diagnose report from labs after the death of large number of chickens and the completion of slaughtering, which causes great inconvenience for the control of virus outbreak. In addition, because a minority of poultry (especially waterfowl, such as domestic ducks) reveals no symptom of virus infection, and there is no effective testing means in the quarantine system, the above situation continues to develop, giving rise to repetitive outbreak of the virus in many countries and regions.

Meanwhile, since H5 avian influenza virus (among which, Goose/Guangdong/1/96 is the representative strain) belongs to highly pathogenic virus, it is fatal for the presently commonly used animal models, and the antigenicity of hemagglutinin protein (HA) expressed by genetic engineering method can't be completely obtained. Many of the world's famous laboratories have successively attempted to prepare monoclonal antibody against the virus series but they all failed. At present the virus antigenicity analysis has to use the monoclonal antibody prepared with A/chicken/Pennsylvania/1370/83(H5N2) and A/chicken/Pennsylvania/8125/83 (H5N2), whose specificity and reactivity obviously cannot meet the requirements of diagnostic reagent.

Because of the above situation, at present, a method for convenient, fast, and real time diagnosis is urgently required. Thus patients of the first cross-species infected generation can be isolated and treated, preventing the virus infection among human, and the transmission chain can be interrupted before the virus has adapted to human beings, so that the threat of human-wide influenza of the virus can be fundamentally eliminated.

Within China, studies on the detection of subtype H5 avian influenza virus have been reported in the literature. Qin Aijian et al. from College of Animal Husbandry and Veterinary Medicine, Yangzhou University (Qin Aijian, Shao Hongxia, Qian Xian et al., Journal of Chinese Prevention Veterinary Medicine 2003, No. 3) prepared hemagglutinin specific monoclonal antibodies against avian influenza viruses subtype H5 and subtype H9, and it was confirmed that with these monoclonal antibodies, the corresponding avian influenza virus can be quickly detected within 24 hours by indirect immunofluorescence assay. The detection time for the highly pathogenic subtype H5 of avian influenza virus was shortened to 4 hours, which was achieved by the Beijing Office for Entry-Exit Inspection and Quarantine with a rapid fluorescent RT-PCR. It was clinically confirmed on 10 Dec. 2005. Guo Yuanji reviewed in his paper with the title "Present Situation of Human Avian Influenza Research" that micro-neutralization experiment or ELISA with high specificity was needed for detecting the antibody against virus strain of subtype H5 (Guo Yuanji, Chinese Journal of Experimental and Clinical Virology, 2004, No. 3). But there is no research report on the detection of subtype H5 by ELISA There have been research reports abroad on detection of H5N1 antibody using ELISA. Rowe et al. reported that using recombinant hemagglutinin protein as antigen envelope to detect H5N1 antibody indirectly by ELISA, the sensitivity of ELISA is 80%, and specificity is 62% (Rowe T, et al., *J Clin Microbiol.* April 1999; 37 (4): 937-43). But this literature is not directed to monoclonal antibody specific for hemagglutinin HA gene of subtype H5N1. Zhou et al. (Zhou E M et al., Avian Dis. 1998, 42 (4): 757-61) and Shafer et al. (Shafer, A L et al., Avian Dis. 1998, 42 (1): 28-34) detected avian influenza virus anti-core-protein antibody using competitive ELISA, but the detection subjects were all antibodies for NP proteins of all the subtypes H1-H16 of type A avian influenza, and the subtype couldn't be determined Lu reported a method for detecting avian influenza virus (AIV) by Dot-ELISA based on monoclonal antibody., This method detected AIV antigen directly and its specificity is that it has no cross-reaction with other avian viruses (Lu H. Avian Dis. 2003 47 (2): 361-9). Although Sala et al. established ELISA based on monoclonal antibody specific for surface glycoprotein of subtype H7, but the subtype was H7, and the monoclonal antibody was specific to surface glycoprotein (Sala G, Cordioli P, Moreno-Martin et al., Avian Dis. 2003, 47 (3 Suppl): 1057-9), rather than specific to hemagglutinin HA gene of subtype H5.

It is regretful that most of the monoclonal antibodies used in current immunology diagnosis of avian influenza virus are against core protein (NP protein), thus used for detecting influenza virus of type A. But type A influenza virus actually includes subtypes H1-H16 with 16 subtypes in total, among which most subtypes have no pathogenicity or only low pathogenicity while only subtype H5 of avian influenza virus is the most harmful avian influenza virus with high pathogenicity. Thus the available technologies are far from meeting the demands of clinic detections.

The ultimate aim of the present invention is to overcome the defects of present immune detection, treatment and prevention of AIV, the monoclonal antibody used is against hemagglutinin (HA) protein of H5 subtype. In mouse models, this monoclonal antibody can effectively treat infections of many types of H5N1 virus mutation strains, it can also be used to specifically detect highly pathogenic H5 subtype avian influenza virus and for the production of vaccine and other therapeutic drug against H5N1.

SUMMARY OF THE INVENTION

The present invention provides monoclonal antibodies specifically binding to hemagglutinin (HA) protein of H5 avian influenza viruses, and monoclonal antibodies which can block the binding activity of at least 50% of the monoclonal antibodies binding to hemagglutinin (HA) protein of H5 avian influenza viruses. The present invention also provide related hybridoma cell lines, isolated nucleic acid molecules and short peptides, as well as drug combination and medicine diagnostic instrument and kit containing such monoclonal antibodies. The present invention also provides methods using these monoclonal antibodies for the detection, diagnosis, prevention and treatment of avian influenza viruses, especially H5 subtype avian influenza viruses.

A: results of reactions of G1, G2, G3, G4, G5 phage peptide with multiple monoclonal antibodies;

B: results of reactions of G10 phage peptide with multiple monoclonal antibodies.

Figure 4:
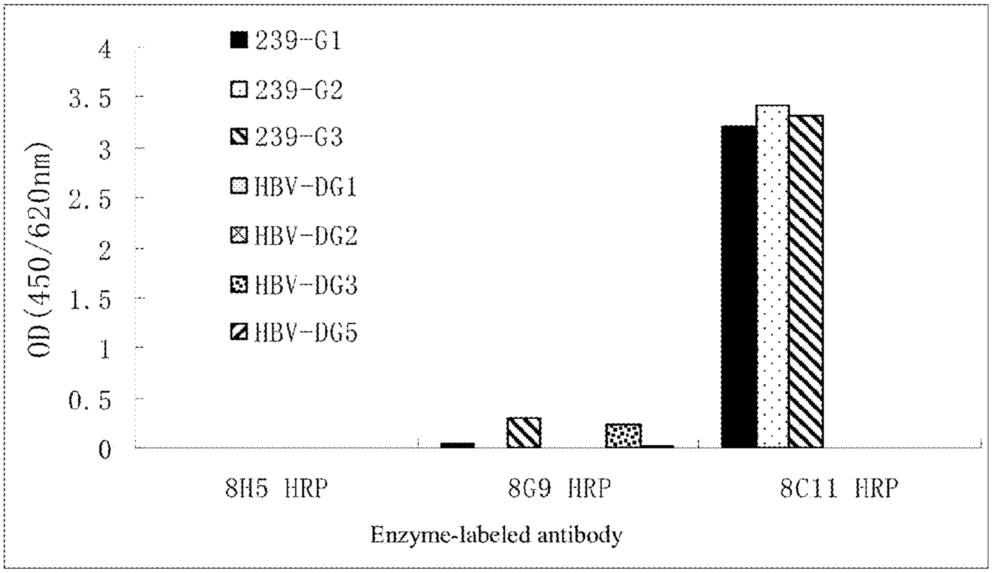

FIG. 4 shows the reactivity of fusion proteins 239-G1, 239-G2, 239-G3, 239-G5 and HBc-DG1, HBc-DG2, HBc-DG3, HBc-DG5 with enzyme-labeled antibody 8G9-HRP.

Figure 5:
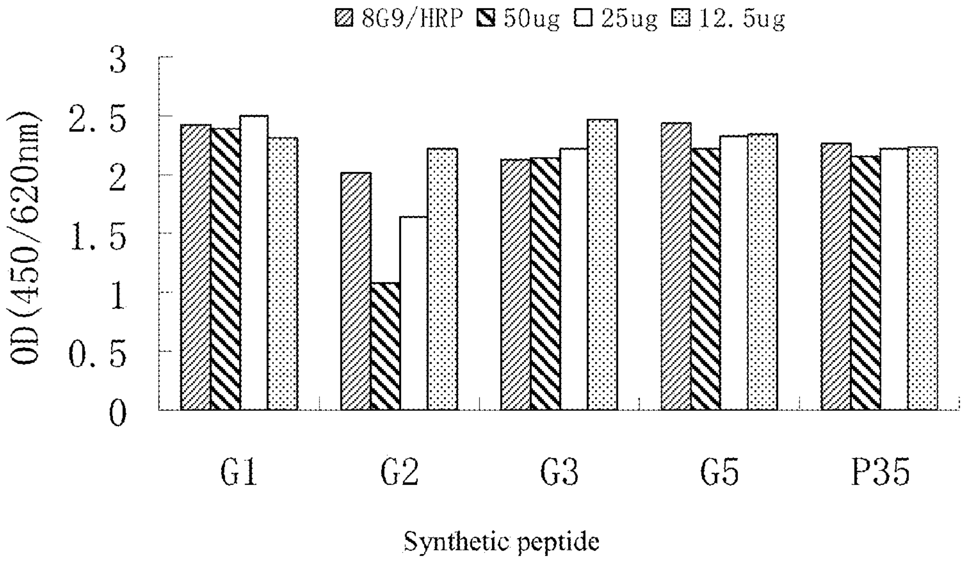
Figure 6:
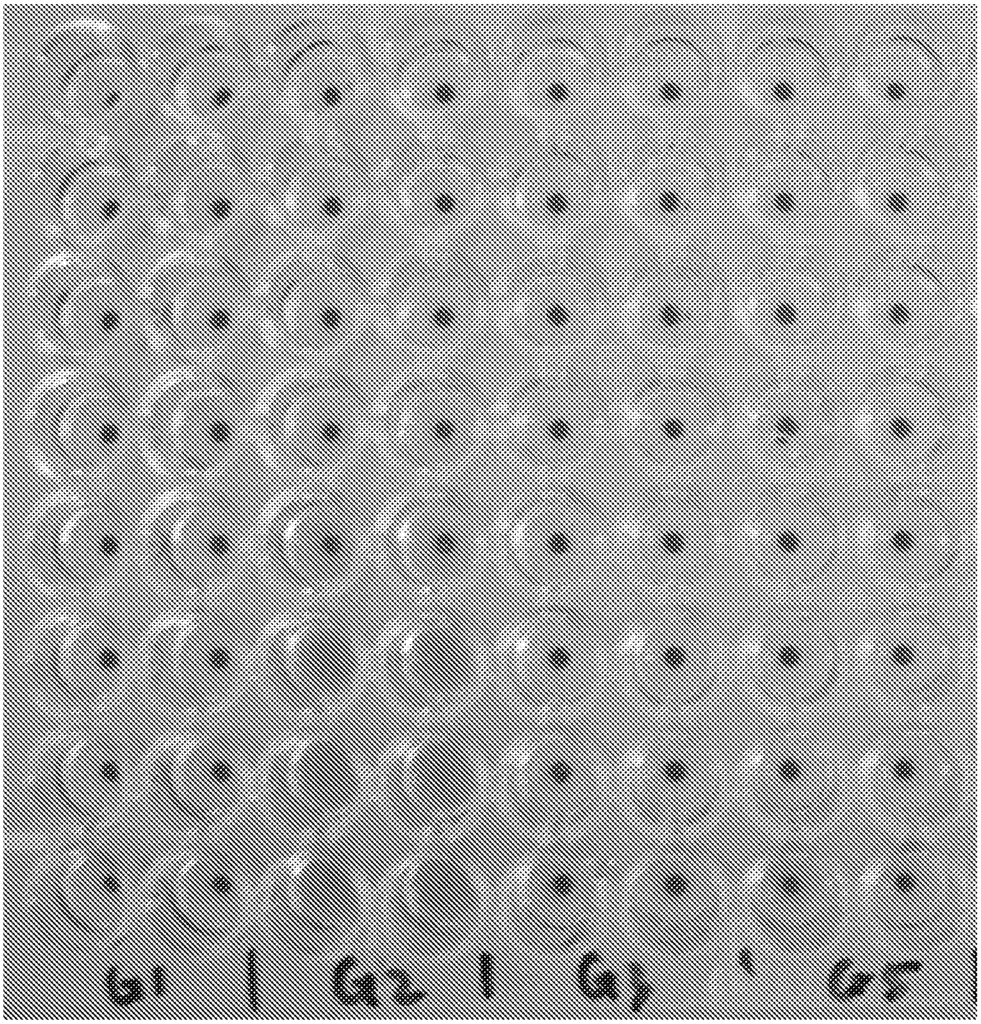

FIG. 5 shows the competitive ELISA detection result of synthesized peptides and avian influenza virus FIG. 6 shows the result of blocking hemagglutinin inhibition (HI) experiment of the synthesized peptides G1, G2, G3, and G5.

DETAILED DESCRIPTION OF THE INVENTION

Definitions of relevant terms related to the present invention are as follow:

The term "hemagglutinin" of the present invention refers to an envelope glycoprotein of the avian influenza virus. Hemagglutinins mediate adsorption and penetration of the influenza virus needle into a host cell. Avian influenza virus hemagglutinin proteins have sixteen different serological subtypes, HA1 to HA16, corresponding to the sixteen viral subtypes H1-H16 respectively.

The term "antibody" of the present invention refers to any immunoglobulin, including monoclonal antibodies, polyclonal antibodies, bispecific or multispecific antibodies able to bind to a specific antigen. A complete antibody comprises two heavy chains and two light chains. Each heavy chain consists of a variable region and a first, second, and third constant region, while each light chain consists of a variable region and a constant region. The antibody has a "Y" shape, with the stem of the "Y" consisting of the second and third constant regions of the two heavy chains bound together via disulfide bonding. Each arm of the "Y" consists of the variable region and the first constant region of one of the heavy chains and the variable and constant regions of a light chain. The variable regions of the light and heavy chains determine antigen binding. The variable region of each chain contains three highly variable regions called complementarity determining regions (CDR) (light (L) chain CDRs include LCDR1, LCDR2, and LCDR3, heavy (H) chain CDRs include HCDR1, HCDR2, HCDR3) (they are defined by Kabat, et al., see Sequences of Proteins of Immunological Interest, Fifth Edition (1991), vols. 1-3, NIH Publication 91-3242, Bethesda Md.). Among them, the three CDRs are separated by framework regions (FR), which are more conservative than the CDRs and form a frame structure to support the hypervariable region. The constant regions of the heavy and light chains are irrelevant for antigen binding, but have various effector functions. Antibodies are assigned to different classes based on the amino acid sequence of the constant region of their heavy chains. The major classes of antibodies are IgA, IgD, IgE, IgG, and IgM, with several of these classes divided into subclasses such as IgG1, IgG2, IgG3, IgG4, IgA1, or IgA2.

In addition to an intact immunoglobulin, the term "antibody" of the present invention further refers to an immunoglobulin fragment thereof (i.e., at least one immunologically active fragment of an immunoglobulin molecule), such as a Fab, Fab', F(ab')2, Fv fragment, a single-chain antibody molecule, a multispecific antibody formed from any fragment of an immunoglobulin molecule comprising one or more CDRs. In addition, an antibody related to the present invention may also comprise one or more CDRs from a particular human immunoglobulin grafted to a framework region from one or more different human immunoglobulins.

"Fab" fragment with regard to an antibody refers to part of the antibody molecule comprising the variable and constant regions of a light chain and the variable and constant regions of a heavy chain, which are bound by a disulfide bond.

"Fab" fragment refers to a Fab fragment that contains part of the hinge region.

"F(ab')2 refers to a dimer of Fab'.

"Fc" of an antibody refers to that portion of the antibody consisting of the second and third constant regions of a first heavy chain bound to the second and third constant regions of a second heavy chain via disulfide bonding. The Fc portion of the antibody has multiple different functions but is not involved in antigen binding.

"Fv" of an antibody refers to the smallest fragment of the antibody able to bind the t complete antigen binding site. A Fv fragment consists of the variable region of a light chain bound to the variable region of a heavy chain.

"Single-chain antibody" or "scFv" of the present invention refers to an engineered antibody consisting of a light chain variable region and a heavy chain variable region connected to one another directly or via a peptide linker. (Houston 1988).

"Single-chain antibody Fv-Fc" or "scFv-Fc" of the present invention also includes an engineered antibody consisting of a scFv connected to the Fc region of an antibody.

"Antigenic determinant" (or called as epitope) of the present invention refers to the atom group or amino acid of an antigen molecule to which an antibody binds.

The term "monoclonal antibody" of the present invention refers to an antibody or a fragment thereof obtained from a population of highly homogeneous antibodies, i.e., a group of identical antibodies except for possible natural mutations that may occur in rare cases. Monoclonal antibodies are highly specific for a single epitope on the antigen. Monoclonal antibodies are different from polyclonal antibodies, which comprise antibody molecules recognizing different epitopes on the surface of an antigen. Although traditional monoclonal antibodies are secreted by hybridomas, the monoclonal antibodies of the present invention are not limited to this production method. For example, the monoclonal antibodies of the present invention may be obtained by the hybridoma technique first reported by Kohler et al., (Nature, 256:495 1975), or may be obtained by recombinant DNA technique (see, e.g., U.S. Pat. No. 4,816,567).

The term "chimeric antibody" of the present invention refers to an antibody in which part of the heavy and/or light chain is identical with or homologous to corresponding sequences in antibodies derived from a particular species or belonging to a particular antibody class or subclass, while the other part of the heavy and/or light chain is identical with or homologous to corresponding sequences in antibodies derived from another species or belonging to another antibody class or subclass., In any case, such fragments still preserve the binding activity to target antigen. (U.S. Pat. No. 4,816,567 of Cabilly et al.; Morrison et al., Proc. Natl. Acad. Sci. USA, 81:6851 6855 (1984)).

In the present invention, the term "humanized antibody" refers to an antibody or an antibody fragment that is a human immunoglobulin (recipient antibody) in which the entire or part of the CDR region is replaced by the CDR region of a non-human antibody (donor antibody). The donor antibody can be a mouse, rat or rabbit antibody having the desired specificity, affinity, and reactivity. In addition, the amino acid sequence of the human immunoglobulin framework region (FR) can also be replaced by corresponding amino sequence of non-human antibody. Furthermore, the amino acid residue of the humanized antibody may be neither from the recipient antibody nor from the CDR region or FR sequence of the donor antibody. The aim of these modifications is to further refine or optimize antibody performance. In general, the humanized antibody refers to an antibody, which comprises at least one, and usually two, almost complete variable regions. In these variable regions, all or substantially all of the corresponding CDR regions come from a non-human antibody and all or substantially all of the FR regions come from a human antibody. The ideal humanized antibody comprises at least part of an immunoglobulin Fc region, usually the Fc region of a human immunoglobulin. For further details, please see Jones et al., Nature, 321:522 525 (1986); Reichmann et al., Nature, 332:323 329 (1988); Presta, Curr. Op. Struct. Biol., 2:593 596 (1992); and Clark, Immunol. Today 21: 397 402 (2000).

The term "isolated" related to the present invention means obtained via artificial ways under natural state. If an "isolated" substance or composition appears in nature, then its natural environment might haven changed or it might be separated from its natural environment, or both. For example, a polynucleotide or a polypeptide naturally present in a living animal ant is not "isolated," while the same polynucleotide or polypeptide of high purity separated from this natural state is called "isolated". "Isolated" as used herein does not exclude mixing with artificial or synthetic materials, or the presence of other impurities that do not interfere with the activity of the substance.

The term "vector" of the present invention refers to a nucleic acid transporting tool, into which a polynucleotide encoding a protein may be inserted so that the protein is expressed. A vector may be used to transform, transduce, or transfect a host cell so that the genetic element it carries is expressed within the host cell. Examples of vectors include plasmids, phagemids, cosmids, artificial chromosomes such as yeast artificial chromosomes (YAC), bacterial artificial chromosomes (BAC), or P1-derived artificial chromosomes (PAC), bacteriophages such as lambda phages or M13 phages, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain multiple elements that control expression, including promoter sequence, transcription initiation sequence, enhancer sequence, selection element, and reporter gene. In addition, the vector may contain an origin of replication. A vector may also include material that aid its entry into the cell, such as a viral particle, a liposome, or a protein coat, but not only these materials.

The term "host cell" of the present invention refers to a cell into which a vector is introduced. It includes the following cell types, for example prokaryotic cells such as *E. coli* or *B. subtilis* cells, fungal cells such as yeast cells or *Aspergillus* cells, insect cells such as *Drosophila* S2 or *Spodoptera* Sf9 cells, or animal cells such as fibroblasts, CHO cells, COS cells, NSO cells, HeLa cells, BHK cells, HEK 293 cells, or human cells.

The term "neutralizing antibody" refers to an antibody or a fragment thereof which is able to eliminate or significantly reduce the binding virulence of a target viral antigen.

The term "sequence identity percentage (%)" refers to the percentage of nucleic acids or amino acids in a candidate sequence that are identical with the corresponding nucleic acids or amino acids of nucleic acid sequence or polypeptide sequence respectively. The term "sequence identity percentage (%)" referred to herein with respect to the nucleic acid or polypeptide sequences is defined as the percentage of candidate nucleic acid sequence or amino acid residue sequence that is identical with target nucleic acid sequence or amino acid sequence, respectively. For a certain sequence, align it with the target sequence and if necessary, skip mutation gaps, to achieve the maximum sequence identity percentage, without considering any conservative mutation of similar sequences. Multiple alignment methods in the art can be used to determine the similarity of nucleic acid or amino acid sequence, for instance, available computer software include BLAST, BLAST-2, ALIGN, ALIGN-2 or Megalign (DNASTAR). Those skilled in the art can set appropriate parameters for alignment, including any algorithms needed to achieve maximal alignment over the full-length of the sequences being compared.

The term "specifically binds" refers to a non-random binding reaction between two molecules, such as between an antibody and an antigen against which the antibody is raised. Here, an antibody binding to a first antigen exhibits no detectable binding affinity or low level binding affinity with a second antigen. In certain embodiments, an antibody that specifically binds an antigen binds the antigen with a binding affinity ($K_D$) of $\leq 10^{-5}$ M (e.g., $10^{-6}$ M, $10^{-7}$ M, $10^{-8}$ M, $10^{-9}$ M, 10 M, etc.). $K_D$, which as used herein refers to the ratio of the dissociation rate to the association rate ($k_{off}/k_{on}$), may be determined using methods known to the skilled in the art.

Antibody

The present invention provides monoclonal antibodies that can specifically bind to subtype H5 avian influenza virus. Another aspect of this invention relates to monoclonal antibodies that can bind specifically to the hemagglutinin of subtype H5 avian influenza virus and its corresponding antigen-binding fragments.

The present invention provides anti-H5 monoclonal antibodies that are secreted by mice hybridoma cell strains 8G9, 13D4 and 20A11. These monoclonal antibodies are named after the hybridoma cell strains that produce them. Thus the anti-H5 monoclonal antibodies are produced by mice hybridoma cell strains 8G9, 13D4 and 20A11 respectively, and they are named as monoclonal antibodies 8G9, 13D4 and 20A11 respectively. Monoclonal antibodies 8G9, 13D4 and 20A11 can specifically bind to the hemagglutinin of subtype H5 avian influenza virus. The mice hybridoma cell strains 8G9, 13D4 and 20A11 have been deposited in China Center for Typical Culture Collection (CCTCC, Wuhan University, Wuhan 430072, P.R. China) on Dec. 13, 2006 with deposit numbers of CCTCC-C200639 (hybridoma cell strain 8G9), CCTCC-C200605 (hybridoma cell strain 3C8), CCTCC-C200638 (hybridoma cell strain 20A11). The mice hybridoma cell strain 13D4 was also deposited on May 29, 2007 with the deposit number CCTCC-C200721.

The present invention also provides monoclonal antibodies that can block the binding of monoclonal antibodies 8G9, 13D4 and 20A11 to the hemagglutinin of subtype H5 avian influenza virus. The hemagglutinin epitopes bound by these blocking monoclonal antibodies may be the same as those recognized by monoclonal antibodies 8G9, 13D4 and 20A11. Epitopes recognized by these blocking monoclonal antibodies may also overlap sterically with those recognized by monoclonal antibodies 8G9, 13D4 and 20A11. Those blocking monoclonal antibodies can reduce the binding of monoclonal antibodies 8G9, 13D4 and 20A11 to the hemagglutinin of subtype H5 avian influenza virus by at least 50%, or at least 60%, or preferably at least 70%, or more preferably at least 75%, or more preferably at least about 80%, more preferably at least 85%, or even more preferably at least 90%, or even more preferably at least 95%, or most preferably at least 99%.

The ability of an unknown monoclonal antibody to reduce the binding of a known monoclonal antibody to the H5 hemagglutinin is measured by a routine method such as that described in *Antibodies: A Laboratory Manual*, Cold Spring Harbor Laboratory, Ed Harlow and David Lane (1988). For example, first pre-coat a microtiter plate with antigens, and then incubate the above mentioned pre-coated plates with serial dilutions of the unlabeled test antibodies admixed with a selected concentration of the labeled known antibodies. After washing, detect and measure the amount of the known antibodies bound to the plates at the various dilutions of the test antibodies. The stronger the ability of the test antibodies to compete with the known antibodies for binding to the antigens, the weaker the ability of the known antibodies to bind to the antigens. Usually, the antigens are pre-coated on a 96-well plate, and the ability of unlabeled antibodies to block the binding of labeled antibodies is measured using radioactive or enzyme labels.

Monoclonal antibodies may be generated by the hybridoma method reported by Kohler et al., Nature 256: 495 (1975). Firstly, a mouse or other appropriate host animal is immunized by injecting an immunogen (and an adjuvant if necessary). Typically, the injection manner of the immunogen or adjuvant is multiple subcutaneous or intraperitoneal injections. Conjugating the immunogen in advance to certain known proteins, such as serum albumin, or soybean trypsin inhibitor may be helpful for increasing the immunogenicity of the antigen in host cells. Examples of adjuvants which may be employed include Freund's complete adjuvant and MPL-TDM. After immunization, the host animal makes lymphocytes that produce antibodies specifically binding to immunogens. Alternatively, lymphocytes may be obtained by in vitro immunization. Collect desired lymphocytes and fuse them with myeloma cells using a suitable fusing agent, such as PEG, to form a hybridoma cell (Goding, *Monoclonal Antibodies: Principles and Practice*, pp. 59 103, Academic Press, 1996).

The hybridoma cells thus prepared can be seeded and grown in a suitable culture medium that preferably contains one or more substances that inhibit the growth or survival of the unfused, parental myeloma cells. For example, for parental myeloma cells lacking the enzyme hypoxanthine guanine phosphoribosyl transferase (HGPRT or HPRT), add substances such as hypoxanthine, aminopterin, and thymidine to the culture medium (HAT medium) would prevent the growth of HGPRT-deficient cells.

Preferred myeloma cells should have the capacities of fusing efficiently, stable abilities of antibody secretion, and being sensitive to HAT medium. Among these, preferred myeloma cell lines are murine myeloma lines, such as those derived from MOP-21 and MC-11 mouse tumors (THE Salk Institute Cell Distribution Center, San Diego, Calif. USA), and SP-2/0 or X63-Ag8-653 cell lines (American Type Culture Collection, Rockville, Md. USA). In addition, human myeloma and mouse-human heteromyeloma cell lines also have been reported for the production of human monoclonal antibodies (Kozbor, J. Immunol. 133: 3001 (1984); Brodeur et al., *Monoclonal Antibody Production Techniques and Applications*, pp. 51-63, Marcel Dekker, Inc., New York, 1987).

Culture medium in which hybridoma cells are growing is used for detecting the production of monoclonal antibodies directed against specific antigen. The binding specificity of monoclonal antibodies produced by hybridoma cells is determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis described by Munson et al. in Anal. Biochem. 107: 220 (1980).

After the specificity, affinity, and reactivity of the antibodies produced by hybridoma cells are determined, the target cell lines may be subcloned by standard limiting dilution procedures as described in Goding, Monoclonal Antibodies: Principles and Practice, pp. 59 103, Academic Press, 1996. Suitable culture media may be, for example, DMEM or RPMI-1640 medium. In addition, the hybridoma cells may be grown in vivo as ascites tumors in an animal.

The monoclonal antibodies secreted by the subclones can be separated from the culture medium, ascites fluid, or serum by conventional immunoglobulin purification procedures such as, for example, protein A-SEPHAROSE™ hydroxylapatite chromatography, gel electrophoresis, dialysis, or affinity chromatography.

Monoclonal antibodies of the present invention may also be obtained by genetic engineering recombinant methods. DNA molecules encoding the heavy and light chains of the monoclonal antibodies may be isolated from the hybridoma cells through PCR amplification using nucleic acid probes specifically binding to genes encoding the heavy and light chains of the monoclonal antibodies. The DNA molecules are inserted into expression vectors, which are then transfected into host cells such as *E. coli* cells, simian COS cells, Chinese hamster ovary (CHO) cells, or other myeloma cells that do not produce immunoglobulin protein. The transfected host cells are cultured under specific conditions and express the desired antibodies.

The antibodies of the present invention can bind to the H5 hemagglutinin with high specificity and affinity. These antibodies might have low cross-reactivity with other subtypes of hemagglutinin, preferably, these antibodies have completely no cross-reactivity with other subtypes of hemagglutinins. In one aspect, the invention provides antibodies that bind to H5 hemagglutinin with a $K_D$ value of less than $1\times10^{-5}$M. Preferably, the $K_D$ value is less than $1\times10^{-6}$M. More preferably, the $K_D$ value is less than $1\times10^{-7}$M. Most preferably, the $K_D$ value is less than $1\times10^{-8}$M.

The antibodies of the present invention may be the conventional "Y" shape structure antibodies comprised of two heavy chains and two light chains. In addition, the antibodies may also be the Fab fragment, the Fab' fragment, the $F(ab)_2$, fragment or the Fv fragment, or other types of partial fragment of the conventional "Y" shaped antibodies that maintain binding affinity to the hemagglutinin. The binding affinity of the fragments to hemagglutinin may be higher or lower than that of the conventional "Y" shaped antibodies.

The antibody fragments of the present invention may be obtained via proteolytic digestion of intact antibodies (see Morimoto et al., J. Biochem. Biophys. Methods 24:107-117 (1992) and Brennan et al., Science 229:81 (1985)). Additionally, these fragments can also be produced directly by recombinant host cells (reviewed in Hudson, Curr. Opin. Immunol. 11: 548-557 (1999); Little et al., Immunol. Today 21: 364 370 (2000)). For example, Fab' fragments can be directly recovered from *E. coli* or chemically coupled to form $F(ab')_2$ fragments (Carter et al., Bio/Technology 10:163 167 (1992)). In another example, the $F(ab')_2$ fragment can be obtained using the leucine zipper GCN4 for assembly. In addition, Fv, Fab or $F(ab')_2$ fragments can also be isolated directly from recombinant host cell culture. Other techniques for the production of antibody fragments are completely known to a person with ordinary skill in the art.

Antibody Nucleic Acid Sequences

The present invention provides nucleic acid molecules encoding antibodies or fragments thereof that specifically bind to H5 hemagglutinin. Nucleic acid molecules encoding the antibodies can be isolated from hybridoma cells. The nucleic acid sequences of the molecules can be determined using routine techniques known to a person with ordinary skill in the art. Nucleic acid molecules of the present invention can also be prepared using conventional genetic engineering recombinant techniques or chemical synthesis method. In one aspect, the sequence of the antibody nucleic acid molecule of the present invention comprises nucleic acid sequences encoding the variable region of the heavy chain of an anti-H5 antibody or a portion of the nucleic acid molecule of the antibody molecule. In another aspect, the sequence of the antibody nucleic acid molecule of the present invention also comprises nucleic acid sequences encoding the variable region of the light chain of an anti-H5 antibody or a portion of the nucleic acid molecule of the antibody molecule. In another aspect, the sequence of the antibody nucleic acid molecule of the present invention also comprises the CDR sequences of the antibody heavy chain or light chain variable regions. Complementary determinant region (CDR) is the site binding to epitope on antigen. CDR in the present research is determined according to IMGT/V-QUEST (http://imgt-.cines.fr/textes/vquest/). But CDR sequence determined by different method is slightly different.

One aspect of the present invention provides nucleic acid molecules encoding the variable regions of the heavy chain and light chain of monoclonal antibodies 8G9, 13D4 and 20A11. The nucleic acid sequences encoding the heavy chain variable regions of monoclonal antibodies 8G9, 13D4 and 20A11 correspond to SEQ ID NO: 1, SEQ ID NO:41, SEQ ID NO: 5, SEQ ID NO:43, SEQ ID NO:45 and SEQ ID NO: 9, respectively. The nucleic acid sequences encoding the light chain variable regions of monoclonal antibodies 8G9, 13D4 and 20A11 correspond to SEQ ID NO: 3, SEQ ID NO: 7 and SEQ ID NO: 11, respectively. The present invention also includes variants or analogs of the nucleic acid molecules encoding the variable regions of the heavy chain and light chain of monoclonal antibodies 8G9, 13D4 and 20A11.

In another aspect, the present invention also provides various isolated nucleic acid variants, whose sequences are identical with the following nucleic acid sequences SEQ ID NO: 1, SEQ ID NO: 3, SEQ ID NO: 5, SEQ ID NO: 7, SEQ ID NO: 9 or SEQ ID NO: 11. Specifically, the nucleic acid variants share at least 70% sequence identity, preferably at least 75% sequence identity, more preferably at least 80% sequence identity, more preferably at least 85% sequence identity, more preferably at least 90% sequence identity, most preferably at least 95% sequence identity, to the sequences of SEQ ID NO: 1, SEQ ID NO:41, SEQ ID NO: 3, SEQ ID NO: 5, SEQ ID NO:43, SEQ ID NO:45, SEQ ID NO: 7, SEQ ID NO: 9 or SEQ ID NO: 11.

The present invention also provides nucleic acid molecules encoding antibody fragments that are capable of specifically binding to subtype H5 of avian influenza virus.

The present invention further relates to corresponding isolated nucleic acid molecules encoding an antibody heavy chain variable region comprising the amino acid sequence set forth in SEQ ID NOs: 13-15, SEQ ID NOs: 19-21 and SEQ ID NOs: 25-27. The present invention also relates to corresponding nucleic acid molecules encoding an antibody light chain variable region comprising the amino acid sequence set forth in SEQ ID NOs:16-18, SEQ ID NOs: 22-24 and SEQ ID NOs:28-30.

The present invention relates to recombinant expressing vectors comprising the said nucleic acid molecules. It also relates to host cells transformed with the nucleic acid molecules. Furthermore, the present invention also relates to a method of culturing host cells containing said nucleic acid molecules under specific conditions and isolating the antibodies of the invention.

Antibody Polypeptide Sequences

The amino acid sequences of the variable regions of the heavy chain and light chain of monoclonal antibodies 8G9, 13D4 and 20A11 can be deduced from their respective nucleic acid sequences. The amino acid sequences of the heavy chain variable regions of monoclonal antibodies 8G9, 13D4 and 20A11 are set forth in SEQ ID NO:2, SEQ ID NO:42, SEQ ID NO:6, SEQ ID NO:44, SEQ ID NO:46 and SEQ ID NO: 10, respectively. The amino acid sequences of the light chain variable regions of monoclonal antibodies 8G9, 13D4 and 20A11 are set forth in SEQ ID NO:4, SEQ ID NO:8 and SEQ ID NO:12. In one aspect, the amino acid sequences of the heavy chain variable region contained in the anti-H5 monoclonal antibodies provided by the present invention are set forth in SEQ ID NO:2, SEQ ID NO:42, SEQ ID NO:6, SEQ ID NO:44, SEQ ID NO:46 and SEQ ID NO: 10. In another aspect, the amino acid sequences of the light chain variable region contained in the anti-H5 monoclonal antibodies provided by the present invention are set forth in SEQ ID NO:4, SEQ ID NO:8 and SEQ ID NO:12.

In another aspect, the present invention provides an antibody heavy chain comprising a variable region, the similarity of the amino acid sequences of this region to the amino acid sequences set forth in SEQ ID NO:2, SEQ ID NO:42, SEQ ID NO:6, SEQ ID NO:44, SEQ ID NO:46 or SEQ ID NO: 10 is at least 70%, preferably at least 75%, more preferably at least 80%, more preferably at least 85%, more preferably at least 90%, most preferably at least 95%.

In another aspect, the present invention provides an antibody light chain comprising a variable region, the similarity of the amino acid sequences of this region to the amino acid sequences set forth in SEQ ID NO:4, SEQ ID NO:8 or SEQ ID NO:12 is at least 70%, preferably at least 75%, more preferably at least 80%, more preferably at least 85%, more preferably at least 90%, most preferably at least 95%.

The amino acid sequences of the CDRs of the variable regions of the heavy chain and light chain of monoclonal antibodies 8G9, 13D4 and 20A11 have been determined as follows:

The amino acid sequences of CDR1, CDR2 and CDR3 of the heavy chain of monoclonal antibody 8G9 are set forth in SEQ ID Nos: 13-15, respectively. The amino acid sequences of CDR1, CDR2 and CDR3 of the light chain of monoclonal antibody 8G9 are set forth in SEQ ID Nos: 16-18, respectively.

The amino acid sequences of CDR1, CDR2 and CDR3 of the heavy chain of monoclonal antibody 13D4 are set forth in SEQ ID Nos: 19-21, respectively. The amino acid sequences of CDR1, CDR2 and CDR3 of the light chain of monoclonal antibody 13D4 are set forth in SEQ ID Nos: 22-24, respectively.

The amino acid sequences of CDR1, CDR2 and CDR3 of the heavy chain of monoclonal antibody 20A11 are set forth in SEQ ID Nos: 25-27, respectively. The amino acid sequences of CDR1, CDR2 and CDR3 of the light chain of monoclonal antibody 20A11 are set forth in SEQ ID Nos: 28-30, respectively.

In another aspect, the present invention provides an anti-H5 monoclonal antibody heavy chain or a fragment thereof, comprising the following CDRs: (i) one or more CDRs selected from SEQ ID NOs: 13-15; (ii) one or more CDRs selected from SEQ ID NOs: 19-21; (iii) one or more CDRs selected from SEQ ID NOs: 25-27. In one embodiment, the anti-H5 monoclonal antibody heavy chain or a fragment thereof comprises three CDRs having the amino acid sequences set forth in SEQ ID NOs: 13-15, respectively. In another embodiment, the anti-H5 monoclonal antibody heavy chain or a fragment thereof comprises three CDRs having the amino acid sequences set forth SEQ ID NOs: 19-21, respectively. In another embodiment, the anti-H5 monoclonal antibody heavy chain or a fragment thereof comprises three CDRs having the amino acid sequences set forth in SEQ ID NOs: 25-27.

In another aspect, the amino acid sequences contained in the CDRs of the anti-H5 monoclonal antibody heavy chains or fragments thereof may include one or more amino acid substitutions, additions or deletions from the amino acid sequences set forth in SEQ ID NOs: 13-15, 19-21 and 25-27. Preferably, the substituted, added or deleted amino acids are no more than three amino acids. More preferably, the substituted, added or deleted amino acids are no more than two amino acids. Most preferably, the substituted, added or deleted amino acid is no more than one amino acid.

In another aspect, the present invention provides an anti-H5 monoclonal antibody light chain or a fragment thereof, comprising the following CDRs: (i) one or more CDRs selected from SEQ ID NOs: 16-18; (ii) one or more CDRs selected from SEQ ID NOs: 22-24; (iii) one or more CDRs selected from SEQ ID NOs:28-30. In one embodiment, the anti-H5 monoclonal antibody light chain or a fragment thereof comprises three CDRs having the amino acid sequences set forth in SEQ ID NOs: 16-18, respectively. In another embodiment, the anti-H5 monoclonal antibody light chain or a fragment thereof comprises three CDRs having the amino acid sequences set forth in SEQ ID NOs: 22-24, respectively. In another embodiment, the anti-H5 monoclonal antibody light chain or a fragment thereof comprises three CDRs having the amino acid sequences set forth in SEQ ID NOs: 28-30.

In another aspect, the amino acid sequences contained in the CDRs of the anti-H5 monoclonal antibody light chains or fragments thereof may include one or more amino acid substitutions, additions or deletions from the amino acid sequences set forth in SEQ ID NOs: 16-18, 22-24 and 28-30. Preferably, the substituted, added or deleted amino acids are no more than three amino acids. More preferably, the substituted, added or deleted amino acids are no more than two amino acids. Most preferably, the substituted, added or deleted amino acid is no more than one amino acid.

The variants generated by amino acid substitution, addition or deletion in the variable regions of the above described antibodies or the above described CDRs still maintain the ability of specifically binding to subtype H5 of avian influenza virus. The present invention also includes such variants of antigen-binding fragments.

Monoclonal antibody variants of the present invention may be obtained by conventional genetic engineering methods. A person with ordinary skill in the art completely knows the method of reconstructing DNA molecules using nucleic acid mutation. Alternately, the nucleic acid molecules encoding the heavy and light chain variants may also be obtained by chemical synthesis.

Chimeric Antibodies, Humanized Antibodies and Fusion Proteins

In another aspect, the present invention also provides chimeric antibodies that comprise, in whole or in part, the heavy and/or light chain variable regions of murine monoclonal antibodies 8G9, 13D4 or 20A11 or a variant thereof, combined with the constant regions of a human monoclonal antibody. Additionally, the present invention includes humanized antibodies that comprise one or more of the CDRs of murine monoclonal antibodies 8G9, 13D4 or 20A11 or a variant thereof, grafted into a human antibody framework.

In another aspect, the present invention also provides a fusion protein comprising, in whole or in part, the monoclonal antibody of the invention, conjugated with certain molecules.

The chimeric antibodies, humanized antibodies and the fusion proteins all may be obtained using conventional genetic engineering methods. For example, DNA encoding the monoclonal antibodies may be modified by substituting the coding sequence for human heavy and light chain constant domains in place of the homologous murine sequences (Morrison, et al., Proc. Nat. Acad. Sci. 81: 6851 (1984)), or by covalently joining to the non-immunoglobulin coding sequence all or part of the coding sequence of an immunoglobulin to produce the chimeric or humanized antibodies or the fusion proteins.

Neutralizing Antibodies

In another aspect, the present invention provides anti-H5 antibodies that are capable of neutralizing the viral activity of subtype H5 avian influenza virus. In one embodiment, such neutralizing antibodies are capable of neutralizing at least 60%, or at least 70%, or preferably at least 75%, or preferably at least 80%, or preferably at least 85%, or preferably at least 90%, even more preferably at least 95%, most preferably at least 99% of the viral activity of subtype H5 avian influenza virus.

A person with ordinary skill in the art completely knows that the ability of an antibody to neutralize the viral activity of subtype H5 avian influenza virus can be determined using conventional methods. The neutralizing assay described in example 1 of the present invention can be used to determine the neutralizing activity of a certain anti-H5 monoclonal antibody of the invention.

Short Peptides

The present invention also provides a short peptide that mimics the recognition epitope of monoclonal antibody.

The present invention provides 9 short peptides (SEQ ID NOS: 31-39, 40) comprising twelve amino acids that bind specifically to the monoclonal antibody 8G9.

Detection Methods

The present invention further provides a method for detecting antigen and/or antibody in a type H5 avian influenza virus sample using a monoclonal antibody of the invention.

In one aspect, the present invention provides a method for detecting the subtype H5 avian influenza virus comprising the following steps: (i) contacting the virus in said sample with an monoclonal antibody or a fragment thereof of the invention to form a complex of said antibody or fragment with said virus; (ii) detecting said complex to determine the presence of said virus in said sample.

In another aspect, the present invention provides a method for detecting the subtype H5 avian influenza virus in a sample comprising the following steps: (i) attaching a first antibody to a solid substrate; (ii) adding a sample suspected of having subtype H5 avian influenza virus to said substrate; (iii) adding a second antibody that is linked to a labeling agent to said substrate; (iv) detecting the presence of the labeling agent to measure the presence of subtype H5 avian influenza virus.

Another aspect of the present invention provides a method for detecting the subtype H5 avian influenza virus in a sample comprising the following steps: (i) attaching an antibody to a solid substrate; (ii) adding a sample suspected of having subtype H5 avian influenza virus pre-mixed with labeled H5 hemagglutinin to said substrate; and (iii) detecting the presence of the labeled H5 hemagglutinin.

The detection methods may use enzyme-linked immunosorbent assay (ELISA), enzyme immunoassay, chemiluminescence immunoassay, radioimmunoassay, fluorescence immunoassay, immunochromatography, competition assay and detection method the like. The above detection methods can be used to detect the target antigens or antibodies via competition or sandwich methods.

The competition method is a quantitative relation comparing the competitive binding of an antigen in a sample and a known amount of a labeled antigen to the monoclonal antibody of the present invention. To carry out an immunological assay based on the competition method, a sample containing an unknown amount of the target antigen is added to a solid substrate to which the monoclonal antibody of the present invention is coated physically or chemically by known means, and the reaction is allowed to proceed. Simultaneously, a predetermined amount of the pre-labeled target antigen is added and the reaction is allowed to proceed. After incubation, the solid substrate is washed and the activity of the labeling agent bound to the solid substrate is measured.

In the sandwich method, the target antigen in a sample is sandwiched between the immobilized monoclonal antibody and the labeled monoclonal antibody, then a labeling substrate such as an enzyme is added, substrate color changes are detected, and thereby detecting the presence of the antigen. To carry out an immunological assay based on the sandwich method, for instance, a sample containing an unknown amount of the target antigen is added to a solid substrate to which the monoclonal antibody of the present invention is coated physically or chemically by known means, and the reaction is allowed to proceed. Thereafter, the labeled monoclonal antibody of the invention is added and the reaction is allowed to proceed. After incubation, the solid substrate is washed and the activity of the labeling agent bound to the solid substrate is measured. The labeling agent may be radioisotopes such as $^{125}I$, enzymes, enzyme substrates, luminescent substances such as isoluminol and acridine esters, fluorescent substances such as fluorescein and rhodamine, biotin, and colored substances such as colored latex particles and colloidal gold. Labeling enzymes may be peroxidase (e.g. Horse Radish Peroxidase (HRP)), alkaline phosphatase, β-galactosidase, and glucose oxidase. Suitable substrates for the reactions may be 2,2'-Azino-Bis-(3-Ethylbenzothiazoline-6-Sulfonic Acid), luminol-$H_2O_2$, o-phenylenediamine-$H_2O_2$ (against peroxidase), p-nitrophenyl phosphate, 4-methylumbelliferyl phosphate, 3-(2'-spiroadamantan)-4-methoxy-4-(3"-phosphoryloxy)phenyl-1,2-dioxetane (against alkaline phosphatase), p-nitrophenyl-β-D-galactose, and methylumbelliferyl-β-D-galactose (against β-galactosidase). Additional labels include quantum dot-labels, chromophore-labels, enzyme-labels, affinity ligand-labels, electromagnetic spin labels, heavy atom labels, probes labeled with nanoparticle light scattering labels or other probes of nanoparticles, fluorescein isothiocyanate (FITC), TRITC, rhodamine, tetramethylrhodamine, R-phycoerythrin, Cy-3, Cy-5, Cy-7, Texas Red, Phar-Red, allophycocyanin (APC), epitope tags such as the FLAG or HA epitope, and enzyme tags such as alkaline phosphatase, horseradish peroxidase, $I^2$-galactosidase, alkaline phosphatase, β-galactosidase, or acetylcholinesterase and hapten conjugates such as digoxigenin or dinitrophenyl, or members of a binding pair that are capable of forming complexes such as streptavidin/biotin, avidin/biotin or an antigen/antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue, dichlorotriazinylamine fluorescein, dansyl chloride, phycoerythrin, fluorescent lanthanide complexes such as those including Europium and Terbium, Cy3, Cy5, molecular beacons and fluorescent derivatives thereof, a luminescent material such as luminol; light scattering or plasmon resonant materials such as gold or silver particles or quantum dots; or radioactive material including $^{14}C$, $^{123}I$, $^{124}I$, $^{131}I$, Tc99m, $^{35}S$ or $^{3}H$; or spherical shells, and probes labeled with any other signal generating label known to those of skill in the art. For example, detectable molecules include but are not limited to fluorophores as well as others known in the art as described, for example, in Principles of Fluorescence Spectroscopy edited by Joseph R. Lakowicz (Editor), Plenum Pub Corp, 2nd edition (July 1999) and the $6^{th}$ Edition of the Molecular Probes Handbook by Richard P. Hoagland. In some embodiments, labels comprise semiconductor nanocrystals such as quantum dots (i.e., Qdots), see U.S. Pat. No. 6,207,392. Qdots are commercially available from Quantum Dot Corporation. The semiconductor nanocrystals useful in the practice of the invention include nanocrystals of Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe as well as mixed compositions thereof; as well as nanocrystals of Group III-V semiconductors such as GaAs, InGaAs, InP, and InAs and mixed compositions thereof. The use of Group IV semiconductors such as germanium or silicon, or the use of organic semiconductors, may be feasible under certain conditions. The semiconductor nanocrystals may also include alloys comprising two or more semiconductors selected from Group III-V compounds, Group II-VI compounds, Group IV elements, and combinations thereof.

In some embodiments, a fluorescent energy acceptor is linked as a label to a detection probe. In one embodiment the fluorescent energy acceptor may be formed as a result of a compound that reacts with singlet oxygen to form a fluorescent compound or a compound that can react with an auxiliary compound that is thereupon converted to a fluorescent compound. Such compounds can be comprised in buffers contained in a device of the invention. In other embodiments, the fluorescent energy acceptor may be part of a compound that includes the chemiluminescer or group. For example, the fluorescent energy acceptor may include a metal complex of a rare earth metal such as, e.g., europium, samarium, tellurium and the like. These materials are particularly attractive because of their sharp band of luminescence. Furthermore, lanthanide labels, such as europium (III) provide for effective and prolonged signal emission and are not easy to photo bleach, thereby allowing Test Devices containing processed/reacted sample to be set aside if necessary for a prolong period of time. Long-lifetime fluorescent europium(III) complex nanoparticles have been applied as labels in various heterogeneous and homogeneous immunoassays. See, e.g., Huhtinen et al. Clin. Chem. 2004 October; 50(10): 1935-6. Assay performance can be improved when these intrinsically labeled nanoparticles are used in combination with time-resolved fluorescence detection. In heterogeneous assays, the dynamic range of assays at low concentrations can be extended. Furthermore, the kinetic characteristics of assays can also be improved by the use of detection antibody-coated high-specific-activity nanoparticle labels instead of conventionally labeled detection antibodies. In homogeneous assays, europium(III) nanoparticles are efficient donors for fluorescence resonance energy transfer, enabling simple, rapid, and efficient screening. In some embodiments, a label (e.g., fluorescent label) disclosed herein, includes a nanoparticle label conjugated with biomolecules. In other words, a nanoparticle can be utilized as a detection or capture probe. For example, a europium(III)-labeled nanoparticle linked to monoclonal antibodies or streptavidin (SA) to detect a particular analyte in a sample can be utilized in practice of the present invention (e.g., nanoparticle-based immunoassay). The nanoparticles can serve as a substrate to which the specific binding agents are attached, these specific binding agents are for the analyte and either the detection (i.e., label) or capture moiety. Examples of labels can be found in U.S. Pat. Nos. 4,695,554; 4,863,875; 4,373,932; and 4,366,241. Colloidal metals and dye particles are disclosed in U.S. Pat. Nos. 4,313,734 and 4,373,932. The preparation and use of non-metallic colloids are disclosed in U.S. Pat. No. 4,954,452. Organic polymer latex particles for use as labels are disclosed in U.S. Pat. No. 4,252,459.

The labeling agents may be bound to the antigen or antibody by maleimide method (J. Biochem. (1976), 79, 233), activated biotin method (J. Am. Chem. Soc. (1978), 100, 3585), hydrophobic bond method, activated ester method or isocyanate method ("Enzyme immunoassay techniques", published in 1987 by Igaku Shoin).

When the above labeling agent is radioisotopes, the measurement needs to be carried out using a well counter or a liquid scintillation counter. When the labeling agent is an enzyme, the substrate needs to be added and the enzyme activity is measured by colorimetry or fluorometry. When the labeling agent is a fluorescent substance, luminescent substance or colored substance, the measurement can be made respectively by a method known in the art.

In this invention, the samples used for detecting subtype H5 avian influenza virus include but are not limited to the wastes from animals or patients, secretions from the mouth and nasal cavities, intact virus or lytic virus in the chicken embryo culture, etc.

Detection Devices and Kits

This invention further relates to a kit for diagnosis of the infection by subtype H5 avian influenza virus, especially to a kit for detecting the antigen or antibody of subtype H5 avian influenza virus in the sample. The diagnosis kit of the invention comprises at least one monoclonal antibody species of the invention. The monoclonal antibody of the invention, which is to be used in the diagnosis kit of the invention, is not particularly restricted but may be any of those monoclonal antibodies recognizing the H5 hemagglutinin antigen, and may also be any antigen-specific antibody fragment of the monoclonal antibodies of the invention such as $F(ab')_2$, Fab', Fab and the like.

In one aspect, this invention relates to two kinds of kits for detecting subtype H5 avian influenza virus which contain at least one of the monoclonal antibodies of the invention or their active fragments or variants. Preferably, the kits of the present invention also contain detecting reagent suitable for detecting the antigen-antibody reactions.

In another aspect, this invention relates to a kit for detecting anti-H5 subtype avian influenza virus antibody, which contains at least one of the monoclonal antibodies of the invention or their active fragments or variants. Preferably, the kit mentioned in this invention contains the detection reagent suitable for detecting the antigen-antibody reactions.

The solid substrate to be used in the diagnosis kits of the present invention includes, but is not limited, to microplates, magnetic particles, filter papers for immunochromatography, polymers such as polystyrene, glass beads, glass filters and other insoluble carriers. In one embodiment, a solid substrate containing many compartments or regions has at least one compartment coated with antibodies of the invention. Preferably, at least one compartment (or the first compartment) is coated with antibodies of the invention, furthermore, at least one of the rest compartments (or the second compartment) is coated with antibodies that can specifically bind to subtypes except of H5 of avian influenza virus (e.g. H1, H2, H3, H4, H6, H7, H9, H10, H11, H12, H13, H13, H14, H15 or H16). The preferred subtypes are H1, H3, H7, H9.

The diagnosis agent of the invention also comprises other constituent. The other constituent includes, but is not limited, to enzymes for labeling, substrates therefor, radioisotopes, light-reflecting substances, fluorescent substances, colored substances, buffer solutions, and plates, and those mentioned hereinabove.

In the diagnosis agent of the invention, the monoclonal antibody of the invention must be immobilized on a solid substrate in advance. In a preferred embodiment, orienting the immobilized monoclonal antibody will be helpful for enhancing the binding efficiency of the antibody to the antigen. TaeWoon Cha et al (*Proteomics* 5, 416-419 (2005)) have demonstrated that controlling the conformation of immobilized protein molecules and designing an ideal chemical environment on the solid substrate surface are helpful for preserving and enhancing the reaction activity and potency of the immobilized proteins. Various methods for attaching antibodies to a solid substrate in a desired conformation orientation have been reported by the literatures. Shawn Weng et al (*Proteomics* 2, 48-57 (2002)) reported a method of orienting proteins in a uniform manner on a surface through nucleic acids linked to the proteins. Soellner, M. et al (*J. AM. CHEM SOC.* 125, 11790-11791 (2003)) reported a method pursuant to which proteins including antibodies and antigens were bound to a surface in a uniform manner through Staudinger ligation in which an azide and phosphinothioester react to form an amide. Hairong Zhang et al (*Anal. Chem.,* 78, 609-616 (2006)) reported a method of orienting antibodies on gold-coated magnetic particles through reaction of the free thiols of the Fab' fragments of the antibodies to the surface of the particles, pursuant to which all the antigen binding sites of the antibodies were oriented in a favorable conformation. Hai Xu et al (*J. Phys. Chem. B,* 110, 1907-1914 (2006)) reported methods of adsorbing antibodies to the hydrophilic silicon oxide/water surface. Seung-yong Seong et al (*Proteomics,* 3, 2176-2189 (2003)) reviewed methods for oriented immobilization of proteins to a surface and protein molecules used in such methods. All these references are summed up herein in their entirety.

In the diagnosis kit of the present invention, the monoclonal antibody or antigen must be labeled with the above-mentioned labeling agent in advance.

The present invention further provides an automated detection device that is capable of detecting avian influenza virus in a sample through automated processes.

Various devices for detecting the presence of an analyte in a sample of biological fluid through the use of immunochemistry have been described in the art. These devices may utilize the so-called "sandwich" assay, for example, a target analyte such as an antigen is "sandwiched" between a labeled antibody and an antibody immobilized onto a solid support. The assay is read by observing the presence and/or amount of bound antigen-labeled antibody complex. These devices may also incorporate a competition immunoassay, wherein an antibody bound to a solid surface is contacted with a sample containing an unknown quantity of antigen analyte and with labeled antigen of the same type. The amount of labeled antigen bound on the solid surface is then determined to provide an indirect measure of the amount of antigen analyte in the sample. Different assays may utilize devices adapted to assay different analytes, for example, by incorporating different antibodies or antigens in designated or addressable regions of the test substrate (e.g., bibulous or non-bibulous membranes). Because these and other methods discussed below can detect both antibodies and antigens, they are generally referred to as immunochemical ligand-receptor assays or simply immunoassays.

Solid phase immunoassay devices, whether sandwich or competition type, can provide sensitive detection of an analyte in a biological fluid sample such as blood or urine. Solid phase immunoassay devices comprise a solid support to which one member of a ligand-receptor pair, usually an antibody, antigen, or hapten, is bound. Usually, forms of early solid supports were plates, tubes, or beads of polystyrene which were well known in the fields of radioimmunoassay and enzyme immunoassay. More recently, a number of porous materials such as nylon, nitrocellulose, cellulose acetate, glass fibers, and other porous polymers have been employed as solid supports. A number of self-contained immunoassay kits using porous materials as solid phase carriers of immunochemical components such as antigens, haptens, or antibodies have been disclosed by people. These kits are usually dipstick, flow-through, or migratory in design. Any of the conventional, known devices for performing immunoassays or specific binding assays may be utilized in the invention to detect influenza.

In certain aspects, the present invention includes devices for detection of infection caused by various influenza virus types or subtypes thereof. In some embodiments, a sample that contains one or more influenza viruses or anti-influenza virus antibodies is administered to a device to determine if the sample is from a subject infected with one or more influenza virus types or subtypes thereof A device comprising a solid support can comprise anti-influenza virus antibodies or influenza virus antigens disposed thereon, thus is able to test a sample suspected of containing an influenza virus, influenza virus protein or an anti-influenza virus antibody. In various embodiments, antibodies utilized in devices of the present invention include but are not limited to: a polyclonal, a monoclonal antibody (MAb), or conservative or functional variants thereof, a chimeric antibody, a reshaped antibody, a humanized antibody, a bioactive fragment thereof, or any combination of such antibodies; any of such functional antibodies or fragments thereof, on the whole, refer to antibody. Antibodies of the invention can be adapted to any devices to detect influenza virus. For example, H5 avian influenza virus can be detected by targeting of an H5 protein or an anti-subtype H5 antibody in a sample. In one embodiment, H5 is from Avian Influenza Virus (AIV).

Many commercially available devices can be easily adapted to incorporate antibodies or antigens disclosed herein. These devices can incorporate solid substrate used in the detection methods, including without limitation microplates, magnetic particles, filter papers for immunochromatography, polymers such as polystyrene, glass beads, glass filters and other insoluble carriers. The substrate generally will be in shapes including but not limited to a strip, sheet, chip, sphere, bead, well such as a well in micro titer plate, or any other suitable shapes. Furthermore, the substrate to which a binding partner (i.e., antigen or antibody) is bound may be in any of a variety of forms, e.g., a microtiter dish, a test tube, a dipstick, a microcentrifuge tube, a bead, a spinnable disk, and the like. Suitable materials include glass, plastic (e.g., polyethylene, PVC, polypropylene, polystyrene, and the like), protein, paper, carbohydrate, and other solid supports. Other materials that may be employed include ceramics, metals, metalloids, semiconductive materials, cements and the like. In some embodiments, microtiter plates utilized in immunoassays (e.g., ELISA) comprise 96 well, 384 well plates or 1536 well formats, or higher number of wells, such as other commercial plates.

Some available devices include dipstick, lateral flow, cartridge, multiplexed, microtiter plate, microfluidic, plate or arrays or high throughput platforms, such as those disclosed in U.S. Pat. Nos. 6,448,001; 4,943,522; 6,485,982; 6,656,744; 6,811,971; 5,073,484; 5,716,778; 5,798,273; 6,565,808; 5,078,968; 5,415,994; 6,235,539; 6,267,722; 6,297,060; 7,098,040; 6,375,896; 7,083,912; 5,225,322; 6,780,582; 5,763,262; 6,306,642; 7,109,042; 5,952,173 and 5,914,241. Exemplary microfluidic devices include those disclosed in U.S. Pat. No. 5,707,799 and WO 2004/029221.

Dipstick

In some very common forms of dipstick assays, as in home pregnancy and ovulation detection kits, immunochemical components such as antibodies are bound to a solid phase. The assay device is "dipped" for incubation into a sample suspected of containing unknown antigen analyte. Alternatively a small amount of sample can be placed onto a sample receiving zone. A labeled antibody is then added and the label is detected as an indication of the presence of the analyte of interest. In some cases the label is an enzyme so an enzyme-labeled antibody needs to be added, either simultaneously or after an incubation period. Next, the device is washed and then inserted into a second solution containing a substrate for the enzyme. The enzyme-label, if present, interacts with the substrate, causing the formation of colored products which either deposit as a precipitate onto the solid phase or produce a visible light change in the substrate solution. Baxter et al. in EP-A 0 125 118 disclose such a sandwich type dipstick immunoassay. Kali et al. in EP-A 0 282 192 disclose a dipstick device can be used in competition type assays. The materials of the T dipstick, formats and labels are known and can be used in an influenza assay. Exemplary dipstick devices include those described in U.S. Pat. Nos. 4,235,601, 5,559,041, 5,712,172 and 6,790,611. In some embodiments, antibodies of the present invention can be disposed onto a dipstick device. For example, anti-subtype H5 AIV antibody in a sample can be detected through the use of a solid phase support dipstick, which can be attached at one or more matrix squares. One matrix square can have a non-specific control antibody or a functional fragment thereof attached. These matrix squares can be the sites of protein-binding and/or antigen-binding in and are usually made of nitrocellulose; however, any suitable medium known in the art can be utilized, such as certain nylons and polyvinylidenes. In some embodiments a multitude of matrices can be attached to the solid support. Each matrix contains an antigen or antibody for a plurality of influenza virus subtypes.

Flow-Through

The design of flow-through type immunoassay devices can obviate the need for extensive incubation and cumbersome washing steps in dipstick assays. Valkirs et al. in U.S. Pat. No. 4,632,901 disclose a device comprising antibody (specific to a target antigen analyte) bound to a porous membrane or filter to which a liquid sample is added. Since the liquid flows by or continuously flows through the membrane, target analyte binds to the antibody. The addition of sample may be followed by addition of labeled antibody. The visual detection of labeled antibody can indicate the presence of target antigen analyte in the sample. Korom et al. in EP-A 0 299 359 discloses an improvement in the flow-through device in which the labeled antibody is incorporated into a membrane which acts as a reagent delivery system. Such devices may comprise layers which serve as filters for components in the sample and include the reagents utilized in the assay. As the sample flows from one layer to another, it contacts and reacts with the specific binding reagents and in some instances, the components of the labeling system can provide an indication of the presence of the target analyte.

Immunofiltration Devices.

Immunofiltration devices are commercially available (e.g., Pierce, Rockford, Ill.) and can be easily adapted to incorporate antibodies of the present invention. In an enzyme-linked immunoflow assay (ELIFA) method, a nitrocellulose membrane sandwiched between a 96-well sample application plate and a vacuum chamber is used. Reactants are added to the sample application plate and the vacuum allows the reactants to pass through the membrane. Cannulas transfer unbound products to the collection chamber. For detection, a microtest plate (microwell plate) is placed in the collection chamber before adding the enzyme substrate. The vacuum allows transference of the colored product into the wells of the microtest plate for analysis in an automated microtest plate reader. The ELIFA system is composed of precision cut plexiglass with tight sealing gaskets that provide constant flow rates from well to well. The cannulas can precisely transfer colored product to the wells of microtest plate for analysis. Basically, a capture antibody of the invention is spotted on the substrate (e.g., microtiter plate, membrane or chip). A biological sample suspected of containing influenza virus or influenza virus antigens are applied and incubated to allow the capture antibodies to bind. Subsequently, a detection antibody is added. A high-throughput immunofiltration device is disclosed in U.S. Patent Application 2003/0108949. Such devices may comprise layers which serve as filters and/or include the reagents utilized in the assay. As the sample reacts with the specific binding reagents and in some cases components of the labeling system can provide an indication of the presence of a certain analyte.

Lateral Flow Devices

In lateral flow type assays, a membrane is impregnated with the some or all of the reagents needed to perform the assay. An analyte detection zone is provided in which labeled analyte is detected. See, for example, U.S. Pat. No. 4,366,241 of Tom et al., and EP-A 0 143 574 of Zuk. It is known that many improvements can be made for lateral flow assay devices. This device may comprise some of the reagents for the specific binding assay (the sample may react with some reagents before applying to the lateral flow strip or additional reagents may be sequentially applied to the strip) or the strip may contain all of the necessary reagents for the specific binding assay. Lateral flow devices frequently incorporate within them reagents which can be attached to colored labels, thereby detection result can be directly observed without the addition of further substances. See, for example, U.S. Pat. No. 4,770,853 of Bernstein, WO 88/08534 of May et al., and EP-A 0 299 428 of Ching et al. Devices of this kind are generally constructed to include a location for the application of the sample, a reagent zone and a detection zone. The device is typically made from a bibulous material which permits the sample to flow continuously from the sample application zone through the reagent or reaction zone to the detection zone. While some of the reactions may have occurred before the application of the sample to the strip, in some embodiments, the reaction zone includes the reagents for the immunoassay. One specific binding reagent, for example an antibody, may be diffusively bound to the strip in the sample application zone or a reaction zone so that it can bind the antigen in the sample and flow with the sample along the strip. The antigen-antibody complex may be captured in the detection zone directly with another specific binding partner to the antigen or antibody or with other specific binding partners, such as avidin or streptavidin and biotin to capture indirectly. Similarly, the label may be directly or indirectly attached to the antigen or antibody. For exemplary lateral flow devices, see U.S. Pat. Nos. 4,818,677, 4,943,522, 5,096,837 (RE 35,306), 5,096,837, 5,118,428, 5,118,630, 5,221,616, 5,223,220, 5,225,328, 5,415,994, 5,434,057, 5,521,102, 5,536,646, 5,541,069, 5,686,315, 5,763,262, 5,766,961, 5,770,460, 5,773,234, 5,786,220, 5,804,452, 5,814,455, 5,939,331, and 6,306,642. Other lateral flow devices that may be modified for use in the detection of multiple analytes in a fluid sample are disclosed in U.S. Pat. Nos. 4,703,017, 6,187,598, 6,352,862, 6,485,982, 6,534,320 and 6,767,714.

In the conventional technique, multiple analytes from a sample can be analyzed using a single test strip by establishing separate detection zones for each analyte. Distinguishing between different analytes can be accomplished by using different labels or by measuring the same label in the different detection zones. Assaying for multiple analytes can be accomplished with any of the conventional devices.

Immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of a particular antigen in a test sample.

Such a lateral flow device usually comprises a porous membrane optionally supported by a rigid material. In general, the porous membrane may be made from many materials through which a fluid is allowed to pass. For example, the materials used to form the porous membrane may include, but are not limited to, natural material, synthetic material, or naturally occurring materials that are synthetically modified, such as polysaccharides (e.g., cellulose materials such as paper and cellulose derivatives, such as cellulose acetate and nitrocellulose); polyether sulfone; polyethylene; nylon; PVDF; polyester; polypropylene; silica; inorganic materials, such as deactivated alumina, diatomaceous earth, MgSO4, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous permeable gels, such as silica gel, agarose, dextran, and gelatin; polymeric films, such as polyacrylamide and the like. In one particular embodiment, said porous permeable membrane is formed from nitrocellulose and/or polyether sulfone materials. It should be understood that the term "nitrocellulose" refers to nitric acid esters of cellulose, which may be nitrocellulose alone, or its mixture with nitric acid ester or other acid esters, such as aliphatic carboxylic acid esters having from 1 to 7 carbon atoms.

Such a device may also contain a strip with an absorbent pad disposed upstream or downstream of the test/detection or control zones. As is well known for the person skilled in the art, the absorbent pad may assist in promoting capillary action and fluid flow through the membrane. In some embodiments, absorbent pads may contain mobilizable immunoassay reagents (e.g., antibodies). Of course, it needs to be understood that the mobilizable or immbolized immunoassay reagents can also be disposed anywhere upstream of the detection/test or control zones, as in separate components of a detection system.

In many embodiments, some suitable materials that may be used to form the sample pad include, but are not limited to, nitrocellulose, cellulose, porous polyethylene pads, and glass fiber filter paper. If desired, the sample pad may also contain one or more pretreated assay reagents, either covalently or non-covalently attached thereto. The test sample travels from the sample pad to a conjugate pad that is placed in communication with one end of the sample pad. The conjugate pad is formed from a material through which a fluid is capable of passing. For example, in one embodiment, the conjugate pad is formed from fiberglass. It should be understood that other conjugate pads may also be used in the present invention. Alternatively, in some embodiments conjugates or other immunoreagents may be included in a component that is mixed with a sample prior to the application to a test strip.

To facilitate detection of the presence or absence of an analyte within the test sample, various detection probes may be applied to the conjugate pad. While contained on the conjugate pad, these detection probes remain available for binding with the analyte as it passes from the sampling pad through the conjugate pad. Upon binding with the analyte, the detection probes are later served to identify the presence or absence of the analyte. The detection probes may be used for the detection or calibration of the assay. In alternative embodiments, however, separate calibration probes may be applied to the conjugate pad for use in conjunction with the detection probes to facilitate simultaneous calibration and detection, thereby eliminating inaccuracies often created by conventional assay calibration systems.

In some instances, it may be desired to modify the detection probes in some manner so that they are more readily able to bind to the analyte. In such instances, the detection probes may be modified by certain specific binding members that are adhered thereto to form conjugated probes. Specific binding members generally refer to a member of a specific binding pair, i.e., two different molecules where one of the molecules chemically and/or physically binds to the second molecule. For instance, immunoreactive specific binding members may include antigens, haptens, aptamers, antibodies (primary or secondary), and complexes thereof, including those substances formed by recombinant DNA methods or peptide synthesis methods. An antibody may be a monoclonal or polyclonal antibody, a recombinant protein or a mixture(s) or fragment(s) thereof, or a mixture of an antibody and other specific binding members. The details of the preparation of such antibodies and their suitability for use as specific binding members are disclosed herein. Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs include members that are similar to the original specific member. For example, a derivative or fragment of the analyte, e.g., an analyte-analog, may be used so long as it has at least one epitope in common with the analyte.

In one embodiment, for instance, the fluid containing the test sample is transported to the gold pad, where the analyte mixes with detection probes modified with a specific binding member to form analyte complexes. Because flow is unimpeded between the gold pad and the porous membrane, the complexes may migrate from the gold pad to a detection zone present on the porous membrane. Alternatively, multiple detection zones can be utilized by incorporating antibodies specific for different antigens (e.g., different influenza virus or viral antigens from different influenza virus). The detection zone(s) may contain an immobilization reagent that is generally capable of forming a chemical or physical bond with the analyte and/or complexes thereof (e.g., complexes of the analyte with the detection probes). In some embodiments, the reagent may be a biological reagent, such as antibodies disclosed herein. Other biological reagents are well known to the person skilled in the art and may include, but are not limited to, antigens, haptens, antibodies, protein A or G, avidin, streptavidin, or complexes thereof. In some cases, it is desired that these biological reagents are capable of binding to the analyte and/or the complexes of the analyte with the detection probes.

These reagents serve as stationary binding sites for the detection probe/analyte complexes. In some instances, the analytes, such as antibodies, antigens, etc., have two binding sites. Upon reaching the detection zone(s), one of these binding sites is occupied by the specific binding member of the complexed probes. However, the free binding site of the analyte may bind to the immobilization reagent. Upon being bound to the immobilization reagent, the complexed probes form a new ternary sandwich complex.

The detection or test zone(s) may generally provide any number of distinct detection regions so that a user may better determine the presence of a particular analyte within a test sample. Each region contains the same reagents, or contains different reagents for immobilizing multiple analytes. For example, the detection zone(s) may include two or more distinct detection regions (e.g., lines, dots, etc.).

In some cases, the membrane may also define a control zone (not shown) that can be used to give the user a signal that the assay is performing properly. For instance, the control zone (not shown) may contain an immobilization reagent that generally has the ability of forming a chemical and/or physical bond with probes or with the reagent immobilized on the probes. Such reagents include, but are not limited to, for example, antigens, haptens, antibodies, protein A or G, avidin, streptavidin, secondary antibodies, or complexes thereof. In addition, it may also be desired to utilize various non-biological materials for the control zone reagent. For instance, in some embodiments, the control zone reagent may also include a polyelectrolyte, such as described above, that may bind to uncaptured probes. Because the reagent at the control zone is only specific for probes, a signal forms regardless of whether the analyte is present. The control zone may be positioned at any location along the membrane, but is preferably positioned upstream of the detection zone.

Various formats may be used to test for the presence or absence of an analyte using the assay. For instance, in the embodiment described above, a "sandwich" format is utilized. For other examples using such sandwich-type assays, see U.S. Pat. No. 4,168,146 of Grubb, et al. and U.S. Pat. No. 4,366,241 of Tom, et al., which are incorporated herein in their entirety by reference. In addition, other formats, such as "competitive" formats, may also be utilized. In a competitive assay, the labeled probe is generally paired with a molecule that is identical to, or similar to, the analyte. Thus, the labeled probe competes with the analyte of interest for the available reagent. Competitive assays are usually used for the detection of analytes such as haptens, each monovalent hapten is capable of binding only one antibody molecule. For examples of competitive immunoassay devices, see U.S. Pat. No. 4,235,601 of Deutsch, et al., U.S. Pat. No. 4,442,204 of Liotta, and U.S. Pat. No. 5,208,535 of Buechler, et al., which are incorporated herein in their entirety by reference. For devices of other forms, see U.S. Pat. No. 5,395,754 of Lambofte, et al.; U.S. Pat. No. 5,670,381 of Jou, et al.; and U.S. Pat. No. 6,194,220 of Malick, et al., which are incorporated herein in their entirety by reference.

Microfluidic Devices

In some aspects of the present invention, antibodies disclosed herein can be incorporated into a microfluidic device. The device is a microfluidic flow system capable of binding one or more analytes. The bound analytes may be directly analyzed on the device or be removed from the device, e.g., for further analysis or processing. Alternatively, analytes not bound to the device may be collected, e.g., for further processing or analysis.

An exemplary device is a flow apparatus having a flat-plate channel through which a sample flows; for such a device, see U.S. Pat. No. 5,837,115. Samples can be transferred to such device by gravity, capillary or by an active force, such as by an infusion pump to perfuse a sample, e.g., blood, into the microfluidic device. Other known transferring methods may also be used. Microfluidic devices may optionally rely on an array of structures in the device for analyte capture. The structures can be made by a variety of processes including, but not limited to lasering, embossing, Lithographie Galvanoformung Abformung (LIGA), electroplating, electroforming, photolithography, reactive ion etching, ion beam milling, compression molding, casting, driving force injection molding, injection molding, and micromachining the material. As needed to be understood, the methods utilized to manufacture the devices of the present invention are not critical as long as the method results in large quantities of uniform structures and devices. Furthermore, the method must result in a large surface area of the structure and arranged in close proximity to each other to produce a narrow channel. Said narrow channel allows analyte diffusion in the fluid to occur to enhance the efficiency of capturing analyte and/or labeled reagent at the capture site.

The mass produced structures are preferably made of any number of polymeric materials. Included among these are, but not limited to, polyolefins such as polypropylene and polyethylene, polyesters such as polyethylene terephthalate, styrene containing polymers such as polystyrene, styrene-acrylonitrile, and acrylonitrilebutadienestyrene, polycarbonate, acrylic polymers such as polymethylmethacrylate and poly acrylonitrile, chlorine containing polymers such as polyvinylchloride and polyvinylidenechloride, acetal homopolymers and copolymers, cellulosics and their esters, cellulose nitrate, fluorine containing polymers such as polyvinylidenefluoride, polytetrafluoroethylene, polyamides, polyimides, polyetheretherketone, sulfur containing polymers such as polyphenylenesulfide and polyethersulfone, polyurethanes, silicon containing polymers such as polydimethylsiloxane. In addition, the said structures can be made from copolymers, blends and/or laminates of the above materials, metal foils such as aluminum foil, metallized films and metals deposited on the above materials, as well as glass and ceramic materials.

In one such method, a laser, such as an excimer laser can be used to illuminate a photomask so that the light that passes through the photomask ablates an underlying material forming channels in the material substrate. Sercel, J., et al., SPIE Proceedings, Vol. 998, (September, 1988).

Generally, microfluidic devices can comprise an inlet port to which the test sample enters. Generally, the channels are capillaries and provide transport of the test sample from the inlet port into the device, an array of structures which provide a capture site, and a vent, such as an exit port, which vents gases. In addition, chambers and additional capillaries may be added when customizing the device. Generally, test sample moves through the device relying on capillary forces. In addition, one or more capillaries can be used to bring the test sample from the inlet port to the channels. Additionally, one or more capillaries can be used to exit the structures area of the device. However, differential pressure may be used to drive fluid flow in the devices in lieu of, or in addition to capillary forces.

Channels are created between adjacent structures through which fluid can flow. The channel and structure designs are important to optimize contact between the structure surfaces and fluid molecules. Typically, the depth of the channels range from about 1 micrometer (μm) to about 1 millimeter (μm). The average width of the channels typically ranges from about 0.02 μm to 20 μm. The channels may include structures of various shapes, including diamonds, hexagons, circles, or squares with height ranges typically from about 1 mu.m to 1 mm and the average width typically ranges from 1 μm to 1 mm.

Immobilization reagent can be covalently or non-covalently attached onto the surface of the structures as within the capillaries and/or chambers. The reagent can be a time-released reagent, spatially separated reagent, or coated and dried onto the surface. Such techniques of placing immobilization reagent on the surfaces are well known to those skilled in the art. In one embodiment, the immobilization reagents are antibodies disclosed herein which target influenza virus antigens (e.g., H5 AIV).

The methods for utilizing devices of the present invention involve using specific binding members. The methods of detection involve the binding of a colored label such as a fluorescent dye or a colored particle. Alternatively, detection may involve binding of an enzyme which can produce a colored product.

One or more alternate flow paths can be used in the devices of the present invention. The capillary branches into different pathways after transporting the test sample from the inlet port, the main pathway to the structures and the alternate pathways. The alternate pathways can allow the presence of multiple capture sites and allow simultaneous realizations of the presence or amount of multiple analytes in a single test site. In a preferred embodiment, the multiple analytes (different influenza subtypes) are determined in the test devices.

The alternate pathways can include areas for mixing test samples of the said kits. For example, chambers can be used as areas of reagent addition. In addition, trapping devices may be included in the device pathway so as to remove fluid constituents above a certain size. For example, the devices of the present invention can include a separator, e.g., to separate plasma or serum from whole blood. For example, a matrix of hydrophilic sintered porous permeable material can have a red blood cell agglutinating agent applied to its surface. The matrix could be placed in the device anterior to the structures. The red blood cells in the whole blood sample become entrapped in the interstices of the matrix while substantially blood cell free serum or plasma passes through the matrix and is transported by capillary action to the structures part of the device. U.S. Pat. No. 4,933,092 is hereby completely incorporated by reference.

Automation

The antibodies of this invention can be readily adapted to automated immunochemistry analyzers. To facilitate automation of the methods of this invention and to reduce the turnaround time, a capture antibody in an immunoassay of this invention needs to be coupled to magnetic particles.

Antibody is coupled to such magnetic beads by using available commercial technology as M-280 sheep anti-rabbit IgG coated Dynabeads from Dynal, Inc. [Lake Success, N.Y. (USA)] and rabbit antibody to a target protein, or by using M-450 Tosylactivated Dynabeads from Dynal, Inc. and covalently coupling a relevant antibody thereto. Alternatively, an agent such as glutaraldehyde could be used for covalently coupling a subject antibody to a solid support, preferably magnetic beads. Representative coupling agents can include organic compounds such as thioesters, carbodiimides, succinimide esters, diisocyanates, glutaraldehydes, diazobenzenes and hexamethylene diamines.

A preferred automated/immunoassay system is the ACS: 180® Automated Chemiluminescence System (Bayer Corporation; Tarrytown, N.Y. and Medfield, Mass. (USA); including ACS: 180 PLUS System; ACS: 180 SE System; and ACS: CENTAUR® System). For the ACS:180® Automated Immunoassay System, see Dudley, B. S., J. Clin. Immunoassay, 14 (2): 77 (Summer 1991). The system uses chemiluminescent labels as tracers and paramagnetic particles (PMP) as solid-phase reagents. The ACS: 180 system provides both competitive binding and sandwich-type assays, wherein each of the steps are automated. The ACS: 180 system uses micron-sized paramagnetic particles that maximize the available surface area, and provide a means of rapid magnetic separation of bound tracer from unbound tracer without centrifugation. Reagents can be added simultaneously or sequentially. Other tags, such as an enzymatic tag, can be used in place of a chemiluminescent label, such as, acridinium ester. Luminescent signals would preferably be detected by a luminometer. Preferably use the Bayer Immuno 1™ Immunoassay System. Other exemplary automated devices that can be adapted to perform immunoassays utilizing antibodies of the present invention, include U.S. Pat. Nos. 5,807,522 and 6,907,722.

In another embodiment, anti-influenza antibodies of the invention can be incorporated into an automated multi-well platform to utilize immunoassay methods. The multi-well assay modules (e.g., plates) are adapted for induced chemical luminescence-based assays inside one or more wells or chambers of a multi-well assay module (e.g., the wells of a multi-well assay plate). Multi-well assay plates may include several elements including, for example, a plate top, a plate bottom, wells, working electrodes, counter electrodes, reference electrodes, dielectric materials, contact surfaces for electrical connections, conductive through-holes electrically connecting the electrodes and contact surfaces, adhesives, assay reagents, and identifying markings or labels. The wells of the plates may be openings in the plate top; the inner walls of the openings may be the walls of the well. The plate bottom can be affixed to the plate top (either directly or aided by other components) and can serve as the bottom of the well.

The multi-well assay modules (e.g., plates) may have any number of wells and/or chambers of any size or shape, arranged in any pattern or configuration, and be composed of a variety of different materials. In a preferred embodiment of the invention, the multi-well assay plates are multi-well plates that use industry standard formats for the number, size, shape and configuration of the plate and wells. Examples of standard formats include 96-, 384-, 1536- and 9600-well plates, with the wells configured in two-dimensional arrays. Other formats include single well, two well, six well and twenty-four well and 6144 well plates. Preferably, the wells and/or chambers have at least one first electrode incorporated therein, and more preferably include at least one second electrode. According to preferred embodiments, the wells and/or chambers have at least one working electrode incorporated therein, and more preferably also include at least one counter electrode. According to a particularly preferred embodiment, working, counter and, optionally, reference electrodes are incorporated into the wells and/or chambers. The assay plates are preferably flat, but may also be curved (not flat).

Moreover, one or more assay reagents may be included in wells, chambers and/or assay domains of an assay module (e.g., in the wells of a multi-well assay plate). For example, assay reagents including antibodies to different influenza virus or different epitopes of an influenza virus polypeptide can be utilized in different regions of the micro-titer palte(s). These assay reagents may be immobilized or placed on one or more wells and/or chambers surfaces (preferably on the surface of an electrode, most preferably a working electrode) and may be immobilized or placed in one or more assay domains (e.g. reagents in patterned arrays are immobilized on one or more surfaces of a well and/or chamber, preferably on the surfaces of working electrodes and/or counter electrodes, most preferably on working electrode surfaces). The assay reagents may also be contained or localized within a well and/or chamber by its outline. For example, patterned dielectric materials may confine or localize fluids.

In one embodiment, an apparatus of the invention can be used to induce and measure luminescence in assay modules, preferably in multi-well assay plates. It may incorporate, for example, one or more photodetectors; a light tight enclosure; electrical connectors for contacting the assay modules; mechanisms to transport multi-well assay modules into and out of the apparatus (and in particular, into and out of light tight enclosures); mechanisms to align and orient multi-well assay modules with the photodetector(s) and with electrical contacts; mechanisms to track and identify modules (e.g. one or more bar code readers (e.g., one bar code reader for reading one side of a plate or module and another for reading another side of the plate or module); orientation sensor(s); mechanisms that make electrical connections to modules, one or more sources of electrical energy for inducing luminescence in the modules; and appropriate electronics and software.

The apparatus may also include mechanisms to store, stack, move and/or distribute one or more assay modules (e.g. multi-well plate stackers). The apparatus may advantageously use arrays of photodetectors (e.g. arrays of photodiodes) or imaging photodetectors (e.g. CCD cameras) to measure luminescence. These detectors allow the apparatus to measure the light from multiple wells (and/or chambers) simultaneously and/or to image the intensity and spatial distribution of light emitted from an individual well (and/or chamber).

Preferably, the apparatus can measure light from one or more sectors of an assay module, preferred assay module is a multi-well assay plate. In some embodiments, a sector comprises a group of wells (and/or chambers) numbering between one and a number fewer than the total number of wells (and/or chambers) in the assay module (e.g. a row, column, or two-dimensional sub-array of wells in a multi-well plate). In a preferred embodiment, a sector comprises between 4 percent and 50 percent of the wells of a multi-well plate. In a especially preferred embodiment, multi-well assay plates are divided into columnar sectors (each sector having one row or column of wells) or square sectors (e.g., a standard sized multi-well plate is divided into six square sectors of equal size). In some embodiments, a sector comprises one or more wells with more than one fluid containment region within the wells. The apparatus, preferably, can sequentially induce ECL and/or sequentially measure ECL from the sectors in a given module (preferably plate).

The apparatus may also incorporate microprocessors and computers to control certain functions within the instrument and to aid in the storage, analysis and presentation of data. These microprocessors and computers may reside in the apparatus, or may reside in remote locations that is connected with the apparatus (e.g. through network connections).

Membranes/Surfaces

In various aspects of the present invention, devices incorporating influenza virus antigens or anti-influenza virus antibodies comprise a surface or membrane. Various surfaces or membranes can provide a surface for various conventional immunoassay devices, onto which an antibody or antigen is immobilized or disposed. As such, membranes can provide regions comprising test as well as control regions that utilize immunoreagents allowing visualization of a test result (e.g., whether a sample contains one or more viruses). In various embodiments, membranes having influenza virus antigens or anti-influenza virus antibodies disposed thereon are in turn disposed onto a solid substrate (e.g., lateral flow or dipstick device).

The membrane or surface to which antigen/antibody can be attached comprises of a material including but not limited to cellulose, nitrocellulose, nylon, cationized nylon carrying a quaternary amino charge (Zeta probe), aminophenylthioether (APT) paper which is converted to DPT, the diazo derivative (this cannot be stained when used with enzyme detectable labels) or hydrophilic polyvinylidene difluoride (PVDF) (available from Millipore, Billerica, Mass.). The term “nitrocellulose” refers to any nitric acid ester of cellulose. Thus suitable materials may include nitrocellulose in combination with carboxylic acid esters of cellulose. The pore size of nitrocellulose membranes may vary widely, but is frequently within about 5 to 20 microns, preferably about 8 to 15 microns. However, it can be expected by those skilled in the art that other well-known materials can also be used. In some embodiments, the test region comprises a nitrocellulose web assembly made of Millipore nitrocellulose roll laminated to a clear Mylar backing. In another embodiment, the region comprising antigen/antibody (or “test region”) is made of nylon. In another embodiment, the test region is comprised of particles that can immobilize latex or other particles which can carry another reagent capable of binding specifically to an analyte, thereby defining a test zone, for example, compressed nylon powder, or glass fiber. In some embodiments, the test region is comprised of a material that is opaque when in a dry state, and transparent when in a moistened state.

Test and Control Zones

Devices can include membranes/surfaces comprising test and control zones. The test region can be constructed from any of the materials as listed above. Often the test and control zones can define the components of the test region. In one embodiment, the test and control zones are comprised of the same material as the test region. Frequently, the term “test region” is utilized herein to explain a region in/on a device that comprises at least one test and control zone. In some embodiments the device utilizes a bibulous material but in some embodiments to provide non-bibulous flow, these materials need to be treated with blocking agents that can block the forces which account for the bibulous nature of bibulous membranes. Suitable blocking agents include bovine serum albumin, methylated bovine serum albumin, whole animal serum, casein, and non-fat dry milk, a number of detergents and polymers, e.g., PEG, PVA and the like. In some embodiments, the interfering sites on the untreated bibulous membranes are completely blocked because of the presence of the blocking agent to permit non-bibulous flow to pass through. As indicated herein, the test device of the present invention is a device with multiple test and control zones.

The test region generally includes one or more control zones, this is very useful for verifying whether the sample flow is as expected. Each of the control zones comprises a spatially distinct region that often includes an immobilized member of a specific binding pair which can react with a labeled control reagent. In some embodiments, the procedural control zone contains an authentic sample of the analyte of interest, or a fragment thereof. In this embodiment, one type of labeled reagent is utilized, wherein the fluid sample carries the labeled reagent to the test and control zones; and the labeled reagent not bound to an analyte of interest will then bind to the authentic sample of the analyte of interest positioned in the control zone. In another embodiment, the control line contains antibody that is specific for the labeled reagent, or is provided for immobilized labeled reagent. In operation, a labeled reagent is restrained in each of the one or more control zones, even when any or all the analytes of interest are absent from the test sample.

In some embodiments, solid supports comprises patterned regions comprising antigen/antibody-binding matrix areas, which can be designed in any shape desired (e.g., square, oval, circle, vertical or horizontal lines). For example, the antigen-binding matrix areas are disposed onto a solid support dipstick which may be made of materials such as plastic or Mylar. Through the use of this invention, it is possible to detect multiple anti H5 AIV antibody subtypes in a single test through the incorporation of multiple matrix squares each containing different specific antigens at various positions on a single test strip, or on a single solid phase support dipstick.

In various embodiments, a device comprising antibodies of the invention and is utilized in an immunoassay can be included in a kit. The kit contains the necessary reagents for the immunoassay utilization of particular format. The kit contains a dipstick and separate reagents utilized therewith, a lateral flow device on which is immobilized the antibodies necessary for the assay of multiple subtypes of influenza, or any conventional device with the necessary reagents. For example, through a process of frequently dipping the dipstick through the series of reagents provided in the kit the presence or absence of particular anti-subtype influenza virus (e.g., H5 AIV antibody) or influenza virus antigen (e.g., H5 antigen) in a sample can be simply and quickly ascertained. Such kits would be suitable for use by experts and professionals. Using the kit of the present invention can permit the rapid serologic diagnosis of influenza virus (e.g., AIV) obtained from body fluids such as blood, urine, sputum, semen, feces, saliva, bile, cerebral fluid, nasal swab, urogenital swab, nasal aspirate, spinal fluid, etc.

In another embodiment, a solid phase support dipstick or lateral flow device is placed in a test tube or similar receptacle to which is added the specimen sample from the patient or animal suspected to be infected with influenza virus (e.g., AIV). The specimen sample reacts with antigens/antibodies bound on the dipstick. The dipstick is then removed and gently washed. The solid phase support dipstick is removed from the wash solution and placed in another tube containing highly diluted, affinity purified immunoglobulin, which is specific for the species that the sample was obtained from, and can conjugate to alkaline phosphatase or other suitable enzymes. The dipstick is then removed from the second-antibody solution and placed in a container of wash solution. Upon removal from the wash solution the dipstick is placed in a final tube of premixed chromogen solution or other suitable substrate solution. A positive reaction can be assessed by simple visual comparison of the control (upper line) with the positive line (lower line). If the positive line is darker than the control, then the test result is positive. The enzymes which are covalently bound to the affinity purified immunoglobulin react with substrates which yield a color reaction product at the end of the enzyme-substrate reaction. In this way the presence of bound affinity purified immunoglobulin can be readily detected thereby indicating the presence of antibodies in the specimen sample that are specific for influenza virus (e.g., H5 antibody). The technology incorporates the known ELISA techniques, as also disclosed herein.

It should be understood that techniques of selecting appropriate enzymes and substrates and the appropriate reaction conditions are known to one skilled in the art. These enzymes remain active after being conjugated to immunoglobulin molecules. Each chemical reaction of enzyme-substrate pair generates a colored product. In addition there are multiple alternative ways of paring in which the enzyme and substrate can both conjugate with the affinity purified immunoglobulin but the enzyme and substrate only react to form the colored reaction product after the affinity purified immunoglobulin has bound to the specimen antibody.

Of course, by utilizing different antibodies/antigens a sample can be readily screened for a panel of different virus types or subtypes. One of skill in art should understand that a variety of panels need to be assayed via the immunoassays described herein. See CURRENT PROTOCOLS IN IMMUNOLOGY (Coligan, John E. et. al., eds. 1999).

Arrays

Antibodies of the present invention can be readily adapted for use in devices adapted for rapid methods of detecting analytes, including detection of one or more influenza virus proteins (e.g., H5) or of one or more anti-influenza virus antibodies in a sample. Such methods include embodiments wherein antibodies are displayed in an array format that contains other antibodies, which target multiple different viruses such as other influenza subtypes (e.g., AIV). In other embodiments, antibodies can target the same antigen or specifically bind a different epitope on a given polyeptide.

In a further embodiment of the present invention, the array of antibodies comprises a substrate, and a plurality of patches arranged in discrete, known regions on the portions of the substrate surface wherein (i) each patch comprises antibodies immobilized on the substrate, wherein said antibodies of a given patch are capable of binding a particular viral expression product, fragment thereof, or host protein, such as an anti-viral antibody and (ii) the array comprises a plurality of different antibodies, each of which is capable of binding a different viral expression product, fragment thereof, or host protein, such as an anti-viral antibody.

The antibodies are preferably covalently immobilized on the patches of the array, either directly or indirectly. In most cases, the array comprises at least ten patches. In a preferred embodiment, the array comprises at least 50 patches. In a particularly preferred embodiment the array comprises at least 100 patches. In an alternative preferred embodiment, the array of antibodies may comprise more than $10^3$, $10^4$ or $10^5$ patches.

The area of substrate surface covered by each of the patches is preferably no more than 0.25 $mm^2$. Preferably, the area of the substrate surface covered by each of the patches is between 1 $\mu m^2$ and 1000 $\mu m^2$. In a particularly preferred embodiment, each patch covers an area of the substrate surface from 1 $\mu m^2$ to 2,500 $\mu m^2$. In an alternative embodiment, a patch on the array may cover an area of the substrate surface as small as 2,500 $nm^2$, although patches of such small size are generally not necessary in the use of the array.

The patches of the array may be of any geometric shape. For instance, the patches may be rectangular or circular. The patches of the array may also be of irregular shapes. The patches can also be elevated optionally from the median plan of the underlying substrate.

The distance separating the patches of the array can vary. Preferably, the distance between neighboring patches on the array is from about 1 μm to 500 μm. Typically, the distance separating the patches is roughly proportional to the diameter or side length of the patches on the array if the patches have diameters greater than 10 μm. If the patch size is relatively small, then the distance separating the patches is generally larger than the diameters of the patch.

In a particular embodiment of the array, all patches of the array are contained within an area of about 1 $cm^2$ or less on the surface of the substrate. In one preferred embodiment of the array, therefore, the array comprises 100 or more patches within a total area of about 1 $cm^2$ or less on the surface of the substrate. Alternatively, a particularly preferred array comprises $10^3$ or more patches within a total area of about 1 $cm^2$ or less. A preferred array may even optionally comprise $10^4$ or $10^5$ or more patches within an area of about 1 $cm^2$ or less on the surface of the substrate. In other embodiments of the present invention, all of the patches of the array are contained within an area of about 1 $mm^2$ or less on the surface of the substrate.

Typically, only one antibody is present on a single patch of the array. If more than one antibody is present on a single patch, then all of the antibodies on that patch must share a common binding partner. For instance, a patch may comprise a variety of antibodies to the influenza viral protein (although, potentially, the antibodies may bind different epitopes on a given influenza virus). In preferred embodiments, the influenza viral protein/antigen is H5 and the influenza virus is AIV.

The arrays of the invention can have any number of different antibodies. Typically the array comprises at least ten different antibodies. Preferably, the array comprises at least 50 different antibodies. More preferably, the array comprises at least 100 antibodies. Alternative preferred arrays comprise more than $10^3$ different antibodies or more than $10^4$ different antibodies. The array may even optionally comprise more than $10^5$ different antibodies.

In one embodiment of the array, each of the patches of the array comprises a different antibody. For instance, an array comprising about 100 patches could comprise about 100 different antibodies. Likewise, an array of about 10,000 patches could comprise about 10,000 different antibodies. In an alternative embodiment, however, each different antibody is immobilized on more than one separate patch on the array. For instance, each different antibody may optionally be present on two to six different patches. An array of the invention, therefore, may comprise about three-thousand antibody patches, but only comprise about one thousand different antibodies since each different antibody is present on three different patches.

Typically, the number of different proteins which can be bound by the plurality of different antibodies on the array is at least ten. However, it is preferred that the plurality of different antibodies on the array is capable of binding a large number of different proteins, such as at least about 50 or at least about 100. In further preferred embodiments, the plurality of different antibodies on the array is capable of binding at least about $10^3$ proteins.

Use of the antibody arrays of this embodiment may optionally involve placing the two-dimensional array in a flow chamber with approximately 1-10 μl of fluid volume per 25 $mm^2$ overall surface area. The cover over the array in the flow chamber can be transparent or translucent. In one embodiment, the cover may comprise Pyrex or quartz glass. In other embodiments, the cover may be part of a detection system that monitors interaction between the antibodies immobilized on the array and protein in a solution such as a cellular extract. The flow chambers should remain filled with appropriate aqueous solutions to preserve antibody. Salt, temperature, and other conditions are preferably kept similar to those of normal physiological conditions. Samples in a fluid solution may be mixed into the flow chamber to surely interact with the immobilized antibodies. Sufficient time must be given to allow for binding between the antibodies and their binding partners to occur. The amount of time required for this depends upon the affinity of the antibodies for their binding partners. No specialized microfluidic pumps, valves, or mixing techniques are required for fluid delivery to the array.

Detection Means

As applicable to any device utilizing antibodies of the preset invention, a wide range of detection components are available for detecting the presence of binding partners. Detection may be either quantitative or qualitative. The invention array can be interfaced with optical detection methods such as absorption in the visible or ultraviolet range, chemoluminescence, and fluorescence (including lifetime, polarization, fluorescence correlation spectroscopy (FCS), and fluorescence-resonance energy transfer (FRET)). Furthermore, other modes of detection such as those based on optical waveguides see PCT Publication (WO 96/26432 and U.S. Pat. No. 5,677,196), surface plasmon resonance, surface charge sensors, and surface force sensors are compatible with many embodiments of the invention. Alternatively, technologies such as those based on Brewster Angle microscopy (BAM) (Schaaf et al., Langmuir, 3:1131-1135 (1987)) and ellipsometry (U.S. Pat. Nos. 5,141,311 and 5,116,121; Kim, Macromolecules, 22:2682-2685 (1984)) could be applied. Quartz crystal microbalances and desorption processes (see for example, U.S. Pat. No. 5,719,060) also provide other alternative detection means suitable for some embodiments of the invention array. An optical biosensor system compatible both with some arrays of the present invention and a variety of non-label detection methods such as surface plasmon resonance, total internal reflection fluorescence (TIRF), Brewster Angle microscopy, optical waveguide light mode spectroscopy (OWLS) can be found in U.S. Pat. No. 5,313,264.

In some embodiments, the devices incorporating the antibodies of the invention can be incorporated into a system which includes a reader, particularly a reader built in a computer, such as a reflectance and/or fluorescent based reader, and data processing software employing data reduction and curve fitting algorithms, preferably in combination with a trained neural network for accurately determining the presence and concentration of analyte in a biological sample. As used herein, a reader refers to an instrument for detecting and/or quantitating data, such as on test strips comprised in a test device utilizing antibodies of the present invention. The data shall be visible to the naked eye, but does not need to be. The methods include the steps of performing an immunoassay on a patient sample, reading the data using a reflectance and/or fluorescent based reader and processing the resultant data using data processing software employing data reduction. Preferred software includes curve fitting algorithms, optionally in combination with a trained neural network, to determine the presence and concentration of analyte in a given sample. The data obtained from the reader then can be further processed by the medical diagnosis system that processes and outputs data to provide a risk assessment or diagnosis of a medical condition. In alternative embodiments, the output data can be used as input into a subsequent decision support system, such as a neural network, that can be trained to evaluate such data.

In various embodiments, the reader can be a reflectance, transmission, fluorescence, chemo-bioluminescence, magnetic or amperometry reader (or combinations of two or more), depending on the signal that is to be detected from the device. Furthermore, some of the detection methods commonly used for traditional immunoassays which require the use of labels may be applied to the arrays of the present invention. These techniques include noncompetitive immunoassays, competitive immunoassays, dual label, ratiometric immunoassays. These particular techniques are primarily suitable for use with the arrays of antibodies when the number of different antibodies with different specificity is small (roughly less than 100). In the competitive method, binding-site occupancy is determined indirectly. In this method, the antibodies of the array are exposed in a labeled developing agent, which is generally a labeled analyte or an analyte analog. The developing agent competes for the binding sites on the antibodies with the analyte. The binding of the developing agent to the antibodies of the individual patches can form a small fraction of occupancy of the antibodies on different-patches.

In the noncompetitive method, binding site occupancy is determined directly. In this method, the patches of the array are exposed in a labeled developing agent capable of binding to either the bound analyte or the occupied binding sites on the protein-capture agent. For instance, the developing agent may be a labeled antibody directed against occupied sites (ie., a "sandwich assay"). Alternatively, a dual label, the ratiometric approach is taken where the antibody is labeled with one label and the developing agent is labeled with a second label (Ekins, et al., Clinica Chimica Acta., 194:91-114, 1990). Many different labeling methods may be used in the aforementioned techniques, including radioisotopic, enzymatic, chemiluminescent, and fluorescent methods. In some embodiments, fluorescent detection methods are preferred. Methods of detection include, but are not limited to, changes in color, light absorption, or light transmission, pH, conductivity, fluorescence, change in physical phase or the like.

Test samples shall provide a detectable component of the detection system, or such components may be added. The components will vary widely depending on the nature of the detection system. One such detection method involves the use of particles, where particles provide for light scatter or a change in the rate of flow. Particles may be, but are not limited to, cells, polymeric particles which are immiscible with a liquid system, latex particles, ceramic particles, nucleic acid particles, agglutinated particles or the like. The choice of particles will depend on the method of detection, the dispersability or the stability of the dispersion, inertness, participation in the change of flow, or the like. The binding of an analyte to a specific binding member at the capture site can be optionally detected through the pressure of the test sample in the device. For example, a pressure detector connected to the test sample entering and exiting the channel will allow the detection of pressure decreases caused by analyte binding which results in the slowdown of channel flow.

For example, for quantifying the amount of detectable label present (e.g., antibody-conjugate), and the amount of antigen present, the procedure and apparatus of Hazelgrove et al. may be used (see Anal. Biochem 150:449-456, 1985). This procedure is based on a TV camera linked to a computer. The labels are displayed on a luminescent box imaged by the TV camera, and digitized with a digitizing board (Techmar, Inc.). After digitizing, the computer will readout the position, width, height and relative area of each label. Optical density (OD) measurements are also used to measure absolute protein concentrations.

In another embodiment a device incorporating a Dot-ELISA test is used to detect a target protein directly from any sample. Therefore, antibodies of the present invention can be utilized in a process comprising the following steps:

(a) providing a solid support for performing an assay of monoclonal antibody;

(b) applying to the solid support a sample suspected of containing an influenza virus;

(c) applying to the solid support a solution containing an organic acid, such as citric or lactic acid;

(d) applying to the solid support a solution containing a mucolytic agent and a detergent;

(e) contacting the solid support with a primary MAb, chimeric MAb, a variant or fragment thereof for a time sufficient to allow the MAb, chimeric MAb, variant or fragment and an H5 AIV protein to bind together to form an antigen-bound primary MAb;

(f) contacting the above with an enzyme labeled anti-MAb conjugate for a time sufficient to facilitate binding of the antigen-bound MAb to the conjugate; and (g) applying a color reagent to the solid support, wherein the color reagent is catalyzed by the enzyme to develop a colored marking that allows visual detection of the presence of an H5 AIV protein in the sample.

A Dot-ELISA method is disclosed in U.S. patent application 2006/0246429, which is incorporated here in its entirety as comparing reference.

In some embodiments a device or kit of the present invention can be utilized in the field of care setting, where a chromogenic detection system, such as a system employing alkaline phosphatase may be used. For example, separate vials containing streptavidin-alkaline phosphatase conjugate in buffer, nitroblue tetrazolium (NBT), or 5-bromo-4-chloro-3-indolyl phosphate (BCIP), which are designed to be used in sequence to achieve the desired color may be supplied as components of a kit. With chromogenic detection systems results can be visualized by eye without the aid of any equipment. In one embodiment, a device can utilize alkaline phosphatase to quantitate the amount of AIV present. Such a device comprising alkaline phosphatase can give accurate quantitative results when used in conjunction with a densitometer.

In one embodiment, a kit for the detection of an H5 AIV protein or an anti-subtype H5 AIV antibody, may comprise a detectable label such as streptavidin-alkaline phosphatase conjugate bound thereon; a reagent comprising NBT or 5-bromo-4-chloro-3-indolyl phosphate (BCIP); and a reference standard.

In any of the embodiments disclosed herein, the test sample may be derived from a source such as, but is not limited to, a physiological source. Test samples that can be administered to devices of the present invention include samples suspected of containing an antigen or antibody, which may be obtained from a non-human animal or a human subject, and include but are not limited to physiological fluids such as blood, serum, plasma, saliva, ocular lens fluid, cerebral spinal fluid, pus, exudate, milk, sweat, tears, ear flow, sputum, lymph, urine, egesta, secretion from oral or nasal cavities, tissues such as lung, spleen and kidneys, the liquid of the complete virus or lytic virus from chicken embryo culture, and other samples suspected of containing an influenza virus protein or anti-influenza virus antibodies which are soluble or may be suspended in a suitable fluid. The test sample may be subject to prior treatment such as, extraction, addition, separation, dilution, concentration, filtration, distillation, dialysis or the like. Besides physiological fluids, other liquid test samples may be employed and the components of interest may be either liquids or solids as long as the solids are dissolved or suspended in a liquid medium. In one embodiment, a sample is taken from the nasal cavity. Devices of the present invention often contain a surface to which one or more antigens or antibodies can be attached.

Treatment Methods and Pharmaceutical Compositions

The present invention provides a method of preventing or treating patients infected with viruses associated with avian influenza virus in a subject comprising administering to said subject a pharmaceutically effective amount of the pharmaceutical composition comprising one or more monoclonal antibodies of the present invention. The present invention also provides a pharmaceutical composition comprising one or more monoclonal antibodies of the present invention or a salt pharmaceutical thereof.

The pharmaceutical composition of the present invention may be administered to a subject through conventional administration routes, including without limitation, the oral, buccal, sublingual, ocular, topical, parenteral, rectal, intracisternal, intravaginal, intraperitoneal, intravesical, local (e.g., powder, ointment, or drop), or nasal routes.

Pharmaceutical compositions suitable for injection of ex-intestine and ex-stomach may comprise pharmaceutically acceptable sterile aqueous or nonaqueous solutions, dispersions, suspensions, or emulsions, and sterile powders for extemporaneous reconstitution into injectable solutions or dispersions. For example, suitable aqueous and nonaqueous carriers, vehicles, and various diluents such as water, ethanol, polyols (such as propylene glycol, polyethylene glycol, glycerol, and the like), suitable mixtures thereof, vegetable oils (such as olive oil), and injectable organic esters such as ethyl oleate. Proper fluidity can be maintained, for example, by the use of a lecithin coatin. Appropriate particle size is maintained, for example, by the use of dispersions and surfactants.

The pharmaceutical compositions of the invention may further comprise adjuvants, such as preserving, wetting, emulsifying, and dispersing agents. To prevent microorganism contamination, the compositions may also comprise instant components such as various antibacterial and antifungal agents, for example, parabens, chlorobutanol, phenol, sorbic acid, and the like. It may also comprise isotonic agents, for example, sugars, sodium chloride, and the like. Prolonged absorption of injectable pharmaceutical compositions may be achieved by the use of agents capable of delaying absorption, such as aluminum monostearate and gelatin and the like.

Solid dosage forms for oral administration include capsules, tablets, powders, and granules etc. In such solid dosage forms, the active compound is admixed with at least one conventional inert pharmaceutical excipient (or carrier) such as sodium citrate or dicalcium phosphate, or (a) fillers or extenders, such as starches, lactose, sucrose, mannitol, and silicic acid; (b) binders, such as carboxymethyl-cellulose, alginates, gelatin, polyvinylpyrrolidone, sucrose, and acacia; (c) humectants, such as glycerol; (d) disintegrating agents, such as agar, calcium carbonate, potato or tapioca powder; (e) solution retarders, such as paraffin; (f) absorption accelerators, such as quaternary ammonium mixtures; (g) wetting agents, such as cetyl alcohol and glycerol monostearate; (h) adsorbents, such as kaolin and bentonite; (i) lubricants, such as talc, calcium stearate, magnesium stearate, solid polyethylene glycols, sodium lauryl sulfate, or mixtures thereof. In the case of capsules and tablets, the buffering agents may further be comprised.

Solid dosage forms may be formulated as ameliorated release and pulsatile release dosage forms containing excipients such as those detailed above for immediate release dosage forms together with additional excipients that act as release rate modifiers, these being coated on included in the dosage forms. Release rate modifiers include hydroxypropylmethyl cellulose, methyl cellulose, sodium carboxymethylcellulose, ethyl cellulose, cellulose acetate, polyethylene oxide, xanthan gum, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Ameliorated release and pulsatile release dosage forms may contain one or a combination of release rate improving excipients.

The pharmaceutical compositions of the present invention may further comprise fast dispersing or dissolving dosage formulations (FDDFs) containing the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e., where the drug substance is insoluble, a fast dispersing dosage form may be prepared, and where the drug substance is soluble, a fast dissolving dosage form may be prepared.

Solid compositions of a similar type may also be employed as fillers of soft or hard gelatin using such excipients as lactose or milk sugar, or other high molecular weight polyethylene glycols, and the like.

Solid dosage forms such as tablets, dragees, capsules, and granules can be prepared with coatings and shells, such as enteric coatings and others well-known to one of ordinary skill in the art. They may also comprise opacifying agents, and can also be of similar composition that they release the active compound(s) in a delayed, sustained, or controlled manner. Compositions that can be employed for embedding are polymeric substances and waxes etc. The active compound(s) can also be in micro-encapsulated form, if appropriate, with one or more of the above-mentioned excipients.

Liquid dosage forms for oral administration include pharmaceutically acceptable emulsions, solutions, suspensions, syrups, and elixirs etc. In addition to the active compounds, the liquid dosage form may also contain inert diluents commonly used in the art, such as water or other solvents, soluble agents and emulsifiers, as for example, ethyl alcohol, isopropyl alcohol, ethyl carbonate, benzyl benzoate, propylene glycol, 1,3-butylene glycol, oils, in particular, cottonseed oil, groundnut oil, corn oil, olive oil, castor oil, and sesame oil, glycerol, tetrahydrofurfuryl alcohol, polyethylene glycols and fatty acid esters of sorbitan, and mixtures of these substances, and the like.

Besides such inert diluents, the pharmaceutical composition can also include adjuvants, such as wetting agents, emulsifying and suspending agents, sweetening, flavoring, and perfuming agents. The pharmaceutical composition may further include suspending agents, such as ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Pharmaceutical composition of the present invention is also made as a mixture, a veterinarily acceptable salt thereof, or veterinarily acceptable solvate or pro-drug thereof for treatments in veterinary use. And it is made as a suitable formulation with the dosing regimen and route of administration most appropriate for a particular animal in accordance with normal veterinary practice and veterinary practitioner.

One or more monoclonal antibodies of this invention may be used in combination with other anti-viral agents for the prevention and/or treatment of diseases associated with H5 avian influenza virus infection. The monoclonal antibodies may be administered simultaneously, separately or sequentially with the other antiviral agents. Other antiviral agents include without limitation ribavirin, amantadine, hydroxyurea, IL-2, IL-12 and pentafuside Peptides Screening Methods and Peptides Recognized by the Antibodies and Vaccines The present invention provides a method of screening polypeptides that simulate the epitopes recognized by the monoclonal antibodies of the present invention. Furthermore, the present invention also provides polypeptides that simulate the epitopes recognized by the monoclonal antibodies of the present invention. In one aspect, the present invention discloses short peptides having the amino acid sequences set forth in SEQ ID Nos: 31-39. These polypeptides can bind to the monoclonal antibodies of the invention. These polypeptides may also be used to make a vaccine against the avian influenza virus subtype H5 and be used to diagnose the presence of anti-H5 hemagglutinin antibodies. These polypeptides may further be used for the screening and optimization evaluation of H5 subtype avian influenza adjuvant.

In another aspect, the screening method of the present invention comprises the following steps (i) culturing a polypeptide display library under conditions suitable for polypeptide expression; (ii) mixing the culture solution with monoclonal antibodies of the present invention; (iii) selecting the phage clones that specifically bind to said monoclonal antibodies. The monoclonal antibodies used for the screening are not limited to the monoclonal antibodies 8G9, 13D4 and 20A11. Examples 11 to 13 of this application describe in detail an assay that successfully screened short peptides that bind to the monoclonal antibodies of the invention using a phage display polypeptide libraries.

EXAMPLES

The present invention is further illustrated with the following examples and drawings, but these illustrations are not to be construed to limit the scope of the present invention.

Example 1

Preparation of Monoclonal Antibodies Against the HA Gene of Subtype H5 Avian Influenza Virus Preparation of Antigen.

Fertilized chicken embryos of 9 days old were inoculated with virus strain Ck/HK/Yu22/02 (H5N1) (referred to as "Yu22") for 2 days at 30° C. The chicken embryo supernatant was collected to obtain the amplified Yu22 virus. Live viruses were collected and inactivated with 0.03% formalin at 4° C. The HA of the inactivated virus was detected and the titer of the inactivated virus was measured (please refer to the guidelines of WHO for the specific methods for determining the HA titer and detecting hemagglutination inhibition (HI). We chose the virus strain HA=1024, which was provided by the Microbiology Department of Hong Kong University).

Mice.

6 weeks old female Balb/c mice were provided by the Experimental animal Center of School of Life Sciences, Xiamen University.

Production of Hybridoma.

We used standard in vivo immunization and PEG fusion methods to produce the monoclonal antibody. For details of the methods please refer to *Antibodies: A Laboratory Manual* (Ed Harlow et al., Cold Spring Harbor Laboratory, 1988). The method was briefly described below.

Immunization of Mice. The above mentioned pre-treated virus supernatant was mixed and emulsified with Complete Freund's adjuvant (CFA) in equal volume. The mixture was injected at multiple points of the muscles on the four legs of the mice at the dosage of 300 μl per mouse per injection. The same dosage of virus supernatant with Incomplete Freund's adjuvant was injected as boosters on the 15th and 29th day after the first immunization respectively. After the second booster, blood sample was taken from the mice to determine the inhibition potency by hemagglutination inhibition assay. When the potency reached 1:640, the mouse spleen was taken to carry out the fusion experiment. Another booster was injected 72 hr before the fusion experiment at the dosage of 50 μl per mouse through the caudal vein. 10 fusion plates were produced.

Fusion: The mouse spleen cell with the highest HI titer was fused with the mouse myeloma cells. First, the spleen was grinded to obtain the spleen cell suspension, which was then fused with SP2/0 mouse myeloma cells in log phase growth, the cell number of the myeloma cells is 10 times less than that of the spleen cells. The cells were fused together at the presence of PEG1500 for 1 minute. Then 100 ml of the fused cell solution was cultured in 10 96-well plates. The fusion medium was the RPMI1640 complete selection medium containing HAT and 20% FBS. The clones having the desired antigen specificity were screened by hemagglutination inhibition (HI) test, and stable monoclonal antibody producing cell lines were obtained after three rounds of cloning.

Screening of hybridoma: The fused cells were cultured on a 96-well cell plate for 10 days. The cell supernatant was extracted to do hemagglutination inhibition (HI) test. The wells containing positive clones were further cloned till the antibodies secreted by the cell line could stably inhibit agglutination between Yu22 virus strain and chicken blood.

Screening result: Three monoclonal antibody cell lines, 8G9, 13D4 and 20A11 were obtained.

Culture of hybridoma: Stable hybridoma monoclonal antibody cell lines were cultured first in a $CO_2$ incubator using 96-well plates, then transferred to 24-well plates, then transferred to a 50 ml cell culture flask for further amplification. The cells in the culture flask were then collected and injected into a mouse abdominal cavity. Ascitic fluid was extracted from the mouse abdominal cavity after 7-10 days.

Purification of Monoclonal Antibodies.

The ascetic fluid was first precipitated with 50% ammonium sulfate, then dialyzed with PBS at pH 7.2, purified with DEAE column by HPLC to obtain the purified monoclonal antibodies. The purity of the purified monoclonal antibody was determined with SDS-PAGE.

Hemagglutination inhibition assay activity test of the monoclonal antibodies

Fifteen strains of H5N1 viruses from Vietnam, Indonesia, Malaysia, Thailand, Hong Kong, China and Europe etc. that belong to different virus subtypes (Chen et al. PNAS, 103: 2845 (2006)) and 14 strains of non-H5 viruses (H1~H13, Chicken NDV) were chosen to test the reactivity of the selected monoclonal antibodies with viruses using the hemagglutination inhibition (HI) assay. The results were shown in Tables 1 and 2. The results showed that all three strains of the monoclonal antibodies had good specificity, and they didn't react with the non-H5 viruses. And for reactions with the H5 virus strains, all three strains of the monoclonal antibodies can react with all virus strains, showing excellent reaction spectra.

TABLE 1

Positive reaction rates between monoclonal antibodies and H5 or non-H5 virus strains using the hemagglutination inhibition assay

| Monoclonal antibody | Antibody subtype | H5 virus strain (Positive number/total virus number) | Non-H5 virus strain (Positive number/total virus number) |
|---|---|---|---|
| 8G9 | IgG2b | 15/15 | 0/14 |
| 13D4 | IgG2a | 15/15 | 0/14 |
| 20A11 | IgG2a | 15/15 | 0/14 |

TABLE 2

Hemagglutination Inhibition Titer of Monoclonal Antibodies for 15 H5 Virus Strains

| | Hamaglutinin inhibition titer | | |
|---|---|---|---|
| H5N1 strains | 8G9 | 13D4 | 20A11 |
| GD1.1 | 12800 | 6400 | 12800 |
| GD3.1 | 12800 | 12800 | 12800 |
| GD4.1 | 12800 | 12800 | 12800 |
| IDN1.1 | 12800 | 12800 | 12800 |
| IDN3.1 | 12800 | 12800 | 12800 |
| IDN6.1 | 12800 | 12800 | 12800 |
| IDN8.1 | 12800 | 12800 | 12800 |
| VTM1.1 | 12800 | 6400 | 12800 |
| VTM4.1 | 12800 | 12800 | 12800 |
| VNM2-2.1 | 12800 | 12800 | 12800 |
| YN2.1 | 12800 | 12800 | 12800 |
| HN3.1 | 12800 | 12800 | 12800 |
| QH1.1 | 12800 | 12800 | 12800 |
| Mixed1.1 | 12800 | 6400 | 12800 |
| FJ1.5 | 12800 | 12800 | 12800 |

Neutralization test between monoclonal antibodies and viruses

The neutralization activities of the above mentioned monoclonal antibodies with 15 strains of different sublineages of H5N1 viruses were detected by the micro-well neutralization test (Hulse-Post et al. PNAS, 102:10682-7, (2005)), the results in Table 3 demonstrated that three strains of monoclonal antibody had good neutralization activities against all H5N1 virus strains.

TABLE 3

Neutralization test titer of monoclonal antibody for the H5N1virus

| | Neutralization titer | | |
|---|---|---|---|
| H5N1 strains | 8G9 | 13D4 | 20A11 |
| GD1.1 | 12800 | 12800 | 12800 |
| GD3.1 | 12800 | 12800 | 12800 |
| GD4.1 | 12800 | 12800 | 12800 |
| IDN1.1 | 12800 | 12800 | 12800 |
| IDN3.1 | 12800 | 12800 | 12800 |
| IDN6.1 | 12800 | 12800 | 12800 |
| IDN8.1 | 12800 | 12800 | 12800 |
| VTM1.1 | 12800 | 12800 | 12800 |
| VTM4.1 | 12800 | 12800 | 12800 |
| VNM2-2.1 | 12800 | 12800 | 12800 |
| YN2.1 | 12800 | 12800 | 12800 |
| HN3.1 | 12800 | 12800 | 6400 |
| QH1.1 | 12800 | 12800 | 12800 |
| Mixed1.1 | 12800 | 12800 | 12800 |
| FJ1.5 | 12800 | 12800 | 12800 |

Example 2

Feasibility Experiment of the Antiviral Therapy of Monoclonal Antibodies

Treatment of infectious diseases using antibodies by passive immunization is a potentially effective anti-viral therapeutic approach. In vitro micro-neutralization test has demonstrated that antibodies in this invention had very strong neutralization activity to different mutation sublineages of H5N1 virus, and the characteristics of the monoclonal antibodies were that they had broad neutralization spectrum and high neutralization titer. In order to further demonstrate the anti-viral effect of the monoclonal antibodies in vivo, the present invention was based on H5N1 virus infection of the animal model Balb/C mice, and an in vivo verification experiment in which a monoclonal antibody was used for the anti-viral treatment of a H5N1 avian influenza virus strain was conducted in an animal biosafety level 3 laboratory. The details are as follows:

1. Materials and Methods (1) Animal: Balb/C mice, SPF, 6-8 weeks, female, weight about 20 g.

(2) Monoclonal Antibody: anti-H5 MAb 13D4, anti-H5 MAb 8G9, anti-HIV p24 MAb 18H12

(3) H5N1 virus: Bar-Head Gs/QH/15C/2005 (H5N1)

(4) Anesthetic: Isoflorane (5) Animal grouping: Mice were sent to ABSL-3 laboratories one day in advance and were divided into 6 groups with 6 mice in each cage, they were marked as G1, G2, G3 . . . G6. The weight of each mouse was recorded. See table 3 for details.

(6) Virus infection: Virus was pre-diluted to $10^3$ $TCID_{50}$/ul. The amount of virus inoculated for each mouse was 25 ul. Mice were first anesthetized with isoflorane before inoculation and then were infected with the virus via nasal inoculation.

(7) Monoclonal antibody interference: 24 h (dpi.1) after virus infection, mice of the antibody treatment group were injected different antibodies respectively by 20 mg/kg body weight with an injection volume of 100 ul/mouse.

(8) Observation Recording: The survival situation and corresponding behavioral characters of the mice were daily recorded from day 1 to day 14 after virus infection.

TABLE 3

Feasibility experiment scheme of the H5N1 antiviral therapy of monoclonal antibodies 8G9 and 13D4

| Group | MAb | Time point for MAb intervention |
|---|---|---|
| G1 | Negative control | — |
| G2 | Viral control | — |
| G3 | MAb Control | Irrelevant MAb (anti-HIV p24 18H12) |
| G4 | H5 Mab-8G9 | 1 dpi. (24 hours) |
| G5 | H5 Mab-13D4 | 1 dpi. (24 hours) |
| G6 | 8G9 + 13D4* | 1 dpi. (24 hours) |

*1:1 mixture of 8G9 and 13D4 with final concentration of 20 mg/ml

2. Results and Analysis

By observing the survival situation of the mice from day 1 to day 14 after virus infection (Table 4), it was found that as with those of the negative control group, mice of the antibody treatment group all survived normally to day 14, and the treatment effect was 100%. While mice of the virus control group and irrelevant monoclonal antibody control group began to die from day 7 after virus infection and were all dead on day 10 with a mortality rate of 100%. These results indicated that the anti-H5 monoclonal antibodies 8G9 and 13D4 could effectively treat the H5N1 avian influenza virus Bar-Head Gs/QH/15C/2005 infection of mice in vivo.

TABLE 4

Survival situation of mice 1-14 days after virus infection

| Group | Total No. | Day post-inoculation 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| G1-Neg control | 6 | 6 | 6 | 6 | 6 | 6 | 6 | 6 | 6 | 6 | 6 | 6 | 6 | 6 | 6 |
| G2-Viral Control-dpi.1 | 6 | 6 | 6 | 6 | 6 | 6 | 6 | 4 | 1 | 1 | 0 | 0 | 0 | 0 | 0 |
| G3-Mab control-dpi.1 | 6 | 6 | 6 | 6 | 6 | 6 | 6 | 3 | 1 | 1 | 0 | 0 | 0 | 0 | 0 |
| G4-H5 Mab-8G9-dpi.1 | 6 | 6 | 6 | 6 | 6 | 6 | 6 | 6 | 6 | 6 | 6 | 6 | 6 | 6 | 6 |
| G5-H5 Mab-13D4-dpi.1 | 6 | 6 | 6 | 6 | 6 | 6 | 6 | 6 | 6 | 6 | 6 | 6 | 6 | 6 | 6 |
| G6-8G9 + 13D4-dpi.1 | 6 | 6 | 6 | 6 | 6 | 6 | 6 | 6 | 6 | 6 | 6 | 6 | 6 | 6 | 6 |

Example 3

Animal Experiment of Broad-Spectrum Antiviral Therapy of Monoclonal Antibody The above experiments have demonstrated that monoclonal antibodies 13D4 and 8G9 can successfully treat the H5N1 avian influenza virus infection of mice. Due to the high variability of H5N1 avian influenza virus, the antigenicities of different variant subtypes of H5N1 avian influenza virus strains are clearly different, so that it was necessary to further test the broad-spectrum antiviral effect of monoclonal antibodies against H5N1 avian influenza virus strains that are significantly distinct in genetic properties.

1. Materials and Methods (1) Animal: Balb/C mice, SPF, 6-8 weeks, female, weight about 20 g.

(2) Monoclonal antibody: anti-H5 MAb 13D4, anti-HIV p24 MAb 1E4

(3) H5N1 virus: Indonesia/542/2006, Bar-Head Gs/QH/15C/2005, Vietnam/1194/2004, Shenzhen/406H/2006

(4) Anesthetic: Isoflorane (5) Animal grouping: Mice were sent to ABSL-3 laboratories one day in advance and were divided into 21 groups with 6 mice in each cage, they were marked as G1, G2, G3 . . . G21. The weight of each mouse was recorded. See table 5 for detailed scheme.

(6) Virus infection: Virus was pre-diluted to $10^3$ $TCID_{50}$/ul. The amount of virus inoculated for each mouse was 25 ul. Mice were first anesthetized with isoflorane before inoculation and then were infected with the virus via nasal inoculation.

(7) After 24 h, 48 h, and 72 h from virus infection, mice of the antibody treatment group were injected different antibodies respectively by 20 mg/kg body weight with an injection volume of 100 ul/mouse.

(8) Observation Recording: The survival situation and corresponding behavioral characters of the mice were daily recorded from day 1 to day 14 after virus infection.

TABLE 5

Experimental scheme for verifying the broad-spectrum H5N1 antiviral treatment ability of monoclonal antibodies

| H5N1 virus strain | Sublineage | Group No. | Group | Mice No. |
|---|---|---|---|---|
| Indonesia/542/2006 | Indonesia | G1 | Viral control | 6 |
| | | G2 | MAb control | 6 |
| | | G3 | Dpi.1 - 24 h | 6 |
| | | G4 | Dpi.2 - 48 h | 6 |
| | | G5 | Dpi.3 - 72 h | 6 |

TABLE 5-continued

Experimental scheme for verifying the broad-spectrum H5N1 antiviral treatment ability of monoclonal antibodies

| H5N1 virus strain | Sublineage | Group No. | Group | Mice No. |
|---|---|---|---|---|
| BHGs/QH/15C/2005 | Europe | G6 | Viral control | 6 |
| | | G7 | MAb control | 6 |
| | | G8 | Dpi.1 - 24 h | 6 |
| | | G9 | Dpi.2 - 48 h | 6 |
| | | G10 | Dpi.3 - 72 h | 6 |
| Vietnam/1194/2004 | Vietnam | G11 | Viral control | 6 |
| | | G12 | MAb control | 6 |
| | | G13 | Dpi.1 - 24 h | 6 |
| | | G14 | Dpi.2 - 48 h | 6 |
| | | G15 | Dpi.3 - 72 h | 6 |
| Shenzhen/406H/2006 | China | G16 | Viral control | 6 |
| | | G17 | MAb control | 6 |
| | | G18 | Dpi.1 - 24 h | 6 |
| | | G19 | Dpi.2 - 48 h | 6 |
| | | G20 | Dpi.3 - 72 h | 6 |
| Negative control | NC | G21 | Negative control | 6 |

2. Results and Analysis

The survival situation of mice from day 1 to day 14 after virus infection was observed. According to the difference in the time of death of the mice in each group, it could be known that the virulence of different H5N1 virus strains for mice was clearly different. The most virulent virus was SZ/406H. Mice of the virus control group began to die 3 days after infection and were all dead on day 4 after infection. Mice of the corresponding irrelevant antibody group began to die 4 days after infection and were all dead on day 5 after infection. The least virulent virus was IDN/542, except for the one mouse of the antibody control group that died on day 8 after infection and the one of the virus control group that died on day 11 after infection, all the rest survived. The virulence of QH/15C and VNM/1194 was comparable. Mice of both the virus control group and antibody control group of the former began to die 6 days after infection and were all dead 7 days after infection. For the latter, mice of the virus control group were all dead 7 days after infection while mice of the antibody control group began to die 7 days after infection and were all dead on day 8 after infection.

For antibody intervention treatment groups of different time points, the therapeutic effect for the three kinds of viruses IDN/542, QH/15C, and VNM/1194 were 100% with the antibody intervention of 24 h, 48 h and 72 h. As those of the negative control group, all the mice survived normally for 14 days. While for the antibody treatment of the SZ/406H virus, the situation was relatively complicated: the cure rate of the 24 h intervention group was 100%; the cure rate of the 48 h intervention group was 83.3%; the 72 h intervention group was not able to successfully treat the virus infection of the mice and all 6 mice finally died. Comparing to the virus control group, the time when the mice started to die and that when all of them finally died was postponed for 1 day and 2 days respectively. This may be related to the too high virulence of the virus, the too fast in vivo replication, and the too late antibody intervention.

The above results indicate that anti-H5 monoclonal antibody 13D4 has a good broad-spectrum anti-viral therapeutic effect for animals infected with H5N1 viruses.

TABLE 6

Survival situation of mice 1-14 days after virus infection

| Virus | Group | Total no. | Day post-inocualtion (dpi.) 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| IDN/542 | G1-Viral cont. | 6 | 6 | 6 | 6 | 6 | 6 | 6 | 6 | 6 | 6 | 6 | 5 | 5 | 5 | 5 |
| | G2-Mab cont. | 6 | 6 | 6 | 6 | 6 | 6 | 6 | 6 | 5 | 5 | 5 | 5 | 5 | 5 | 5 |
| | G3-dpi.1 | 6 | 6 | 6 | 6 | 6 | 6 | 6 | 6 | 6 | 6 | 6 | 6 | 6 | 6 | 6 |
| | G4-dpi.2 | 6 | 6 | 6 | 6 | 6 | 6 | 6 | 6 | 6 | 6 | 6 | 6 | 6 | 6 | 6 |
| | G5-dpi.3 | 6 | 6 | 6 | 6 | 6 | 6 | 6 | 6 | 6 | 6 | 6 | 6 | 6 | 6 | 6 |
| QH/15C | G6-Viral cont. | 6 | 6 | 6 | 6 | 6 | 6 | 5 | 0 | 0 | 0 | 0 | 0 | 0 | 0 | 0 |
| | G7-Mab cont. | 6 | 6 | 6 | 6 | 6 | 6 | 4 | 0 | 0 | 0 | 0 | 0 | 0 | 0 | 0 |
| | G8-dpi.1 | 6 | 6 | 6 | 6 | 6 | 6 | 6 | 6 | 6 | 6 | 6 | 6 | 6 | 6 | 6 |
| | G9-dpi.2 | 6 | 6 | 6 | 6 | 6 | 6 | 6 | 6 | 6 | 6 | 6 | 6 | 6 | 6 | 6 |
| | G10-dpi.3 | 6 | 6 | 6 | 6 | 6 | 6 | 6 | 6 | 6 | 6 | 6 | 6 | 6 | 6 | 6 |
| VNM/1194 | G11-Viral cont. | 6 | 6 | 6 | 6 | 6 | 6 | 6 | 0 | 0 | 0 | 0 | 0 | 0 | 0 | 0 |
| | G12-Mab cont. | 6 | 6 | 6 | 6 | 6 | 6 | 6 | 3 | 0 | 0 | 0 | 0 | 0 | 0 | 0 |
| | G13-dpi.1 | 6 | 6 | 6 | 6 | 6 | 6 | 6 | 6 | 6 | 6 | 6 | 6 | 6 | 6 | 6 |
| | G14-dpi.2 | 6 | 6 | 6 | 6 | 6 | 6 | 6 | 6 | 6 | 6 | 6 | 6 | 6 | 6 | 6 |
| | G15-dpi.3 | 6 | 6 | 6 | 6 | 6 | 6 | 6 | 6 | 6 | 6 | 6 | 6 | 6 | 6 | 6 |
| SZ/406H | G16-Viral cont. | 6 | 6 | 6 | 5 | 0 | 0 | 0 | 0 | 0 | 0 | 0 | 0 | 0 | 0 | 0 |
| | G17-Mab cont. | 6 | 6 | 6 | 6 | 3 | 0 | 0 | 0 | 0 | 0 | 0 | 0 | 0 | 0 | 0 |
| | G18-dpi.1 | 6 | 6 | 6 | 6 | 6 | 6 | 6 | 6 | 6 | 6 | 6 | 6 | 6 | 6 | 6 |
| | G19-dpi.2 | 6 | 6 | 6 | 6 | 6 | 6 | 6 | 6 | 6 | 6 | 5 | 5 | 5 | 5 | 5 |
| | G20-dpi.3 | 6 | 6 | 6 | 6 | 2 | 1 | 0 | 0 | 0 | 0 | 0 | 0 | 0 | 0 | 0 |
| NC | G21-negative cont. | 6 | 6 | 6 | 6 | 6 | 6 | 6 | 6 | 6 | 6 | 6 | 6 | 6 | 6 | 6 |

Example 2

Assemble of the Detection Kit (Enzyme-Linked Immunosorbent Assay ELISA) for HA Antigen of Subtype H5 Influenza Virus Double antibody sandwich assay was used in the kit to detect the HA antigen of the subtype H5 influenza virus. First, monoclonal antibodies against the HA gene of subtype H5 influenza virus were pre-attached to the surface of the polyethylene microwell plate in the kit. After the lytic H5-type influenza virus HA antigen was added to the microwell, the pre-coated monoclonal antibodies can capture it, and the enzyme-labeled monoclonal antibodies then added could also bind to it. The result was then determined via the enzyme-catalyzed chromogenic level of the substrate. When the specimen does not contain influenza virus antigens or is not the H5 influenza virus, the substrate will not change color. Specimens that can be tested include excreta, secretions from the mouth and nasal cavities, intact or lytic viruses of the chicken embryo culture, etc.

Preparation of the ELISA Plate

Monoclonal antibodies against the anti-H5-type influenza virus HA gene were pre-attached to the surface of the polyethylene microwell plate in the kit. The monoclonal antibodies were attached by incubating in 10 mM phosphate buffer (PB, pH=7.4) overnight at 37° C. Said plate was then washed once with PBST (10 mM PBS+0.05% Tween 20), dried, and blocked with the blocking solution (10 mMPBS+2% gelatin) for 2 hr at 37° C. After drying again, it was packaged in vacuum as finished ELISA plate (8×12 well) of the kit.

Preparation of Other Components of the Kit

Components of the Virus Lysate:

Lysate A (LB-A): 6% CHAPS+2% Tween-20+1% Tween-80.

Lyate B (LB-B): 100 mM PMSF, dissolved with isopropyl alcohol and the working final concentration was 2 mM.

Lysate C (LB-C): 10 mM PBS, pH7.4

Enzyme-Labeled Reagent: Monoclonal antibodies against the anti-H5-type influenza virus HA gene were labeled with HRP and get enzyme-labeled reagent with appropriate dilution.

Positive control: Inactivated virus of the H5-N-1-Yu22 strain with proper title was used as positive control.

Negative control: Lysate A was used as negative control.

Color developing reagent A: 13.4 g/L $Na_2HPO_4.12H_2O$+4.2 g/L citric acid. $H_2O$+0.3 g/L carbamide peroxide.

Color developing reagent B: 0.2 mM/LTMB (3,3',5,5'-Tetramethyl benzidine)+20 mM/L DMF (N,N-dimethyl formamide).

Stop Buffer: 2M concentrated sulfuric acid.

Concentrated Washing Buffer: 20×PBST

Microplate Sealing Film: two sheets

Ziplock Bag: one

Instruction: one.

Detection Procedure

Solution preparation: 50 ml concentrated buffer (20×) was diluted with distilled water or deionized water to 1000 ml for use.

Numbering: The samples were numbered according to the microplate sequence. 3 negative control wells, 2 positive control wells and 1 blank control well should be set on every plate (sample and Enzyme-Labeled Reagent would not be added into the blank control well, the other steps remained the same).

Sample Treatment and Application:

When the sample was liquid (including the original samples, chicken embryo culture samples, cell culture samples): Appropriate amount of the mixture of LB-A and LB-B was prepared as required by each plate with 4 μl LB-B for every 100 μl LB-A, agitated and mixed well. Then, the reaction was carried out by first adding 100 μl sample into each well on the microwell plate, and then adding 100 μl of the prepared lysate described above.

When the sample was dry swab original sample: 1 ml LB-A, 40 μl LB-B and 1 ml PBS were mixed together and added into a sample tube. The tube was agitated well to dissolve the sample. The mixture was agitated again for suspension after incubating for 30 min at room temperature. It was then centrifuged for 5 min at 6000 rpm, and the supernatant was taken for analysis by adding 100 μl to each well to allow reaction.

When the sample was dry egesta original sample: 1 ml LB-A, 40 μl LB-B and 1 ml PBS were mixed together and added into a sample tube. The dry egesta was suspended to produce a 10% (w/v) egesta suspension sample. The sample was dissolved after agitation and was incubated for 30 min at room temperature. The mixture was agitated again for suspension and was centrifuged for 5 min at 6000 rpm. Then the supernatant was taken, 100 μl of which was added to each well to allow reaction.

Negative and positive control wells should be included for every detection experiment. 100 μl control solution should be added to each well.

Incubation: After being sealed with microplate sealing film, the plate was shaken on a plate shaker at moderate speed for 60 min at room temperature (25~28° C.).

Washing: The sealing film was carefully removed and the plate was washed for 5 times with the plate washing machine and was dried after the last washing.

Enzyme addition: 100 μl Enzyme-Labeled Reagent was added into each corresponding well respectively.

Incubation: After sealed with the sealing film, the plate was incubated for 30 min at 37° C.

Repeated step 6.

Color reaction: 50 μl of each of the color developing buffer A and B were added into each well. The plate was shaken gently to mix them well and the mixture was kept away from light for color reaction for 30 min at 37° C.

Detection: A drop of Stop Buffer (50 μl) was added into each well and gently shaken to mix well. The OD values of each well were determined with microplate reader at single wavelength of 450 nm (blank control was needed) or dual-wavelength of 450 nm/630 nm.

Result Assessment a) Normal range of negative control: Under normal conditions, OD value of the negative well should be no more than 0.1 (if the OD value of the negative control well was more than 0.1, it should be discarded; if the OD values of all the negative control wells were more than 0.1, the experiment should be repeated. If the OD values of the negative control wells were less than 0.03, then the OD value should be regarded as 0.03).

b) Normal range of the positive control: Under normal conditions, the OD value of the positive control should be no less than 0.5.

c) Calculation of the CUTOFF value: 0.15 plus the average OD value of the negative control wells.

d) Determination of the Positive Reaction: When the OD value was no less than the CUTOFF value, it was a positive reaction for the HA antigen of H5-type avian influenza virus.

e) Determination of the Negative Reaction: When the OD value was less than the CUTOFF value, it was a negative reaction for the HA antigen of H5-type avian influenza virus.

Example 3

Isolation of Genes of the Light Chain and Heavy Chain Variable Regions of the Monoclonal Antibodies $10^7$ hybridoma cells were cultured in semi-adherent culture flask. The cells adhering to the flask walls were blown away from walls for suspension. The cells were transferred to a new 4 ml centrifuge tube, centrifuged at 1500 rpm for 3 min. The precipitated cells were collected and suspended again in 100 μl sterilized PBS (pH 7.45), and then transferred to another 1.5 ml centrifuge tube. 800 μl Trizol (Roche, Germany) was added to the tube, gently mixed, and incubated for 10 min. 200 μl chloroform was added and agitated well for 15 sec, incubated for 10 min, centrifuged at 12000 rpm at 4° C. for 15 min. Liquid of the top layer was transferred to a new 1.5 ml centrifuge tube. Equal volume of Isopropanol was added to the tube, mixed and incubated for 10 min. The mixture was centrifuged at 12000 rpm at 4° C. for 10 min. The supernatant was discarded and 600 μl 75% ethanol was added for washing. The mixture was centrifuged at 12000 rpm at 4° C. for 5 min. After discarding the supernatant, the mixture was precipitated at 60° C. and dried in vacuum for 5 min. The transparent precipitate was dissolved in 70 μl diethyl pyrocarbonate (DEPC) $H_2O$. The solution was divided into two tubes, with 1 μl reverse transcription primer added into each tube. The reverse transcription primer added to one tube was MVJkR (5'-CCg TTT(T/g) AT (T/C) TC CAg CTT ggT (g/C)

CC-3'). It was used to amplify genes of the light chain variable region. The reverse transcription primer in another tube was MVDJhR (5'-C ggT gAC Cg (T/A)ggT (C/g/T) CC TTg (g/A) CC CCA-3'), which was used to amplify genes in the heavy chain variable region. 1 μl dNTP (Shanghai Shenggong) was further added into each tube. The tube was put in a waterbath at 72° C. for 10 min, and was then put immediately into an ice bath for 5 min. 10 μl 5× reverse transcription buffer, 1 μl AMV (10 u/μl, Promega) and 1 μl Rnasin (40 u/μl, Promega) were added to the tube, mixed well and the RNA was reverse transcripted into cDNA at 42° C.

For the isolation of the variable regions of the antibody gene, polymerase chain reaction (PCR) method, a set of primers synthesized according to the Ig-Prime kits of Novagen company, and other two downstream primers, MVJkR and MVDJhR, that were synthesized separately by Shanghai Bioasia, were used. MVJkR was the downstream primer for amplifying the gene of light chain variable region and MVDJhR was the downstream primer for amplifying the gene of heavy chain variable region. The two cDNA molecules synthesized above were used as templates. The conditions for the PCR reactions were: 94° C. for 5 min, 94° C. for 40 sec, 53° C. for 1 min, 72° C. for 50 sec, 35 cycles, 72° C. for 15 min. Desired fragment was recovered, cloned into the pMD 18-T vector, and sequenced by Shanghai Bioasia. The sequence of the antibody variable region was determined after BLAST sequence alignment and the corresponding amino acid sequences were deduced.

Genes of antibody variable regions were cloned, according to the above method, from the 8G9, 13D4, 20A11 avian influenza monoclonal antibody hybridoma cell lines, and corresponding amino acid sequence was deduced. FIG. 7 shows sequences of the upstream primers. FIG. 8 shows the nucleotide and amino acid sequence numbers of the variable regions of the three monoclonal antibodies. The complementary determinant region (CDR) in FIG. 9 was determined by Kabat method (Kabat E A, Wu T T, Perry H M, Gottesman K S, Coeller K. Sequences of proteins of immunological interest, U.S. Department of Health and Human Services, PHS, NIH, Bethesda, 1991). Among them, the CDR region of 13D4 is the same as that of 20A11, so that they were speculated to come from the same monoclonal antibody.

TABLE 7

Upstream primer sequences for amplifying genes of the variable regions of avian influenza monoclonal antibody (SEQ ID NOS: 93,94 95, 96, 95, AND 96, respectively)

| Gene of monoclonal antibody variable region | Upstream primer name | Upstream primer sequence |
|---|---|---|
| 8G9 Vh | MuIgVh5'-E2 | 5'-AT gg(A/g) ATg gA(C/g) C(g/T)(g/T) I(A/g)T CTT T(A/C)T CT-3' |
| 8G9 Vk | MuIgkVl5'-D1 | 5'-AT ggA TTT (A/T)CA (A/g)gT gCA gAT T(A/T)T CAg CTT-3' |
| 13D4 Vh | MuIgVh5'-B1 | 5'-ATg (A/g)AA Tg(C/g) A(C/g)C Tgg gT(C/T) (A/T)T (C/T) CTC TT-3' |
| 13D4 Vk | MuIgkVl5'-D2 | 5'-AT ggg C(A/T)T CAA gAT g(A/g)A gTC ACA (g/T)(A/T) (C/T) (C/T)C(A/T) gg-3' |
| 20A11 Vh | MuIgVh5'-B1 | 5'-ATg (A/g)AA Tg(C/g) A(C/g)C Tgg gT(C/T) (A/T)T (C/T) CTC TT-3' |
| 20A11 Vk | MuIgkVl5'-D2 | 5'-AT ggg C(A/T)T CAA gAT g(A/g)A gTC ACA (g/T)(A/T) (C/T) (C/T)C(A/T) gg-3' |

TABLE 8

Nucleotide and amino acid sequence numbers of the variable regions of three monoclonal antibodies

| Monoclonal antibody name | Vh nucleotide sequence | Vh amino acid sequence | Vk nucleotide sequence | Vk amino acid sequence |
|---|---|---|---|---|
| 8G9 | SEQ ID NO: 1<br>SEQ ID NO: 41 | SEQ ID NO: 2<br>SEQ ID NO: 42 | SEQ ID NO: 3 | SEQ ID NO: 4 |
| 13D4 | SEQ ID NO: 5<br>SEQ ID NO: 43<br>SEQ ID NO: 45 | SEQ ID NO: 6<br>SEQ ID NO: 44<br>SEQ ID NO: 46 | SEQ ID NO: 7 | SEQ ID NO: 8 |
| 20A11 | SEQ ID NO: 9 | SEQ ID NO: 10 | SEQ ID NO: 11 | SEQ ID NO: 12 |

TABLE 9

| The amino acid sequences of CDRs of thee monoclonal antibodies determined by Kabat method | | | | | | |
|---|---|---|---|---|---|---|
| Single chain antibody | Amino acid sequence of the CDR of antibody heavy chain | | | Amino acid sequence of the CDR of antibody light chain | | |
| strain | CDR1 | CDR2 | CDR3 | CDR1 | CDR2 | CDR3 |
| 8G9 | FWMN (SEQ ID NO: 13) | RIDPYDSETH (SEQ ID NO: 14) | GIATLMVLPDY (SEQ ID NO: 15) | HASQDISSNMG (SEQ ID NO: 16) | HGTNLED (SEQ ID NO: 17) | VQYIQFPWT (SEQ ID NO: 18) |
| 13D4 | GHWIE (SEQ ID NO: 19) | EILPGSGNIH (SEQ ID NO: 20) | LGTTAVERDWYFDV (SEQ ID NO: 21) | KASQNVGTHLA SEQ ID NO: 22 | SASYRYS SEQ ID NO: 23 | QQYNNFPLT SEQ ID NO: 24) |
| 20A11 | GHWIE SEQ ID NO: 25 | EILPGSGNIH SEQ ID NO: 26 | LGTTAVERDWYFDV SEQ ID NO: 27 | KASQNVGTHLA SEQ ID NO: 28 | SASYRYS SEQ ID NO: 29 | QQYNNFPLT SEQ ID NO: 30 |

Example 4

Expression of Single Chain Antibody and Detection of its Activities

The heavy and light chain variable regions of the antibody gene were linked with a short peptide $(GGGGS)_3$ to form a DNA fragment encoding a single chain antibody. 8G9 VHF/8G9 VHR were used as the primer pair to amplify the variable region fragment of 8G9 heavy chain. 8G9 VKF/8G9 VKR were used as the primer pair to amplify the variable region fragment of 8G9 light chain. 13D4 VHF/13D4 VHR were used as the primer pair to amplify the variable region fragment of 13D4 heavy chain. 13D4 VKF/13D4 VKR were used as the primer pair to amplify the variable region fragment of 13D4 light chain. The sequences of these primers were shown in Table 10. The four fragments were recovered respectively, and the heavy chain and light chain variable region fragments were then used as primers and templates for each other to perform overlapping extension in a new PCR system. A small amount of full-length single chain antibody fragments were obtained. Then the full-length fragments were used as templates and 8G9 VHF/8G9 VKR were used as primers to mass amplify the overlapped 8G9 single chain antibody fragment. 13D4 VHF/13D4 VKR were used as primers to mass amplify the overlapped 13D4 single chain antibody fragment. The single chain antibody fragments were recovered by digesting them with NdeI and EcoR I, and cloning them into the prokaryotic expression vector pT0-T7 digested with the same enzymes. Using ER2566 *E. coli* as expression strain, the proteins expressed by standard methods were present in the form of insoluble inclusion bodies. The inclusion bodies were washed and purified with conventional methods, and the resulting single chain antibodies were mainly dissolved in 8M urea. The single chain antibody protein dissolved in 8M urea was dialyzed gradually in 1×PBS to allow the protein to renature. The dialyzed solution was centrifuged at 12000 rpm for 10 min and the precipitate was removed. Perform activity analysis for the preliminarily purified single chain antibody solution finally obtained.

TABLE 10

| Primers used for single chain antibody and chimeric antibody cloning (SEQ ID NOS: 47-67, respectively) | |
|---|---|
| Primer name | Primer sequence |
| 8G9VHF | 5'- TTACATATGCAGGTCCAACTGCTGC-3' |
| 8G9VHR | 5'- gCTACCACCCCCTCCAgATCCgCCACCTCCAGAGATTCGGTG ACCGTG-3' |
| 8G9VKF | 5'-ATCTggAgggggTggTAgCggTggAggCgggAgTGACATCCTG ATGACCCAA -3' |
| 8G9VKR | 5'- TTAGAATTCCTACCCGTTTGATCTCCAGC -3' |
| 13D4VHF | 5'- TTACATATGCAGGTTCAGCTGCAGC-3' |
| 13D4VHR | 5'- gCTACCACCCCCTCCAgATCCgCCACCTCCCGAATTCGAG CT CGG-3' |
| 13D4VkF | 5'-ATCTggAgggggTggTAgCggTggAggCgggAgTGACATTGTG ATGACC-3' |
| 13D4VkR | 5'- TTAGAATTCCCGTTTTATTTCCAGCTTGG-3' |
| 8G98CHF1 | 5'- CCTGCTACTGATTGTCCCTGCATATGTCCTGTCCCAGGTCCAAC TGCAGCAGCCTGGGG -3' |
| 8G98CHF2 | 5'-TTTGGATCCATGGGAAGGCTTACTTCTTCATTCCTGCTACTG ATTGTCCC-3' |
| 8G9VHR1 | 5'-TTTCTCGAGGGAGGATACGGTCACGGAGGTGCCTTGACCCC AG-3' |

TABLE 10-continued

| Primers used for single chain antibody and chimeric antibody cloning (SEQ ID NOS: 47-67, respectively) | |
|---|---|
| Primer name | Primer sequence |
| 8G98CKF1 | 5'-GCTGCTGCTGTGGCTTACAGATGCAAGATGTGACATCCTGATGA CCCAATC-3' |
| 8G98CKF2 | 5'-TTTGAATTCATGTCTGTGCCAACTCAGGTCCTGGGGTTGCTGCT GCTGTGGCTTAC-3' |
| 8G9VKR1 | 5'-TTTCTCGAGAGCCCGTTTGATCTCCAG-3' |
| 13D4VHF1 | 5'-TCCTGCTACTGATTGTCCCTGCATATGTCCTGTCCCAGGTTCA GCTGCAGCAG-3' |
| 13D4VHF2 | 5'-TTTGGATCCATGGGAAGGCTTACTTCTTCATTCCTGCTACTGA TTGTCCCTG-3' |
| 13D4VHR1 | 5'-TTTTCTCGAGGGAGGACACGGTCACGGAGGTTCCTTGGCCCC AGACATC-3' |
| 13D4VHR2 | 5'-TTTTCTCGAGGGAGGACACGGTCACCAGGGTTCCTTGGCCCC AGACATC -3' |
| 13D4VkF1 | 5'-GCTGCTGCTGTGGCTTACAGATGCAAGATGTGACATTGTGAT GACCCAGTC-3' |
| 13D4VkF2 | 5'-TTTGAATTCATGTCTGTGCCAACTCAGGTCCTGGGGTTGCTGC TGCTGTGGCTTAC -3' |
| 13D4VkR2 | 5'-TTTCTCGAGCCGTTTTATTTCCAGCTTG-3' |

Competitive ELISA method was applied to determine the activity of the preliminarily purified 8G9 single chain antibody. Avian influenza polyclonal antibodies were coated in the wells of polystyrene plate and blocked with BSA. 50 μl of the above mentioned single chain antibody solution and 50 μl avian influenza H5 virus were added into the testing well. 50 μl 1×PBS solution and 50 μl avian influenza H5 virus were added into the negative control wells, while 50 μl avian influenza polyclonal antibody and 50 μl avian influenza H5 virus were added into the positive control wells. Each reaction was repeated in three wells. The solution in the wells was gently mixed, incubated at 37° C. for 1 hr, and then HRP labeled avian influenza polyclonal antibodies were added as secondary antibodies for another half hour of reaction. The color was allowed to develop at 37° C. for 15 min after the addition of Color Developing Buffers A and B. The results were read with microplate reader after the reaction was terminated. The average value of negative controls was 1.871, the average value of positive controls was 0.089, and the average value of the testing wells was 0.597, showing relatively high activity of the preliminarily purified 8G9 single chain antibody proteins 26 strains of H5N1 viruses were chosen to test the reactivity of said 8G9 single chain antibody with the virus using the hemagglutination inhibition (HI) assay. 25 μl PBS was added to each well of a 96-well hemagglutination plate. 25 μl 8G9 single chain antibody solution (0.08 mg/ml) was added to the first well and mixed well, 25 μl of which was then added to the second well and so on to dilute the antibody multiproportionally. 25 μl viruse was added to the single chain antibody, after incubating at room temperature for 30 min, 50 μl of 0.5% chicken red blood cells were added. Red blood cell agglutination was observed after incubating for 30 min. The result showed that 8G9 single chain antibody had HI activity for 19 ones of the virus strains (Table 11).

TABLE 11

Hemagglutination inhibition (HI) assay of the 8G9 single chain antibody against 26 strains of H5N1 virus

| H5N1 Virus strains | HI | H5N1 Virus strans | HI |
|---|---|---|---|
| A1 | >8 | C3 | 7 |
| A2 | >8 | D1 | >8 |
| A3 | 7 | D2 | 7 |
| A5 | >8 | E1 | 1 |
| A6 | 7 | E2 | 1 |
| A7 | 7 | F2 | <1 |
| A8 | 6 | F3 | <1 |
| B1 | 7 | G1 | 6 |
| B2 | 3 | H1 | <1 |
| B3 | >8 | H2 | <1 |
| B4 | >8 | B7 | >8 |
| B5 | <1 | B8 | 7 |
| B6 | 7 | C2 | 5 |

Note:
HI titer is diluted by the "n"$^{th}$ power of 2.
"n" is the number shown in the table.

YU22 H5N1 viruse was chosen to test the reactivity between said 13D4 single chain antibody and the virus using the hemagglutination inhibition (HI) assay. 25 μl PBS was added to each well of a 96-well hemagglutination plate. 25 μl 13D4 single chain antibody solution (0.18 mg/ml) was added to the first well and mixed well, 25 μl of which was then added to the second well and so on to dilute the antibody multiproportionally. 25 μl viruse was added to the single chain antibody, after incubating at room temperature for 30 min, 50 μl of 0.5% chicken red blood cells were added. Red blood cell agglutination was observed after incubating for 30 min. The results showed that 13D4 single chain antibody still had weak HI activity for YU22 virus when it was 8-fold diluted.

Example 5

Expression of Mutated and Chimeric Antibodies of the Antibody Gene Variable Regions and Test of the Antibody Activities Several amino acid mutations were found in the FR4 region of the 8G9 and 13D4 heavy chain variable region sequences through Blast sequence alignment analysis in NCBI website, which were speculated to be introduced due to the degeneracy of the MVDJhR downstream primer while cloning the gene. So amino acid mutagenesis was performed in the FR4 region of the 8G9 and 13D4 heavy chain variable region sequence. Among them, the nucleotide sequence of 8G9 VH was changed from SEQ ID NO: 1 to that set forth in SEQ ID NO: 41, its amino acid sequence was changed from SEQ ID NO: 2 to that set forth in SEQ ID NO: 42. The nucleotide sequence of 13D4 VH was changed from SEQ ID NO: 5 to those set forth in SEQ ID NO: 43 and SEQ ID NO: 45 respectively, its amino acid sequence was changed from SEQ ID NO: 2 to those set forth in SEQ ID NO: 44 and SEQ ID NO: 46 respectively.

In the VK region, the nucleotide and amino acid sequence of 13D4 are identical with that of 20A11. After mutation, the nucleotide sequence SEQ ID NO: 43 and amino acid sequence SEQ ID NO: 44 of 13D4 VH were in accordance with the nucleotide sequence SEQ ID NO:9 and amino acid sequence SEQ ID NO:10 of 20A11. Thus, expressing the chimeric antibody comprised of SEQ ID NO: 44 and SEQ ID NO: 8 simultaneously represents the chimeric antibody of 13D4 and 20A11.

Signal peptide sequences were added to the heavy chain and light chain variable region genes of the 8G9 and 13D4 monoclonal antibodies, which were then cloned into a eukaryotic expression plasmid containing the human gamma1 heavy chain and the kappa light chain constant region sequences. Among them, the plasmid pcDNA3.1-AH contained the human gamma1 heavy chain constant region sequence, and the plasmid pcDNA3.1-Ak contained the kappa light chain constant region sequence.

8G98CHF1/8G9VHR1 were used as a primer pair to amplify partial heavy chain signal peptide sequence and variable region sequence of 8G9. This PCR product was used as template and 8G98CHF2/8G9VHR1 were used as a primer pair to amplify the 8G9 heavy chain variable region sequence with the complete signal peptide. The amplified sequence was cloned into the plasmid pcDNA3.1-AH double digested with Bam HI/Xho I, to obtain the expression plasmid pcDNA3.1-AH8G9 expressing a human-mouse chimeric heavy chain. 8G98CKF1/8G9VKR1 were used as a primer pair to amplify the partial light chain signal peptide sequence and variable region sequence of 8G9. The amplified fragment was used as the PCR template and 8G98CKF2/8G9VKR1 were used as a primer pair to amplify the 8G9 light chain variable region fragment with the complete signal peptide sequence. The amplified sequence was cloned into the plasmid pcDNA3.1-Ak double digested with EcoR I/Xho I to obtain the expression plasmid pcDNA3.1-Ak8G9 expressing a human-mouse chimeric light chain.

Figure 1:
FIG. 1 is the diagram of expression vector for chimeric antibody.

As in the above method, 13D4VHF1/13D4VHR1 and 13D4VHF2/13D4VHR1 were used as primer pairs to amplify the 13D4 heavy chain signal peptide sequence and variable region fragment (including SEQ ID NO:43). The amplified sequence was cloned into the plasmid pcDNA3.1-AH double digested with Bam HI/Xho I to obtain the expression plasmid pcDNA3.1-AH13D4SV expressing a human-mouse chimeric heavy chain. 13D4VHF1/13D4VHR2 and 13D4VHF2/13D4VHR2 were used as primer pairs to amplify the 13D4 heavy chain signal peptide sequence and variable region fragment (including SEQ ID NO:45). The amplified sequence was cloned into the plasmid pcDNA3.1-AH double digested with Bam HI/Xho I to obtain the expression plasmid pcDNA3.1-AH13D4LV expressing a human-mouse chimeric heavy chain. 13D4VKF1/13D4VKR2 and 13D4VKF2/13D4VKR2 were used as primer pairs to amplify the 13D4 light chain signal peptide sequence and variable region fragment. The amplified sequence was cloned into the plasmid pcDNA3.1-Ak double digested with EcoR I/Xho I to obtain the expression plasmid pcDNA3.1-Ak13D4 expressing a human-mouse chimeric light chain. See FIG. 1 for the plasmid expressing chimeric antibody.

293 FT cells were co-transfected with the two plasmids carrying the chimeric heavy chain and the chimeric light chain using the calcium phosphate transfection method. The supernatant of the cell culture was collected to obtain the expressed chimeric antibodies (cAb).

Two kinds of 13D4 chimeric heavy chain plasmids were combined with the 13D4 chimeric light chain plasmid respectively to form two kinds of 13D4 chimeric antibodies. One of them is called 13D4 chimeric antibody SV, and the other is called 13D4 chimeric antibody LV. The initial concentration of the chimeric antibody and the mouse monoclonal antibody was adjusted to 14.76 μg/ml. Hemagglutinin inhibition (HI) activity assay was performed against 25 H5N1 virus strains using cell culture supernatant of two kinds of chimeric antibody. As shown in the result of table 12, the HI reactions of the two chimeric antibodies against 25 H5N1 virus strains were basically identical with that of 13D4 mouse monoclonal antibody, showing that both of them maintained the specificity and broad-spectrum property of mouse monoclonal antibody. The sequence of the 13D4 chimeric antibody SV was in accordance with that of 20A11, and therefore demonstrating that the chimeric antibody of 20A11 also had excellent specificity and broad-spectrum property.

TABLE 12

The result of the hemagglutinin inhibition (HI) assay of 13D4 chimeric antibody against 25 H5N1 virus strains.
(HI titer was diluted by the "n"$^{th}$ power of 2. "n" is following numbers)

| | Type of antibody | | |
|---|---|---|---|
| Type of virus | 13D4 chimeric antibody SV | 13D4 chimeric antibody LV | 13D4 mouse monoclonal antibody 14.6 ug/ml |
| A1 | >8 | >8 | >8 |
| A2 | 7 | 7 | 7 |
| A3 | 5 | 6 | 6 |
| A6 | 5.5 | 6.5 | 3 |
| A7 | 3.5 | 4 | 4 |
| A8 | 6 | 7 | 5 |
| B1 | >8 | >8 | >8 |
| B3 | 2 | 2 | 3 |
| B4 | 4 | 4 | 5 |
| B6 | <8 | >8 | >8 |
| B7 | 6.5 | 6 | 7 |
| B8 | 6 | 4 | >8 |
| C2 | 4 | 3 | 3 |
| C3 | 4 | 4 | 4 |
| C4 | NO | NO | NO |
| D1 | 5 | 4 | 5 |
| D2 | 5 | 4 | 5 |
| D3 | 5.5 | 4 | 6 |
| E1 | 6 | 5.5 | 7 |
| E2 | 3 | 3 | 6 |
| F2 | 5 | 5.5 | 5 |

TABLE 12-continued

The result of the hemagglutinin inhibition (HI) assay of 13D4 chimeric antibody against 25 H5N1 virus strains.
(HI titer was diluted by the "n"$^{th}$ power of 2. "n" is following numbers)

| | Type of antibody | | |
|---|---|---|---|
| Type of virus | 13D4 chimeric antibody SV | 13D4 chimeric antibody LV | 13D4 mouse monoclonal antibody 14.6 ug/ml |
| F3 | 6.5 | 6 | >8 |
| F4 | 1 | NO | 1 |
| G1 | 3 | 2 | 4 |
| H2 | 4 | 3 | 3 |

YU22 H5N1 virus was chosen to test the reactivity between the 8G9 chimeric antibody in the cell supernatant and the virus using the hemagglutination inhibition (HI) assay. The results showed that the 8G9 chimeric antibody still had HI activity for YU22 virus when it is was 16-fold diluted.

Example 5

Screening of Short Peptides that Simulate the Epitopes Recognized by the Monoclonal Antibody 8G9 from the Bacteriophage 12aa Peptide Library Screening of Bacteriophage Peptide The 12aa peptide phage display library of the New England Biolabs company (ph.D. C7C peptide library) was used to screen 12aa peptides binding to 8G9 mAb. The screening was performed according to the manufacturer's instruction and is briefly described below:

50 μl Protein A—Agarose medium (50% water suspension) was aliquoted into a microcentrifuge tube, to which 1 ml TBS and 0.1% Tween (TBST) solution were added. The tube was gently tabbed or vibrated to re-suspend the medium. After centrifuging at low speed for 30 sec to precipitate the medium, the supernatant was carefully removed. The medium was re-suspended in 1 ml blocking buffer and incubated at 4° C. for 60 min with occasional mixing. Meanwhile, $2\times10^{11}$ phage particles (equivalent to 10 μl of the original phage library) and 300 ng antibody were diluted with TBS buffer to a final volume of 200 μl with the final concentration of the antibody being 10 nM. The solution was incubated at room temperature for 20 min. After the blocking reaction, the medium was centrifuged at low speed, and then washed with 1 ml TBS for three times, each time the medium needs to be centrifuged. The phage-antibody mixture was added to the washed medium, gently mixed, and incubated at room temperature for 15 minutes with frequent mixing. The medium was centrifuged at low speed, and washed with 1 ml TBST for 10 times after discarding the supernatant. Then the media was re-suspended in 1 ml 0.2M Glycine-HCl (pH 2.2) and 1 mg/ml BSA, incubated at room temperature for 10 min to elute the bound phage particles. The eluted mixture was centrifuged for 1 min and the supernatant was carefully transferred to another new microcentrifuge tube. The eluted solution was immediately neutralized with 150 μl 1M Tris-HCl buffer, pH 9.1. Approximately 1 μl of the neutralized solution was used to determine the titer of the phage. The remaining phage solution was added into 20 ml bacterial culture of ER2738 host cells that were at early log growth phase. After culturing with vibration at 37° C. for 4.5 hour, the bacterial culture was transferred to a 50 ml centrifuge tube and centrifuged at 10,000 rpm for 20 min. The top 80% of the supernatant was collected and one-sixth volume of PEG/NaCl solution (20% PEG-8000, 2.5M NaCl) was added. The solution was kept at 4° C. overnight and centrifuged at 10,000 rpm at 4° C. for 15 min. The supernatant was discarded and the precipitated phage was dissolved with 1 ml TBS. The solution was centrifuged at 4° C. for 5 min, the supernatant was taken and to which one-sixth volume of PEG/NaCl solution was added. Then, the solution was kept at 4° C. for 0.5 hr, centrifuged at 10,000 rpm for 15 min at 4° C. The supernatant was discarded, and the precipitated phage was dissolved with 200 μl TBS and stored at 4° C. The above-mentioned procedures were repeated for another round of screening.

The overnight cultured ER2738 host cells were diluted into LB medium at the ratio of 1:10 and aliquoted into culture tubes (3 ml/tube). For each monoclonal antibody, 10 blue single-colony phage plaques on LB/IPTG/Xgal culture plates that had undergone three rounds of screening were selected and inoculated into the above mentioned culture tubes. The cell cultures were incubated with vibration at 37° C. for 4.5 hr. The cell cultures were transferred to 1.5 ml centrifuge tubes and centrifuged at 10,000 g. 200 μl of the supernatant was collected and stored, and the rest was used to extract ssDNA according to the manufacturer's instruction of small quantity M13 Isolation and Purification Reagent Kit (Shanghai Huashun Bioengineering Co., Ltd.). The sequences of the inserted 12aa peptide and 11 aa peptide were obtained after sequencing by Shanghai Bioasia Biotechnology Co., Ltd. and are shown in Table 13.

TABLE 13

The Amino Acid Sequences of the 12aa peptide and 11aa peptide binding to monoclonal antibody 8G9.

| Peptide No. | 12aa peptide sequence | Sequence ID No. |
|---|---|---|
| G1 | L P Y Y D P R A L L L R | SEQ ID No: 31 |
| G2 | H T P C D T R D C V L R | SEQ ID No: 32 |
| G3 | H P P C D T R D C V L R | SEQ ID No: 33 |
| G4 | A P A C D S R L C V L R | SEQ ID No: 34 |
| G5 | G D T R S F Y Y K L Y F | SEQ ID No: 35 |
| G6 | L P H A S P R A L V M R | SEQ ID No: 36 |
| G7 | T T A S N S K P P L H D | SEQ ID No: 37 |
| G8 | G P W E N L R A L F L R | SEQ ID No: 38 |

TABLE 13-continued

| The Amino Acid Sequences of the 12aa peptide and 11aa peptide binding to monoclonal antibody 8G9. | | |
|---|---|---|
| Peptide No. | 12aa peptide sequence | Sequence ID No. |
| G9 | D V I Y V D R W H I L R | SEQ ID No: 39 |
| G10 | S G Y S S R M D F L R | SEQ ID No: 40 |

Detection of Phage Peptide Binding Activities

Figure 2:
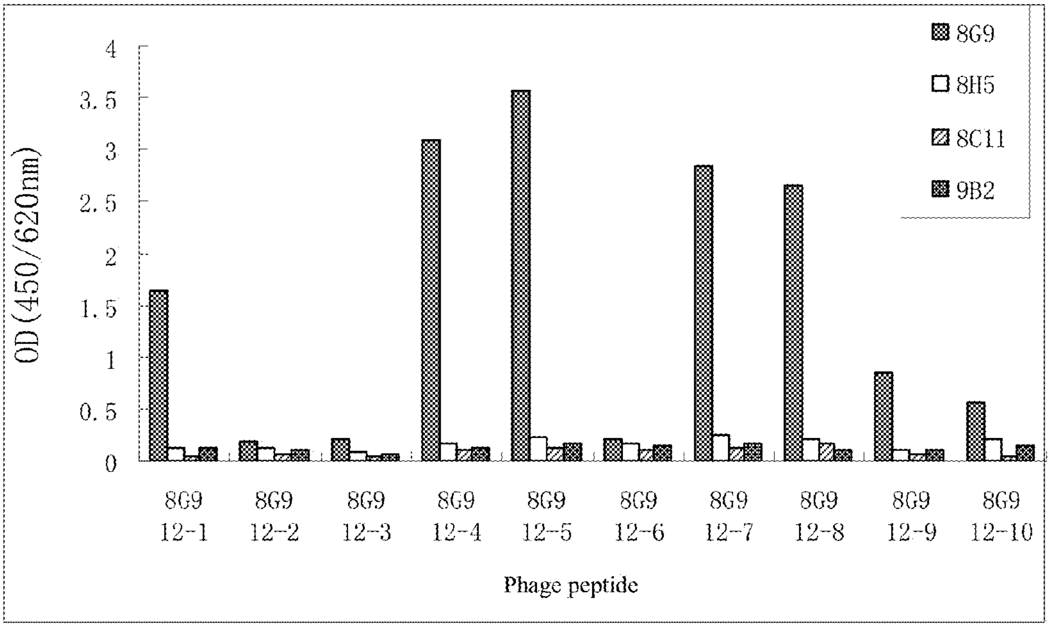
FIG. 2 shows the result of activity detection of the screening product screened with 8G9 from twelve-peptide library.

After the third rounds of screening, approximately 1 μl of the eluted phage was taken for titration. Single-colony phage blank plaques were selected and inoculated into ER2738 bacteria at log growth phase. After incubating at 37° C. for 4.5-5 hr, the bacterial culture was centrifuged and the phage supernatant was collected for ELISA assay, in which the 8G9 mouse monoclonal antibody was coated at the concentration of 1 μg/ml. The phage supernatant was used as primary antibody, 1:3,000 diluted Anti-M13/HRP antibody (Amersham Phamarcia Biotech, UK) was used as secondary antibody. The avian influenza related antibody 8H5 mAb, and the unrelated anti-HEV E2 protein antibodies 8C11mAb and 9B2 mAb were used as negative controls for the mouse monoclonal antibody. FIG. 2 shows the result of phage polypeptide test. It can be known from the test result that against the target antibody 8G9, most of the phage peptides had OD values three times higher than that of the control, indicating that the peptides had relatively good specificity.

Detection of the Binding Specificity of Phage Peptides

Figure 3:
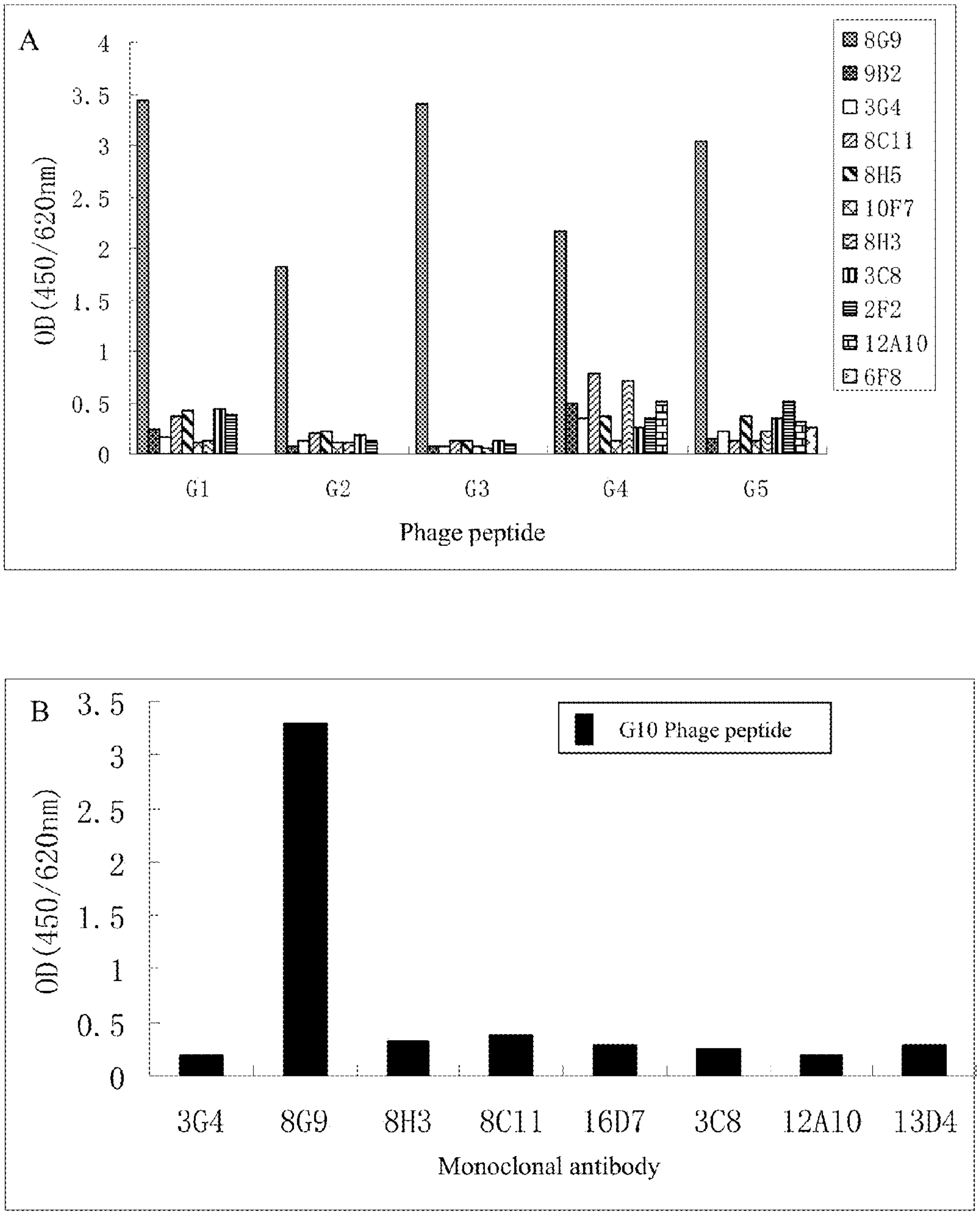
FIG. 3 shows the ELISA result of specific binding of phage peptide with 8G9.

The representative positive phage clones of the sequence G1-G5 obtained by 8G9 screening were selected to be amplified again in ER2738 bacterial for 4 hr. The supernatant was collected for ELISA to test its specificity. A total number of 10 strains were selected from AIV and HEV monoclonal antibodies, respectively, as controls. Among them, the monoclonal antibodies against AIV were 3G4, 8H5, 10F7, 3C8, 2F2; and the monoclonal antibodies against HEV were 9B2, 8C11, 8H3, 12A10, 6F8. Plates was coated with the antibodies at the concentration of 1 μg/ml, the detailed conditions for ELISA analysis were as above. As shown in FIG. 3, the reaction activity of these five sequences with the target monoclonal antibody 8G9 was very high, while the binding activity with the 10 control antibodies were all very low, and thus showing excellent specificity.

Example 6

Fused Expression of G1, G2, G3, G5 with the 239 Protein and Detection of their Activities Construction of the fused expression vectors for 239-G1, G2, G3 and G5

This laboratory expressed a fragment (a. a. 368-606) of HEV ORF2 in *E. coli*, the obtained recombinant protein 239 can be assembled into virus-like particles having good immunogenicity. Take the 239-G1 as an example, we have used the PCR method to construct the prokaryotic expression vector pT0-T7-239-G1, in which the C-terminal of 239 sequence was fused to the 12aa peptide sequence. First, primers for the 239 sequence and 12aa peptide sequence were designed (table 14). The first round of PCR amplification was carried out using the 239 gene as template and 239F/239XR1 as primers. The PCR products were recovered and purified and then used as templates for the second round of PCR amplification, in which the primers 239F/239G1R2 were used. These PCR products were recovered and purified and then used as templates for the third round of PCR amplification, in which the primers 239F/239G1R1 were used to obtain the 239-G5 fragment, which was recovered, purified, double digested with restriction enzymes NdeI and Bgl II, and ligated with the vector pT0-T7 double digested with Nde I and BamH I. The ligation product was transformed into *E. coli* ER2566. After being expressed in small amount, the plasmid was examined by enzyme digestion, and the positive clone contained the recombinant prokaryotic expression vector 239-G1. Plasmid of the 239-G2, 239-G3 and 239-G5 fusion protein was constructed using the same method.

TABLE 14

| Cloning primer sequences of the 239-G1, 239-G2, 239-G3 and 239-G5 (SEQ ID NOS: 68-77, respectively) | |
|---|---|
| Primer name | Primer sequences |
| 239-123F | 5'-TTT TTA CAT ATG ATA GCG CTT ACC CTG-3' |
| 239-G1R1 | 5'-TTTAGATCTACGAAGAAGAAGAGCACGCGGATCATAAT-3' |
| 239-G1R2 | 5'-AGCACGCGGATCATAATAAGGAAGgCTACCACCACCACCAgAACC-3' |
| 239-G2R1 | 5'-TTTAGATCTACGCAACACACAATCCCTAGTATCAC-3' |
| 239-G2R2 | 5'-CAATCCCTAGTATCACACGGCGTATGgCTACCACCACCACCAgAACC-3' |
| 239-G3R1 | 5'-TTTAGATCTACGCAACACACACAACCGCGAATCACACG-3' |
| 239-G3R2 | 5'-ACAACCGCGAATCACACGCAGGCGCgCTACCACCACCACCAgAACC-3' |
| 239-G5R1 | 5'-TTTAGATCTCCGCATCACCAGGGCTCGAGGGCTGG-3' |

TABLE 14-continued

| Cloning primer sequences of the 239-G1, 239-G2, 239-G3 and 239-G5 (SEQ ID NOS: 68-77, respectively) | |
|---|---|
| Primer name | Primer sequences |
| 239-G5R2 | 5'-CAGGGCTCGAGGGCTGGCGTGGGGCAGgCTACCACCACCACCAgAACC-3' |
| 239-XR3 | 5'-gCTACCACCACCACCAgAACCACCACCACCGGATCCgCgCggAggggggggCT-3' |

Expression and purification of the fusion proteins 239-G1, G2, G3 and G5.

ER2566 single colonies containing plasmids 239-G1, G2, G3 and G5 were each inoculated into 2 ml Kn-resistant LB medium. The bacteria cultures were incubated with vibration at 37° C. until the $OD_{600}$ value reached about 0.8. Then the cultures were transferred at the ratio of 1:1000 to 500 ml LB medium, and incubated until the $OD_{600}$ value reached about 1.0. Then 500 μl IPTG was added into the bacteria cultures to induce protein expression at 37° C. for 4 hr. The bacteria were collected by centrifugation at 8,000 rpm for 6 min at 4° C. The supernatant was discarded, and the bacteria precipitate was re-suspended with 20 ml/flask lysis buffer, incubated in ice-cold water, and treated with ultrasonic cell disruptor to break the cells. The conditions for the ultrasound treatment were as follows: working time: 5 min; pulse: treating for 2 sec and resting for 5 sec; output power: 70%. Then, the bacteria solution was centrifuged at 12,000 rpm for 10 min, the supernatant was saved, while the precipitate was re-suspended with 20 ml 2% Triton, vibrated for 30 min, and then centrifuged at 12,000 rpm for 10 min. The supernatant was saved, and the precipitate was re-suspended with 20 ml Buffer I and vibrated for 30 min. After repeating the Triton/Buffer I treatment once, the culture was centrifuged at 12,000 rpm for 10 min. The supernatant was saved, and the precipitate was re-suspended with 20 ml 2M Urea/Buffer I, vibrated for 30 min, and centrifuged at 12,000 rpm for 10 min. The supernatant was saved, and the precipitate was re-suspended with 20 ml 4M Urea/Buffer I, vibrated for 30 min, and then centrifuged at 12,000 rpm for 10 min. The supernatant was saved, and the precipitate was re-suspended with 20 ml 8M Urea/Buffer I, vibrated for 30 min, and then centrifuged at 12,000 rpm for 10 min. The supernatant was saved, and the proteins in the 8M and 4M Urea solutions were dialyzed into PBS with gradient dialysis (8M Urea-4M Urea-2M Urea-PBS).

Test of the Activities of Fusion Proteins 239-G1, G2, G3 and G5

Direct ELISA Assay 96-well plates were coated with the preliminarily purified fusion proteins 239-G1, G2, G3 and G5 at the concentration of 10 μg/ml for 2 hr at 37° C. Then, the plates were washed once, treated with Flu A blocking buffer at 37° C. for 2 hr and then at 4° C. overnight to block non-specific binding sites. After the blocking buffer was discarded, 100 μl of different enzyme-labeled antibodies were added into each well, including 8G9-HRP, 8H5-HRP and 8C11-HRP. Among them, the 8C11-HRP was a specific antibody against the 239 protein, and the 8G9-HRP was the monoclonal antibody used to screen the 12aa peptide. The plates were incubated with antibodies at 37° C. for 30 min, and washed with PBST for 5 times. Color was developed for 10 min with the addition of color developing solution and the reaction was terminated with the stopping buffer. The results shown in FIG. 4 were read with a microplate reader. It could be known from the results of FIG. 4 that all the 239 fusion proteins reacted with the antibody 8C11-HRP, and the values of reaction were higher than 3.0, indicating that the 239 vector fusion protein were expressed and purified correctly. 239-G3 and 239-G5 reacted with 8G9-HRP weakly. It was possible that the 12aa peptide fragments G1, G2, G3 and G5 obtained through 8G9 screening could not display the activity of the corresponding peptide fragments on the phage.

Example 7

Expression of the Proteins Fused by the 12aa Peptides G1, G2, G3, G5 and the HBV cAg Protein Construction of Fused Expression Vectors Based on the property of the a. a. 1-149 fragment of HBcAg to be expressed in the form of virus-like particles in *E. coli*, our laboratory inserted these 149 amino acids into the *E. coli* expression vector pT0-T7. The two amino acids at positions 79 and 80 of the B-cell-dominant epitope fragment of HBcAg were replaced with a linker to make the mutant HBc expression plasmid pC149-mut. HBcAg had very strong T cell immunogenicity. Fusion of foreign polypeptide in the internal MIR (mayor immunodominant region a. a. 78-83) of HBcAg would not change the polymerization property of its particle, and would enable foreign epitopes to be displayed on the particle surface.

2 copies of 12aa peptides G1, G2, G3 and G5 were inserted into the amino acid positions 79 and 80 of HBcAg to obtain the corresponding fusion proteins, named as HBc-DG1, HBc-DG2, HBc-DG3, and HBc-DG5, respectively. Take HBc-DG1 as an example, first, forward primers comprising the 12aa peptide sequence and the universal reverse primer HBcR were designed (Table 15) based on the sequences of the 12aa peptides and the sequence of vector pC149-mut respectively. pC149-mut was used as the template and the primers HBc-G1F3/HBcR were used for the first round of PCR amplification. The recovered and purified PCR products were used as template, and the primers HBc-G1F2/HBcR were used for the second round of PCR amplification. The recovered and purified PCR products were used as template, and the primers HBc-GIF 1/HBcR were used for the third round of PCR amplification to generate C149 a. a. 81-149, into which 2 copies of G1 sequences were ligated. The fragment was obtained after the digestion with Bgl II and EcoR I and purification. Meanwhile, the vector pC149-MUT was double digested with BamH I and EcoR I, recovered and ligated with the fragment. The ligated products were transformed into *E. coli* ER2566 for expression and enzyme digestion analysis of the plasmid. The correct plasmids shown by the analysis had two copies of the G1 sequences inserted, and were named as HBc-DG1. The same method was used to construct the plasmids of HBc-DG2, HBc-DG3 and HBc-DG5 fusion proteins

TABLE 15

| Cloning primer sequences of HBc-DG1, HBc-DG2, HBc-DG3 and HBc-DG5 (SEQ ID NOS: 78-90) | |
|---|---|
| Primer name | Primer sequence |
| HBc-G1F1 | 5'-TTTAGATCTGGTGGCGGAGGCTCACTTCCTTATTATGATCCCCG TGCTCTTCTTCTTC-3' |
| HBc-G1F2 | 5'-CCGTGCTCTTCTTCTTCGTGGAGGAGGTGGTTCCCTTCCA TATTACGAcCCtCGTGC-3' |
| HBc-G1F3 | 5'-TACGACCCTCGTGCACTTCTGCTTCGCGGATCCGTCGACGG TGGTGGAGGTTCAGG-3' |
| HBc-G2F1 | 5'-TTTAGATCTGGTGGCGGAGGCTCCCATACACCGTGTGATACTAGGGAT TGTGTGTTGCG-3' |
| HBc-G2F2 | 5'-GGGATTGTGTGTTGCGTGGAGGAGGTGGTTCTCATACGCCCTGCGATA CTAGAGATTG-3' |
| HBc-G2F3 | 5'-CCTGCGATACTAGAGATTGCGTCTTGCGGGGATCCGTCGACGGTGGT GGAGGTTCAGG-3' |
| HBc-G3F1 | 5'-TTTAGATCTGGTGGAGGAGGATCAGCACCTGCATGTGATTCGCGGTT GTGTGTGTTGC-3' |
| HBc-G3F2 | 5'-CGGTTGTGTGTGTTGCGTGGAGGAGGTGGTTCAGCCCCAGCCTGTG ACTCCCGCTTG-3' |
| HBc-G3F3 | 5'-TGTGACTCCCGCTTGTGTGTCCTCCGAGGATCCGTCGACGGTGGTG GAGGTTCAGG-3' |
| HBc-G5F1 | 5'-TTTAGATCTGGTGGAGGAGGCTCACTGCCCCACGCCAGCCCTCGAGCC CTGGTGATG-3' |
| HBc-G5F2 | 5'-CTCGAGCCCTGGTGATGCGGGGAGGAGGTGGTTCCTTGCCCCACGCCA GCCCTCGGG-3' |
| HBc-G5F3 | 5'-CACGCCAGCCCTCGGGCCCTGGTGATGCGGGGATCCGGTGGTGG AGGTTCAGG-3' |
| HBcR | 5'-TT GAA TTC TTA AAC AAC AGT AGT TT-3' |

Expression and purification of the fusion proteins

ER2566 bacteria strains containing plasmids expressing HBc-DG1, HBc-DG2, HBc-DG3, and HBc-DG5 were inoculated into 2 ml Kn-resistant LB medium. The bacteria cultures were incubated with vibration at 37° C. until the $OD_{600}$ value reached about 0.8. Then the cultures were transferred at the ratio of 1:1000 to 500 ml LB medium (Kn-resistant), and incubated until the $OD_{600}$ value reached about 0.8. Then 500 μl IPTG was added into the bacteria cultures to induce protein expression at 18° C. for 20 hr. The bacteria were collected by centrifugation at 8,000 g for 6 min at 4° C. The supernatant was discarded, and the bacteria precipitate was re-suspended with 20 ml/flask lysis buffer, incubated in ice-cold water, and treated with ultrasonic cell disruptor to break the cells. The conditions for the ultrasound treatment were as follows: working time: 5 min; pulse: treating for 2 sec and resting for 5 sec; output power: 70%. Then, the bacteria solution was centrifuged at 12,000 rpm for 10 min and the supernatant was saved.

Since the proteins expressed in the supernatant were relatively impure, purification was needed. These proteins could self-assemble to form particles under suitable conditions, thus the conditions for them to self-assemble to form particles shall be considered during protein purification. The following procedures were used to purify the proteins to promote the proteins to self-assemble and form particles: saturated ammonium sulfate was added in the amount of 33% of the total volume to precipitate the protein. The mixtures was then incubated on ice for 30 min, and centrifuged at 12,000 rpm for 10 min. The supernatant was discarded, and the precipitate was re-suspended with CB Buffer containing 5% 3-mercaptoethanol. The solution was vibrated at 37° C. for 30 min, and centrifuged at 12,000 rpm for 10 min. The supernatant was dialyzed in PB5.8 Buffer system (including 300 mM NaCl and 50 mMEDTA). The buffer was changed every 4 hr. After the buffer was changed for 3 times, the dialyzed solution was collected and centrifuged at 12,000 rpm for 10 min. The purity of the supernatant sample was examined with SDS-PAGE.

Test of the Activities of Fusion Proteins HBc-DG1, HBc-DG2, HBc-DG3 and HBc-DG5

96-well plates were coated with the preliminarily purified fusion proteins HBc-DG1, HBc-DG2, HBc-DG3 and HBc-DG5 at the concentration of 10 μg/ml for 2 hr at 37° C. Then, the plates were washed once, treated with Flu A blocking buffer at 37° C. for 2 hr and then at 4° C. overnight to block non-specific binding sites. After the blocking buffer was discarded, 100 μl of different enzyme-labeled antibodies were added into each well, including 8G9-HRP, 8H5-HRP and 8C11-HRP. Among them, the 8C11-HRP was a specific antibody against the 239 protein, and the 8G9-HRP was the monoclonal antibody used to screen the 12aa peptide. The plates were incubated with antibodies at 37° C. for 30 min, and washed with PBST for 5 times. Color was developed for 10 min with the addition of color developing solution and the reaction was terminated with the stopping buffer. The results shown in FIG. 4 were read with a microplate reader. It could be known from the results of FIG. 4 that only HBc-DG3 reacted with 8G9-HRP, but the value of reaction was relatively low, indicating that on the HBc vector protein, the 12aa peptide fragments G1, G2, G3 and G5 obtained through 8G9 screening could not display the activity of the corresponding peptide fragments on the phage.

Example 8

Competitive ELISA Assay of Synthetic Peptides G1, G2, G3, G5 with Avian Influenza Virus The plate was coated with mouse monoclonal antibody 2F2 specific for avian influenza virus at the concentration of 10 μg/ml. 1:40 diluted virus strain Ck/HK/Yu22/02 was added to the well containing plates and incubated at 37° C. for 1 hr. After the virus in the wells was discarded, synthetic peptides G1, G2, G3, and G5 of different concentration gradient and 1:1,000 diluted 8G9/HRP were added to the wells together and incubated at 37° C. for 30 min. Unrelated 12aa peptide was used as negative control, and additionally, PBS was used as negative control not containing synthesized peptide. The plates were washed with PBST for 5 times. Color was developed for 10 min with the addition of color developing solution, and stopping buffer was added to terminate the reaction. The value was read with a microplate reader. As the competition rate reached 50% and was concentration dependent, the peptide could compete with avian influenza virus to bind the 8G9 enzyme-labeled antibody, further indicating that the 12aa peptide might simulate part of the spacial structure of 8G9 antigen epitope. The results was shown in FIG. 5, from which it could be known that G2 synthetic peptide had competition activity when its concentration was 50 ug.

Example 9

Using the Avian Influenza Monoclonal Antibody to Screen for Ligands Specifically Binding to Avian Influenza HA Protein 96-well plate was coated with HA-type avian influenza monoclonal antibody to further capture the avian influenza virus. Then, the virus was incubated with appropriate amount of phage peptide library. Non-binding phages and large numbers of substances bound non-specifically were removed. Phage peptides specifically binding to the HA protein were competitively eluted with broad-spectrum neutralizing monoclonal antibody or ascites. The phage peptides were then tested with hemagglutinin inhibition or competitive ELISA to select 12aa peptides binding to the HA protein in competition with broad-spectrum neutralizing monoclonal antibody, which could be used for therapeutic treatment of avian influenza.

The virus-capturing effect was good when the plate was coated with avian influenza monoclonal antibodies 2F2 and 3G4 mixed with the amount of 2 ug/ml. At the amount of 20 HA/well, the subtype HA avian influenza viruses yu22 and 6151 bound completely with the coating antibody. 5 μl of the phage original peptide library ($2\times10^{13}$ pfu) was diluted in 1 ml TBST, which was added equally into 10 wells with 100 ul/well, and incubated at 37 for 1 h. The wells were washed in the first round with TBST (0.1%) for 3 times and then with TBST (0.5%) for 5-8 times. Appropriate amount of the mixture of avian influenza antibodies 8H5, 8G9 and 13D4 was used for competitive elution. The above-mentioned procedures were repeated till the third round of screening, then the selected substance was titrated and single-colony phage plaques were selected and amplified to perform hemagglutinin inhibition or competitive ELISA assay, in which they competed with 8H5, 8G9 and 13D4 for virus binding site. The 12aa peptides binding to the HA protein in competition with broad-spectrum neutralizing monoclonal antibody were selected.

Example 9

HI Blocking Test of the Synthetic Peptides G1, G2, G3 and G5

The concentration of Ck/HKYU22/02 virus was adjusted to appropriate level according to ordinary HI method. 25 ug synthetic peptide was proportionally diluted to $1/2^8$. Each diluted gradient was mixed in duplicate with 1:500 diluted 8G9 ascites. 50 μl chicken red blood cells were added after the mixture was incubated in the well with the virus Ck/HKYU22/02 for 0.5 h at room temperature. The HI blocking effect of the synthetic peptides was observed and the result is shown in FIG. 6. G2 polypeptide could clearly block the HI activity of antibody for the virus, indicating that the G2 peptide might mimic the 8G9 mAb binding site on virus, while the other polypeptides had no HI blocking effect.

```
8G9 VH: Nucleotide sequence:
                                              SEQ ID NO: 1
   CAGGTCCAACTGCTGCAGCCTGGGGTTGAGCTGGTGAGGCCGGGGGC

TTCAGTGAAGCTGTCCTGCAAGGCTTCTGGCTACACGTTCACCAGCTTCT

GGATGAACTGGGTTAAACAGAGGCCTGACCAAGGCCTTGAGTGGATTGGA

AGGATTGATCCTTACGATAGTGAAACTCACTACAATCAAAAATTCAAGGA

CAAGGCCATATTGACTGTAGACAAATCCTCCAGCACAGCCTACATGCAAC

TCAGCAGCCTGACATCTGAGGACTCTGCGGTCTATTACTGTGGAAGAGGC

ATTGCTACATTAATGGTTCTACCTGACTACTGGGGTCAAGGCACCACGGT

CACCGAATCTCTAGAGGATCCCCGGGTACCGAGCTCGAAtTCGTAA

8G9 VH Amino acid sequence:
                                              SEQ ID NO: 2
   QVQLLQPGVELVRPGASVKLSCKASGYTFTSFWMNWVKQRPDQGLEW

IGRIDPYDSETHYNQKFKDKAILTVDKSSSTAYMQLSSLTSEDSAVYYCG

RGIATLMVLPDYWGQGTTVTESLEDPRVPSSNS

8G9VK: Nucleotide sequence
                                              SEQ ID NO: 3
   GACATCCTGATGACCCAATCTCCATCCTCCATGTCTGTATCTCTGGG

AGACACAGTCAGCATCACTTGCCATGCAAGTCAGGACATTAGCAGTAATA

TGGGGTGGTTGCAGCAGAAACCAGGGAAGTCATTGAAGGGCCTGATCTAT

CATGGAACCAACTTGGAAGATGGAGTTCCTTCAAGGTTCAGTGGCAGTGG

GTCTGGACCAGATTATTCTCTCACCATCAGCAGCCTGGAATCTGAAGATT

TTGCAGACTATTACTGTGTACAGTATATTCAGTTTCCGTGGACGTTCGGT

GGAGGCACCAAGCTGGAGATCAAACGGGCT

8G9VK Amino acid sequence:
                                              SEQ ID NO: 4
   DILMTQSPSSMSVSLGDTVSITCHASQDISSNMGWLQQKPGKSLKGL
```

-continued

IYHGTNLEDGVPSRFSGSGSGPDYSLTISSLESEDFADYYCVQYIQFPWT

FGGGTKLEIKRA

13D4VH: Nucleotide sequence

SEQ ID NO: 5

CAGGTTCAGCTGCAGCAGTCCGGAGCTGAGCTGATGAAGCCTGGGGC

CTCAGTGAAGATATCCTGCAAGGCTACTGGCTACACATTCAGTGGGCACT

GGATAGAGTGGGTAAAGCAGAGGCCTGGACATGGCCTTGAGTGGATTGGA

GAGATTTTACCTGGAAGTGGTAATATTCACTATAATGAGAAGTTTAAGGG

CAAGGCCACATTCGCTGCAGATACATCCTCCAACACAGCCTACATGCAAC

TCAGCAGCCTGACATCTGAGGACTCTGCCGTCTATTACTGTGCAAGATTG

GGTACTACGGCAGTAGAGAGGGACTGGTACTTCGATGTCTGGGGCCAAGG

GACCACGGTCACCGAATCTCTAGAGGATCCCCGGGTACCGAGCTCGAATT

CG

13D4VH Amino acid sequence:

SEQ ID NO: 6

QVQLQQSGAELMKPGASVKISCKATGYTFSGHWIEWVKQRPGHGLEW

IGEILPGSGNIHYNEKFKGKATFAADTSSNTAYMQLSSLTSEDSAVYYCA

RLGTTAVERDWYFDVWGQGTTVTESLEDPRVPSSNS

13D4VK: Nucleotide sequence

SEQ ID NO: 7

GACATTGTGATGACCCAGTCTCAAAAATTCATGTCCGCATCAGTAGG

AGACAGGGTCAGCGTCACCTGCAAGGCCAGTCAGAATGTGGGTACTCATT

TAGCCTGGTATCAACAGAAACCAGGTCAATCTCCGAAAGCACTGATTTAC

TCGGCATCCTACCGGTACAGTGGAGTCCCTGATCGCTTCACAGGCAGTGG

ATCTGGGACAGATTTCACTCTCACCATCAGCAATGTGCAGTCTGGAGACT

TGGCAGACTATTTCTGTCAGCAATATAACAACTTTCCGCTCACGTTCGGT

GCTGGCACCAAGCTGGAAATAAAACGG

13D4VK Amino acid sequence:

SEQ ID NO: 8

DIVMTQSQKFMSASVGDRVSVTCKASQNVGTHLAWYQQKPGQSPKAL

IYSASYRYSGVPDRFTGSGSGTDFTLTISNVQSGDLADYFCQQYNNFPLT

FGAGTKLEIKR

20A11 VH Nucleotide sequence:

SEQ ID NO: 9

CAGGTTCAGCTGCAGCAGTCTGGAGCTGAGCTGATGAAGCCTGGGGC

CTCAGTGAAGATATCCTGCAAGGCTACTGGCTACACATTCAGTGGGCACT

GGATAGAGTGGGTAAAGCAGAGGCCTGGACATGGCCTTGAGTGGATTGGA

GAGATTTTACCTGGAAGTGGTAATATTCACTATAATGAGAAGTTTAAGGG

CAAGGCCACATTCGCTGCAGATACATCCTCCAACACAGCCTACATGCAAC

TCAGCAGCCTGACATCTGAGGACTCTGCCGTCTATTACTGTGCAAGATTG

GGTACTACGGCAGTAGAGAGGGACTGGTACTTCGATGTCTGGGGCCAAGG

AACCTCCGTGACCGTGTCCTCC

20A11 VH Amino acid sequence:

SEQ ID NO: 10

QVQLQQSGAELMKPGASVKISCKATGYTFSGHWIEWVKQRPGHGLEW

IGEILPGSGNIHYNEKFKGKATFAADTSSNTAYMQLSSLTSEDSAVYYCA

RLGTTAVERDWYFDVWGQGTSVTVSS

-continued

13D4VK: Nucleotide sequence

SEQ ID NO: 11

GACATTGTGATGACCCAGTCTCAAAAATTCATGTCCGCATCAGTAGG

AGACAGGGTCAGCGTCACCTGCAAGGCCAGTCAGAATGTGGGTACTCATT

TAGCCTGGTATCAACAGAAACCAGGTCAATCTCCGAAAGCACTGATTTAC

TCGGCATCCTACCGGTACAGTGGAGTCCCTGATCGCTTCACAGGCAGTGG

ATCTGGGACAGATTTCACTCTCACCATCAGCAATGTGCAGTCTGGAGACT

TGGCAGACTATTTCTGTCAGCAATATAACAACTTTCCGCTCACGTTCGGT

GCTGGCACCAAGCTGGAAATAAAACGG

13D4VK Amino acid sequence:

SEQ ID NO: 12

DIVMTQSQKFMSASVGDRVSVTCKASQNVGTHLAWYQQKPGQSPKAL

IYSASYRYSGVPDRFTGSGSGTDFTLTISNVQSGDLADYFCQQYNNFPLT

FGAGTKLEIKR

8G9 VH Mutated nucleotide sequence

SEQ ID NO: 41

CAGGTCCAACTGCAGCAGCCTGGGGTTGAGCTGGTGAGGCCGGGGGC

TTCAGTGAAGCTGTCCTGCAAGGCTTCTGGCTACACGTTCACCAGCTTCT

GGATGAACTGGGTTAAACAGAGGCCTGACCAAGGCCTTGAGTGGATTGGA

AGGATTGATCCTTACGATAGTGAAACTCACTACAATCAAAAATTCAAGGA

CAAGGCCATATTGACTGTAGACAAATCCTCCAGCACAGCCTACATGCAAC

TCAGCAGCCTGACATCTGAGGACTCTGCGGTCTATTACTGTGGAAGAGGC

ATTGCTACATTAATGGTTCTACCTGACTACTGGGGTCAAGGCACCTCCGT

GACCGTGTCCTCC

8G9 VH Mutated amino acid sequence

SEQ ID NO: 42

QVQLQQPGVELVRPGASVKLSCKASGYTFTSFWMNWVKQRPDQGLEW

IGRIDPYDSETHYNQKFKDKAILTVDKSSSTAYMQLSSLTSEDSAVYYCG

RGIATLMVLPDYWGQGTSVTVSS

13D4VH-SV Mutated nucleotide sequence:

SEQ ID NO: 43

CAGGTTCAGCTGCAGCAGTCTGGAGCTGAGCTGATGAAGCCTGGGGC

CTCAGTGAAGATATCCTGCAAGGCTACTGGCTACACATTCAGTGGGCACT

GGATAGAGTGGGTAAAGCAGAGGCCTGGACATGGCCTTGAGTGGATTGGA

GAGATTTTACCTGGAAGTGGTAATATTCACTATAATGAGAAGTTTAAGGG

CAAGGCCACATTCGCTGCAGATACATCCTCCAACACAGCCTACATGCAAC

TCAGCAGCCTGACATCTGAGGACTCTGCCGTCTATTACTGTGCAAGATTG

GGTACTACGGCAGTAGAGAGGGACTGGTACTTCGATGTCTGGGGCCAAGG

AACCTCCGTGACCGTGTCCTCC

13D4VH-SV Mutated amino acid sequence:

SEQ ID NO: 44

QVQLQQSGAELMKPGASVKISCKATGYTFSGHWIEWVKQRPGHGLEW

IGEILPGSGNIHYNEKFKGKATFAADTSSNTAYMQLSSLTSEDSAVYYCA

RLGTTAVERDWYFDVWGQGTSVTVSS

13D4VH-LV Mutated nucleotide sequence:

SEQ ID NO: 45

CAGGTTCAGCTGCAGCAGTCTGGAGCTGAGCTGATGAAGCCTGGGGC

-continued

CTCAGTGAAGATATCCTGCAAGGCTACTGGCTACACATTCAGTGGGCACT

GGATAGAGTGGGTAAAGCAGAGGCCTGGACATGGCCTTGAGTGGATTGGA

GAGATTTTACCTGGAAGTGGTAATATTCACTATAATGAGAAGTTTAAGGG

CAAGGCCACATTCGCTGCAGATACATCCTCCAACACAGCCTACATGCAAC

TCAGCAGCCTGACATCTGAGGACTCTGCCGTCTATTACTGTGCAAGATTG

GGTACTACGGCAGTAGAGAGGGACTGGTACTTCGATGTCTGGGGCCAAGG

-continued

AACCCTGGTGACCGTGTCCTCC

13D4VH-LV Mutated amino acid sequence:

SEQ ID NO: 46

QVQLQQSGAELMKPGASVKISCKATGYTFSGHWIEWVKQRPGHGLEW

IGEILPGSGNIHYNEKFKGKATFAADTSSNTAYMQLSSLTSEDSAVYYCA

RLGTTAVERDWYFDVWGQGTLVTVSS

The invention claimed is:

1. A monoclonal antibody which binds specifically to an avian influenza virus (AIV) subtype H5 hemagglutinin (HA), wherein said monoclonal antibody comprises a variable heavy chain comprising a first CDR1-CDR3 having an amino acid sequence as set forth in SEQ ID NOs: 19-21; and a variable light chain comprising a second CDR1-CDR3 having an amino acid sequence as set forth in SEQ ID NOs: 22-24.

2. The monoclonal antibody according to claim 1, wherein said variable heavy chain comprises an amino acid sequence selected from the group consisting of: SEQ ID NO: 6, SEQ ID NO: 10, SEQ ID NO: 44 and SEQ ID NO: 46.

3. The monoclonal antibody according to claim 1, wherein said variable light chain comprises an amino acid sequence selected from the group consisting of: SEQ ID NO: 8 and SEQ ID NO: 12.

4. The monoclonal antibody according to claim 1, wherein said monoclonal antibody is Fab, Fab', F(ab)2 or Fv.

5. The monoclonal antibody according to claim 1, wherein said monoclonal antibody comprises a non-CDR region which is from a species that is not murine.

6. The monoclonal antibody according to claim 5, wherein said non-CDR region is from a human antibody.

7. The monoclonal antibody according to claim 6, wherein one or more amino acids of said human non-CDR region are substituted by corresponding amino acids from a murine antibody.

8. A monoclonal antibody according to claim 1, wherein said monoclonal antibody is selected from the group consisting of:

(i) a monoclonal antibody generated by hybridoma cell strain 13D4 which is deposited under the accession number of CCTCC-C200721; and (ii) a monoclonal antibody generated by hybridoma cell strain 20A11 which is deposited under the accession number of CCTCC-C200638.

9. A hybridoma cell strain selected from the group consisting of:

(i) hybridoma cell strain 13D4 which is deposited under the accession number of CCTCC-C200721; and (ii) hybridoma cell strain 20A11 which is deposited under the accession number of CCTCC-C200638.

10. An isolated nucleic acid molecule, comprising a nucleic acid sequence encoding an antibody heavy chain variable region, said antibody heavy chain variable region comprising CDR1-CDR3 having an amino acid sequence as set forth in SEQ ID NOs: 19-21.

11. The isolated nucleic acid molecule according to claim 10, wherein said heavy chain variable region comprises an amino acid sequence selected from the group consisting of: SEQ ID NO: 6, SEQ ID NO: 10, SEQ ID NO: 44 and SEQ ID NO: 46.

12. The isolated nucleic acid molecule according to claim 11, wherein said nucleic acid molecule comprises a nucleic acid sequence selected from the group consisting of: SEQ ID NO: 5, SEQ ID NO: 9, SEQ ID NO: 43 and SEQ ID NO: 45.

13. An isolated nucleic acid molecule, comprising a nucleic acid sequence encoding an antibody light chain variable region, said antibody light chain variable region comprising CDR1-CDR3 having an amino acid sequence as set forth in SEQ ID NOs: 22-24.

14. The isolated nucleic acid molecule according to claim 13, wherein said light chain variable region comprises an amino acid sequence selected from the group consisting of: SEQ ID NO: 8 and SEQ ID NO: 12.

15. The isolated nucleic acid molecule according to claim 14, wherein said nucleic acid molecule comprises a nucleic acid sequence selected from the group consisting of: SEQ ID NO: 7 and SEQ ID NO: 11.

16. A method for detecting an avian influenza virus subtype H5 in a sample, comprising the following steps a) contacting said sample with the monoclonal antibody according to claim 1; and b) detecting the reaction of the monoclonal antibody with said virus.

17. The method according to claim 16, wherein said monoclonal antibody is attached to a solid phase.

18. A pharmaceutical composition which comprises the monoclonal antibody of claim 1 or a pharmaceutically acceptable salt thereof.

19. A method for preventing or treating a disease caused by an avian influenza virus infection in a subject, comprising administering to said subject an effective dose of the pharmaceutical composition of claim 18.

20. The composition for detecting an avian influenza virus (AIV) in a sample, comprising the monoclonal antibody of claim 1 that is attached to a solid phase substrate.

21. A kit for detecting an avian influenza virus in a sample comprising the monoclonal antibody of claim 1 attached to a solid phase substrate, and a detectably labeled secondary monoclonal antibody.

* * * * *

UNITED STATES PATENT AND TRADEMARK OFFICE

CERTIFICATE OF CORRECTION

PATENT NO. : 8,603,467 B2
APPLICATION NO. : 12/664696
DATED : December 10, 2013
INVENTOR(S) : Chen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 489 days.

Signed and Sealed this
Twenty-second Day of September, 2015

Michelle K. Lee
*Director of the United States Patent and Trademark Office*

SEQUENCE LISTING

<160> NUMBER OF SEQ ID NOS: 96

<210> SEQ ID NO 1
<211> LENGTH: 393
<212> TYPE: DNA
<213> ORGANISM: Mus musculus

<400> SEQUENCE: 1

```
caggtccaac tgctgcagcc tggggttgag ctggtgaggc cggggcttc agtgaagctg     60

tcctgcaagg cttctggcta cacgttcacc agcttctgga tgaactgggt taaacagagg    120

cctgaccaag gccttgagtg gattggaagg attgatcctt acgatagtga aactcactac    180

aatcaaaaat tcaaggacaa ggccatattg actgtagaca aatcctccag cacagcctac    240

atgcaactca gcagcctgac atctgaggac tctgcggtct attactgtgg aagaggcatt    300

gctacattaa tggttctacc tgactactgg ggtcaaggca ccacggtcac cgaatctcta    360

gaggatcccc gggtaccgag ctcgaattcg taa                                 393
```

<210> SEQ ID NO 2
<211> LENGTH: 130
<212> TYPE: PRT
<213> ORGANISM: Mus musculus

<400> SEQUENCE: 2

```
Gln Val Gln Leu Leu Gln Pro Gly Val Glu Leu Val Arg Pro Gly Ala
1               5                   10                  15

Ser Val Lys Leu Ser Cys Lys Ala Ser Gly Tyr Thr Phe Thr Ser Phe
            20                  25                  30

Trp Met Asn Trp Val Lys Gln Arg Pro Asp Gln Gly Leu Glu Trp Ile
        35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Gly Arg Gly Ile Ala Thr Leu Met Val Leu Pro Asp Tyr Trp Gly Gln
            100                 105                 110

Gly Thr Thr Val Thr Glu Ser Leu Glu Asp Pro Arg Val Pro Ser Ser
        115                 120                 125

Asn Ser
    130
```

<210> SEQ ID NO 3
<211> LENGTH: 327
<212> TYPE: DNA

<213> ORGANISM: Mus musculus

<400> SEQUENCE: 3
gacatcctga tgacccaatc tccatcctcc atgtctgtat ctctgggaga cacagtcagc 60
atcacttgcc atgcaagtca ggacattagc agtaatatgg ggtggttgca gcagaaacca 120
gggaagtcat tgaagggcct gatctatcat ggaaccaact tggaagatgg agttccttca 180
aggttcagtg gcagtgggtc tggaccagat tattctctca ccatcagcag cctggaatct 240
gaagattttg cagactatta ctgtgtacag tatattcagt ttccgtggac gttcggtgga 300
ggcaccaagc tggagatcaa acgggct 327

<210> SEQ ID NO 4
<211> LENGTH: 109
<212> TYPE: PRT
<213> ORGANISM: Mus musculus

<400> SEQUENCE: 4

Asp Ile Leu Met Thr Gln Ser Pro Ser Ser Met Ser Val Ser Leu Gly
1 5 10 15

Asp Thr Val Ser Ile Thr Cys His Ala Ser Gln Asp Ile Ser Ser Asn
20 25 30

Met Gly Trp Leu Gln Gln Lys Pro Gly Lys Ser Leu Lys Gly Leu Ile
35 40 45

Tyr His Gly Thr Asn Leu Glu Asp Gly Val Pro Ser Arg Phe Ser Gly
50 55 60

Ser Gly Ser Gly Pro Asp Tyr Ser Leu Thr Ile Ser Ser Leu Glu Ser
65 70 75 80

Glu Asp Phe Ala Asp Tyr Tyr Cys Val Gln Tyr Ile Gln Phe Pro Trp
85 90 95

Thr Phe Gly Gly Gly Thr Lys Leu Glu Ile Lys Arg Ala
100 105

<210> SEQ ID NO 5
<211> LENGTH: 399
<212> TYPE: DNA
<213> ORGANISM: Mus musculus

<400> SEQUENCE: 5
caggttcagc tgcagcagtc cggagctgag ctgatgaagc ctggggcctc agtgaagata 60
tcctgcaagg ctactggcta cacattcagt gggcactgga tagagtgggt aaagcagagg 120
cctggacatg gccttgagtg gattggagag attttacctg gaagtggtaa tattcactat 180
aatgagaagt ttaagggcaa ggccacattc gctgcagata catcctccaa cacagcctac 240
atgcaactca gcagcctgac atctgaggac tctgccgtct attactgtgc aagattgggt 300
actacggcag tagagaggga ctggtacttc gatgtctggg gccaagggac cacggtcacc 360
gaatctctag aggatccccg ggtaccgagc tcgaattcg 399

<210> SEQ ID NO 6
<211> LENGTH: 133
<212> TYPE: PRT
<213> ORGANISM: Mus musculus

<400> SEQUENCE: 6

Gln Val Gln Leu Gln Gln Ser Gly Ala Glu Leu Met Lys Pro Gly Ala
1 5 10 15

Ser Val Lys Ile Ser Cys Lys Ala Thr Gly Tyr Thr Phe Ser Gly His
20 25 30

```
Trp Ile Glu Trp Val Lys Gln Arg Pro Gly His Gly Leu Glu Trp Ile
        35                  40                  45

Gly Glu Ile Leu Pro Gly Ser Gly Asn Ile His Tyr Asn Glu Lys Phe
    50                  55                  60

Lys Gly Lys Ala Thr Phe Ala Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Leu Gly Thr Thr Ala Val Glu Arg Asp Trp Tyr Phe Asp Val
            100                 105                 110

Trp Gly Gln Gly Thr Thr Val Thr Glu Ser Leu Glu Asp Pro Arg Val
        115                 120                 125

Pro Ser Ser Asn Ser
    130


<210> SEQ ID NO 7
<211> LENGTH: 324
<212> TYPE: DNA
<213> ORGANISM: Mus musculus

<400> SEQUENCE: 7

gacattgtga tgacccagtc tcaaaaattc atgtccgcat cagtaggaga cagggtcagc      60

gtcacctgca aggccagtca gaatgtgggt actcatttag cctggtatca acagaaacca     120

ggtcaatctc cgaaagcact gatttactcg gcatcctacc ggtacagtgg agtccctgat     180

cgcttcacag gcagtggatc tgggacagat ttcactctca ccatcagcaa tgtgcagtct     240

ggagacttgg cagactattt ctgtcagcaa tataacaact ttccgctcac gttcggtgct     300

ggcaccaagc tggaaataaa acgg                                            324


<210> SEQ ID NO 8
<211> LENGTH: 108
<212> TYPE: PRT
<213> ORGANISM: Mus musculus

<400> SEQUENCE: 8

Asp Ile Val Met Thr Gln Ser Gln Lys Phe Met Ser Ala Ser Val Gly
1               5                   10                  15

Asp Arg Val Ser Val Thr Cys Lys Ala Ser Gln Asn Val Gly Thr His
            20                  25                  30

Leu Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Gly Asp Leu Ala Asp Tyr Phe Cys Gln Gln Tyr Asn Asn Phe Pro Leu
                85                  90                  95

Thr Phe Gly Ala Gly Thr Lys Leu Glu Ile Lys Arg
            100                 105


<210> SEQ ID NO 9
<211> LENGTH: 369
<212> TYPE: DNA
<213> ORGANISM: Mus musculus

<400> SEQUENCE: 9

caggttcagc tgcagcagtc tggagctgag ctgatgaagc ctggggcctc agtgaagata      60
```

```
tcctgcaagg ctactggcta cacattcagt gggcactgga tagagtgggt aaagcagagg    120

cctggacatg gccttgagtg gattggagag attttacctg gaagtggtaa tattcactat    180

aatgagaagt ttaagggcaa ggccacattc gctgcagata catcctccaa cacagcctac    240

atgcaactca gcagcctgac atctgaggac tctgccgtct attactgtgc aagattgggt    300

actacggcag tagagaggga ctggtacttc gatgtctggg gccaaggaac ctccgtgacc    360

gtgtcctcc                                                            369


<210> SEQ ID NO 10
<211> LENGTH: 123
<212> TYPE: PRT
<213> ORGANISM: Mus musculus

<400> SEQUENCE: 10

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Gly His
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Asn Ile His Tyr Asn Glu Lys Phe
    50                  55                  60

Lys Gly Lys Ala Thr Phe Ala Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Leu Gly Thr Thr Ala Val Glu Arg Asp Trp Tyr Phe Asp Val
            100                 105                 110

Trp Gly Gln Gly Thr Ser Val Thr Val Ser Ser
        115                 120


<210> SEQ ID NO 11
<211> LENGTH: 324
<212> TYPE: DNA
<213> ORGANISM: Mus musculus

<400> SEQUENCE: 11

gacattgtga tgacccagtc tcaaaaattc atgtccgcat cagtaggaga cagggtcagc     60

gtcacctgca aggccagtca gaatgtgggt actcatttag cctggtatca acagaaacca    120

ggtcaatctc cgaaagcact gatttactcg gcatcctacc ggtacagtgg agtccctgat    180

cgcttcacag gcagtggatc tgggacagat ttcactctca ccatcagcaa tgtgcagtct    240

ggagacttgg cagactattt ctgtcagcaa tataacaact ttccgctcac gttcggtgct    300

ggcaccaagc tggaaataaa acgg                                           324


<210> SEQ ID NO 12
<211> LENGTH: 108
<212> TYPE: PRT
<213> ORGANISM: Mus musculus

<400> SEQUENCE: 12

Asp Ile Val Met Thr Gln Ser Gln Lys Phe Met Ser Ala Ser Val Gly
1               5                   10                  15

Asp Arg Val Ser Val Thr Cys Lys Ala Ser Gln Asn Val Gly Thr His
            20                  25                  30

Leu Ala Trp Tyr Gln Gln Lys Pro Gly Gln Ser Pro Lys Ala Leu Ile
```

-continued

```
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Gly Asp Leu Ala Asp Tyr Phe Cys Gln Gln Tyr Asn Asn Phe Pro Leu
                85                  90                  95

Thr Phe Gly Ala Gly Thr Lys Leu Glu Ile Lys Arg
            100                 105


<210> SEQ ID NO 13
<211> LENGTH: 4
<212> TYPE: PRT
<213> ORGANISM: Mus musculus

<400> SEQUENCE: 13

Phe Trp Met Asn
1


<210> SEQ ID NO 14
<211> LENGTH: 10
<212> TYPE: PRT
<213> ORGANISM: Mus musculus

<400> SEQUENCE: 14

Arg Ile Asp Pro Tyr Asp Ser Glu Thr His
1               5                   10


<210> SEQ ID NO 15
<211> LENGTH: 11
<212> TYPE: PRT
<213> ORGANISM: Mus musculus

<400> SEQUENCE: 15

Gly Ile Ala Thr Leu Met Val Leu Pro Asp Tyr
1               5                   10


<210> SEQ ID NO 16
<211> LENGTH: 11
<212> TYPE: PRT
<213> ORGANISM: Mus musculus

<400> SEQUENCE: 16

His Ala Ser Gln Asp Ile Ser Ser Asn Met Gly
1               5                   10


<210> SEQ ID NO 17
<211> LENGTH: 7
<212> TYPE: PRT
<213> ORGANISM: Mus musculus

<400> SEQUENCE: 17

His Gly Thr Asn Leu Glu Asp
1               5


<210> SEQ ID NO 18
<211> LENGTH: 9
<212> TYPE: PRT
<213> ORGANISM: Mus musculus

<400> SEQUENCE: 18

Val Gln Tyr Ile Gln Phe Pro Trp Thr
1               5
```

<210> SEQ ID NO 19
<211> LENGTH: 5
<212> TYPE: PRT
<213> ORGANISM: Mus musculus

<400> SEQUENCE: 19

Gly His Trp Ile Glu
1 5

<210> SEQ ID NO 20
<211> LENGTH: 10
<212> TYPE: PRT
<213> ORGANISM: Mus musculus

<400> SEQUENCE: 20

Glu Ile Leu Pro Gly Ser Gly Asn Ile His
1 5 10

<210> SEQ ID NO 21
<211> LENGTH: 14
<212> TYPE: PRT
<213> ORGANISM: Mus musculus

<400> SEQUENCE: 21

Leu Gly Thr Thr Ala Val Glu Arg Asp Trp Tyr Phe Asp Val
1 5 10

<210> SEQ ID NO 22
<211> LENGTH: 11
<212> TYPE: PRT
<213> ORGANISM: Mus musculus

<400> SEQUENCE: 22

Lys Ala Ser Gln Asn Val Gly Thr His Leu Ala
1 5 10

<210> SEQ ID NO 23
<211> LENGTH: 7
<212> TYPE: PRT
<213> ORGANISM: Mus musculus

<400> SEQUENCE: 23

Ser Ala Ser Tyr Arg Tyr Ser
1 5

<210> SEQ ID NO 24
<211> LENGTH: 9
<212> TYPE: PRT
<213> ORGANISM: Mus musculus

<400> SEQUENCE: 24

Gln Gln Tyr Asn Asn Phe Pro Leu Thr
1 5

<210> SEQ ID NO 25
<211> LENGTH: 5
<212> TYPE: PRT
<213> ORGANISM: Mus musculus

<400> SEQUENCE: 25

Gly His Trp Ile Glu
1 5

<210> SEQ ID NO 26
<211> LENGTH: 10

<212> TYPE: PRT
<213> ORGANISM: Mus musculus

<400> SEQUENCE: 26

Glu Ile Leu Pro Gly Ser Gly Asn Ile His
1 5 10

<210> SEQ ID NO 27
<211> LENGTH: 14
<212> TYPE: PRT
<213> ORGANISM: Mus musculus

<400> SEQUENCE: 27

Leu Gly Thr Thr Ala Val Glu Arg Asp Trp Tyr Phe Asp Val
1 5 10

<210> SEQ ID NO 28
<211> LENGTH: 11
<212> TYPE: PRT
<213> ORGANISM: Mus musculus

<400> SEQUENCE: 28

Lys Ala Ser Gln Asn Val Gly Thr His Leu Ala
1 5 10

<210> SEQ ID NO 29
<211> LENGTH: 7
<212> TYPE: PRT
<213> ORGANISM: Mus musculus

<400> SEQUENCE: 29

Ser Ala Ser Tyr Arg Tyr Ser
1 5

<210> SEQ ID NO 30
<211> LENGTH: 9
<212> TYPE: PRT
<213> ORGANISM: Mus musculus

<400> SEQUENCE: 30

Gln Gln Tyr Asn Asn Phe Pro Leu Thr
1 5

<210> SEQ ID NO 31
<211> LENGTH: 12
<212> TYPE: PRT
<213> ORGANISM: Artificial
<220> FEATURE:
<223> OTHER INFORMATION: A peptide binding to monoclonal antibody 8G9

<400> SEQUENCE: 31

Leu Pro Tyr Tyr Asp Pro Arg Ala Leu Leu Leu Arg
1 5 10

<210> SEQ ID NO 32
<211> LENGTH: 12
<212> TYPE: PRT
<213> ORGANISM: Artificial
<220> FEATURE:
<223> OTHER INFORMATION: A peptide binding to monoclonal antibody 8G9

<400> SEQUENCE: 32

His Thr Pro Cys Asp Thr Arg Asp Cys Val Leu Arg
1 5 10

<210> SEQ ID NO 33

<211> LENGTH: 12
<212> TYPE: PRT
<213> ORGANISM: Artificial
<220> FEATURE:
<223> OTHER INFORMATION: A peptide binding to monoclonal antibody 8G9

<400> SEQUENCE: 33

His Pro Pro Cys Asp Thr Arg Asp Cys Val Leu Arg
1 5 10

<210> SEQ ID NO 34
<211> LENGTH: 12
<212> TYPE: PRT
<213> ORGANISM: Artificial
<220> FEATURE:
<223> OTHER INFORMATION: A peptide binding to monoclonal antibody 8G9

<400> SEQUENCE: 34

Ala Pro Ala Cys Asp Ser Arg Leu Cys Val Leu Arg
1 5 10

<210> SEQ ID NO 35
<211> LENGTH: 12
<212> TYPE: PRT
<213> ORGANISM: Artificial
<220> FEATURE:
<223> OTHER INFORMATION: A peptide binding to monoclonal antibody 8G9

<400> SEQUENCE: 35

Gly Asp Thr Arg Ser Phe Tyr Tyr Lys Leu Tyr Phe
1 5 10

<210> SEQ ID NO 36
<211> LENGTH: 12
<212> TYPE: PRT
<213> ORGANISM: Artificial
<220> FEATURE:
<223> OTHER INFORMATION: A peptide binding to monoclonal antibody 8G9

<400> SEQUENCE: 36

Leu Pro His Ala Ser Pro Arg Ala Leu Val Met Arg
1 5 10

<210> SEQ ID NO 37
<211> LENGTH: 12
<212> TYPE: PRT
<213> ORGANISM: Artificial
<220> FEATURE:
<223> OTHER INFORMATION: A peptide binding to monoclonal antibody 8G9

<400> SEQUENCE: 37

Thr Thr Ala Ser Asn Ser Lys Pro Pro Leu His Asp
1 5 10

<210> SEQ ID NO 38
<211> LENGTH: 12
<212> TYPE: PRT
<213> ORGANISM: Artificial
<220> FEATURE:
<223> OTHER INFORMATION: A peptide binding to monoclonal antibody 8G9

<400> SEQUENCE: 38

Gly Pro Trp Glu Asn Leu Arg Ala Leu Phe Leu Arg
1 5 10

<210> SEQ ID NO 39
<211> LENGTH: 12
<212> TYPE: PRT

<213> ORGANISM: Artificial
<220> FEATURE:
<223> OTHER INFORMATION: A peptide binding to monoclonal antibody 8G9

<400> SEQUENCE: 39

Asp Val Ile Tyr Val Asp Arg Trp His Ile Leu Arg
1               5                   10

<210> SEQ ID NO 40
<211> LENGTH: 11
<212> TYPE: PRT
<213> ORGANISM: Artificial
<220> FEATURE:
<223> OTHER INFORMATION: A peptide binding to monoclonal antibody 8G9

<400> SEQUENCE: 40

Ser Gly Tyr Ser Ser Arg Met Asp Phe Leu Arg
1               5                   10

<210> SEQ ID NO 41
<211> LENGTH: 360
<212> TYPE: DNA
<213> ORGANISM: Artificial
<220> FEATURE:
<223> OTHER INFORMATION: 8G9 VH Mutated nucleotide sequence

<400> SEQUENCE: 41
caggtccaac tgcagcagcc tggggttgag ctggtgaggc cgggggcttc agtgaagctg 60
tcctgcaagg cttctggcta cacgttcacc agcttctgga tgaactgggt taaacagagg 120
cctgaccaag gccttgagtg gattggaagg attgatcctt acgatagtga aactcactac 180
aatcaaaaat tcaaggacaa ggccatattg actgtagaca aatcctccag cacagcctac 240
atgcaactca gcagcctgac atctgaggac tctgcggtct attactgtgg aagaggcatt 300
gctacattaa tggttctacc tgactactgg ggtcaaggca cctccgtgac cgtgtcctcc 360

<210> SEQ ID NO 42
<211> LENGTH: 120
<212> TYPE: PRT
<213> ORGANISM: Artificial
<220> FEATURE:
<223> OTHER INFORMATION: 8G9 VH Mutated amino acid sequence

<400> SEQUENCE: 42

Gln Val Gln Leu Gln Gln Pro Gly Val Glu Leu Val Arg Pro Gly Ala
1               5                   10                  15

Ser Val Lys Leu Ser Cys Lys Ala Ser Gly Tyr Thr Phe Thr Ser Phe
            20                  25                  30

Trp Met Asn Trp Val Lys Gln Arg Pro Asp Gln Gly Leu Glu Trp Ile
        35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Gly Arg Gly Ile Ala Thr Leu Met Val Leu Pro Asp Tyr Trp Gly Gln
            100                 105                 110

Gly Thr Ser Val Thr Val Ser Ser
        115                 120

<210> SEQ ID NO 43

<211> LENGTH: 369
<212> TYPE: DNA
<213> ORGANISM: Artificial
<220> FEATURE:
<223> OTHER INFORMATION: 13D4VH-SV Mutated nucleotide sequence

<400> SEQUENCE: 43
caggttcagc tgcagcagtc tggagctgag ctgatgaagc ctggggcctc agtgaagata 60
tcctgcaagg ctactggcta cacattcagt gggcactgga tagagtgggt aaagcagagg 120
cctggacatg gccttgagtg gattggagag attttacctg gaagtggtaa tattcactat 180
aatgagaagt ttaagggcaa ggccacattc gctgcagata catcctccaa cacagcctac 240
atgcaactca gcagcctgac atctgaggac tctgccgtct attactgtgc aagattgggt 300
actacggcag tagagaggga ctggtacttc gatgtctggg gccaaggaac ctccgtgacc 360
gtgtcctcc 369

<210> SEQ ID NO 44
<211> LENGTH: 123
<212> TYPE: PRT
<213> ORGANISM: Artificial
<220> FEATURE:
<223> OTHER INFORMATION: 13D4VH-SV Mutated amino acid sequence

<400> SEQUENCE: 44

Gln Val Gln Leu Gln Gln Ser Gly Ala Glu Leu Met Lys Pro Gly Ala
1 5 10 15

Ser Val Lys Ile Ser Cys Lys Ala Thr Gly Tyr Thr Phe Ser Gly His
20 25 30

Trp Ile Glu Trp Val Lys Gln Arg Pro Gly His Gly Leu Glu Trp Ile
35 40 45

Gly Glu Ile Leu Pro Gly Ser Gly Asn Ile His Tyr Asn Glu Lys Phe
50 55 60

Lys Gly Lys Ala Thr Phe Ala Ala Asp Thr Ser Ser Asn Thr Ala Tyr
65 70 75 80

Met Gln Leu Ser Ser Leu Thr Ser Glu Asp Ser Ala Val Tyr Tyr Cys
85 90 95

Ala Arg Leu Gly Thr Thr Ala Val Glu Arg Asp Trp Tyr Phe Asp Val
100 105 110

Trp Gly Gln Gly Thr Ser Val Thr Val Ser Ser
115 120

<210> SEQ ID NO 45
<211> LENGTH: 369
<212> TYPE: DNA
<213> ORGANISM: Artificial
<220> FEATURE:
<223> OTHER INFORMATION: 13D4VH-LV Mutated nucleotide sequence

<400> SEQUENCE: 45
caggttcagc tgcagcagtc tggagctgag ctgatgaagc ctggggcctc agtgaagata 60
tcctgcaagg ctactggcta cacattcagt gggcactgga tagagtgggt aaagcagagg 120
cctggacatg gccttgagtg gattggagag attttacctg gaagtggtaa tattcactat 180
aatgagaagt ttaagggcaa ggccacattc gctgcagata catcctccaa cacagcctac 240
atgcaactca gcagcctgac atctgaggac tctgccgtct attactgtgc aagattgggt 300
actacggcag tagagaggga ctggtacttc gatgtctggg gccaaggaac cctggtgacc 360
gtgtcctcc 369

<210> SEQ ID NO 46
<211> LENGTH: 123
<212> TYPE: PRT
<213> ORGANISM: Artificial
<220> FEATURE:
<223> OTHER INFORMATION: 13D4VH-LV Mutated amino acid sequence

<400> SEQUENCE: 46

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Gly His
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Asn Ile His Tyr Asn Glu Lys Phe
    50                  55                  60

Lys Gly Lys Ala Thr Phe Ala Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Leu Gly Thr Thr Ala Val Glu Arg Asp Trp Tyr Phe Asp Val
            100                 105                 110

Trp Gly Gln Gly Thr Leu Val Thr Val Ser Ser
        115                 120
```

<210> SEQ ID NO 47
<211> LENGTH: 25
<212> TYPE: DNA
<213> ORGANISM: Artificial
<220> FEATURE:
<223> OTHER INFORMATION: A primer

<400> SEQUENCE: 47
ttacatatgc aggtccaact gctgc 25

<210> SEQ ID NO 48
<211> LENGTH: 48
<212> TYPE: DNA
<213> ORGANISM: Artificial
<220> FEATURE:
<223> OTHER INFORMATION: A primer

<400> SEQUENCE: 48
gctaccaccc cctccagatc cgccacctcc agagattcgg tgaccgtg 48

<210> SEQ ID NO 49
<211> LENGTH: 52
<212> TYPE: DNA
<213> ORGANISM: Artificial
<220> FEATURE:
<223> OTHER INFORMATION: A primer

<400> SEQUENCE: 49
atctggaggg ggtggtagcg gtggaggcgg gagtgacatc ctgatgaccc aa 52

<210> SEQ ID NO 50
<211> LENGTH: 29
<212> TYPE: DNA
<213> ORGANISM: Artificial
<220> FEATURE:
<223> OTHER INFORMATION: A primer

<400> SEQUENCE: 50

-continued ttagaattcc tacccgtttg atctccagc 29

<210> SEQ ID NO 51
<211> LENGTH: 25
<212> TYPE: DNA
<213> ORGANISM: Artificial
<220> FEATURE:
<223> OTHER INFORMATION: A primer

<400> SEQUENCE: 51
ttacatatgc aggttcagct gcagc 25

<210> SEQ ID NO 52
<211> LENGTH: 45
<212> TYPE: DNA
<213> ORGANISM: Artificial
<220> FEATURE:
<223> OTHER INFORMATION: A primer

<400> SEQUENCE: 52
gctaccaccc cctccagatc cgccacctcc cgaattcgag ctcgg 45

<210> SEQ ID NO 53
<211> LENGTH: 49
<212> TYPE: DNA
<213> ORGANISM: Artificial
<220> FEATURE:
<223> OTHER INFORMATION: A primer

<400> SEQUENCE: 53
atctggaggg ggtggtagcg gtggaggcgg gagtgacatt gtgatgacc 49

<210> SEQ ID NO 54
<211> LENGTH: 29
<212> TYPE: DNA
<213> ORGANISM: Artificial
<220> FEATURE:
<223> OTHER INFORMATION: A primer

<400> SEQUENCE: 54
ttagaattcc cgttttattt ccagcttgg 29

<210> SEQ ID NO 55
<211> LENGTH: 59
<212> TYPE: DNA
<213> ORGANISM: Artificial
<220> FEATURE:
<223> OTHER INFORMATION: A primer

<400> SEQUENCE: 55
cctgctactg attgtccctg catatgtcct gtcccaggtc caactgcagc agcctgggg 59

<210> SEQ ID NO 56
<211> LENGTH: 50
<212> TYPE: DNA
<213> ORGANISM: Artificial
<220> FEATURE:
<223> OTHER INFORMATION: A primer

<400> SEQUENCE: 56
tttggatcca tgggaaggct tacttcttca ttcctgctac tgattgtccc 50

<210> SEQ ID NO 57
<211> LENGTH: 43
<212> TYPE: DNA
<213> ORGANISM: Artificial
<220> FEATURE:

<223> OTHER INFORMATION: A primer

<400> SEQUENCE: 57
tttctcgagg gaggatacgg tcacggaggt gccttgaccc cag 43

<210> SEQ ID NO 58
<211> LENGTH: 51
<212> TYPE: DNA
<213> ORGANISM: Artificial
<220> FEATURE:
<223> OTHER INFORMATION: A primer

<400> SEQUENCE: 58
gctgctgctg tggcttacag atgcaagatg tgacatcctg atgacccaat c 51

<210> SEQ ID NO 59
<211> LENGTH: 56
<212> TYPE: DNA
<213> ORGANISM: Artificial
<220> FEATURE:
<223> OTHER INFORMATION: A primer

<400> SEQUENCE: 59
tttgaattca tgtctgtgcc aactcaggtc ctggggttgc tgctgctgtg gcttac 56

<210> SEQ ID NO 60
<211> LENGTH: 27
<212> TYPE: DNA
<213> ORGANISM: Artificial
<220> FEATURE:
<223> OTHER INFORMATION: A primer

<400> SEQUENCE: 60
tttctcgaga gcccgtttga tctccag 27

<210> SEQ ID NO 61
<211> LENGTH: 53
<212> TYPE: DNA
<213> ORGANISM: Artificial
<220> FEATURE:
<223> OTHER INFORMATION: A primer

<400> SEQUENCE: 61
tcctgctact gattgtccct gcatatgtcc tgtcccaggt tcagctgcag cag 53

<210> SEQ ID NO 62
<211> LENGTH: 52
<212> TYPE: DNA
<213> ORGANISM: Artificial
<220> FEATURE:
<223> OTHER INFORMATION: A primer

<400> SEQUENCE: 62
tttggatcca tgggaaggct tacttcttca ttcctgctac tgattgtccc tg 52

<210> SEQ ID NO 63
<211> LENGTH: 49
<212> TYPE: DNA
<213> ORGANISM: Artificial
<220> FEATURE:
<223> OTHER INFORMATION: A primer

<400> SEQUENCE: 63
ttttctcgag ggaggacacg gtcacggagg ttccttggcc ccagacatc 49

<210> SEQ ID NO 64

<211> LENGTH: 49
<212> TYPE: DNA
<213> ORGANISM: Artificial
<220> FEATURE:
<223> OTHER INFORMATION: A primer

<400> SEQUENCE: 64
ttttctcgag ggaggacacg gtcaccaggg ttccttggcc ccagacatc 49

<210> SEQ ID NO 65
<211> LENGTH: 51
<212> TYPE: DNA
<213> ORGANISM: Artificial
<220> FEATURE:
<223> OTHER INFORMATION: A primer

<400> SEQUENCE: 65
gctgctgctg tggcttacag atgcaagatg tgacattgtg atgacccagt c 51

<210> SEQ ID NO 66
<211> LENGTH: 56
<212> TYPE: DNA
<213> ORGANISM: Artificial
<220> FEATURE:
<223> OTHER INFORMATION: A primer

<400> SEQUENCE: 66
tttgaattca tgtctgtgcc aactcaggtc ctggggttgc tgctgctgtg gcttac 56

<210> SEQ ID NO 67
<211> LENGTH: 28
<212> TYPE: DNA
<213> ORGANISM: Artificial
<220> FEATURE:
<223> OTHER INFORMATION: A primer

<400> SEQUENCE: 67
tttctcgagc cgttttattt ccagcttg 28

<210> SEQ ID NO 68
<211> LENGTH: 27
<212> TYPE: DNA
<213> ORGANISM: Artificial
<220> FEATURE:
<223> OTHER INFORMATION: A primer

<400> SEQUENCE: 68
tttttacata tgatagcgct taccctg 27

<210> SEQ ID NO 69
<211> LENGTH: 38
<212> TYPE: DNA
<213> ORGANISM: Artificial
<220> FEATURE:
<223> OTHER INFORMATION: A primer

<400> SEQUENCE: 69
tttagatcta cgaagaagaa gagcacgcgg atcataat 38

<210> SEQ ID NO 70
<211> LENGTH: 45
<212> TYPE: DNA
<213> ORGANISM: Artificial
<220> FEATURE:
<223> OTHER INFORMATION: A primer

<400> SEQUENCE: 70

-continued agcacgcgga tcataataag gaaggctacc accaccacca gaacc 45

<210> SEQ ID NO 71
<211> LENGTH: 35
<212> TYPE: DNA
<213> ORGANISM: Artificial
<220> FEATURE:
<223> OTHER INFORMATION: A primer

<400> SEQUENCE: 71
tttagatcta cgcaacacac aatccctagt atcac 35

<210> SEQ ID NO 72
<211> LENGTH: 47
<212> TYPE: DNA
<213> ORGANISM: Artificial
<220> FEATURE:
<223> OTHER INFORMATION: A primer

<400> SEQUENCE: 72
caatccctag tatcacacgg cgtatggcta ccaccaccac cagaacc 47

<210> SEQ ID NO 73
<211> LENGTH: 38
<212> TYPE: DNA
<213> ORGANISM: Artificial
<220> FEATURE:
<223> OTHER INFORMATION: A primer

<400> SEQUENCE: 73
tttagatcta cgcaacacac acaaccgcga atcacacg 38

<210> SEQ ID NO 74
<211> LENGTH: 46
<212> TYPE: DNA
<213> ORGANISM: Artificial
<220> FEATURE:
<223> OTHER INFORMATION: A primer

<400> SEQUENCE: 74
acaaccgcga atcacacgca ggcgcgctac caccaccacc agaacc 46

<210> SEQ ID NO 75
<211> LENGTH: 35
<212> TYPE: DNA
<213> ORGANISM: Artificial
<220> FEATURE:
<223> OTHER INFORMATION: A primer

<400> SEQUENCE: 75
tttagatctc cgcatcacca gggctcgagg gctgg 35

<210> SEQ ID NO 76
<211> LENGTH: 48
<212> TYPE: DNA
<213> ORGANISM: Artificial
<220> FEATURE:
<223> OTHER INFORMATION: A primer

<400> SEQUENCE: 76
cagggctcga gggctggcgt ggggcaggct accaccacca ccagaacc 48

<210> SEQ ID NO 77
<211> LENGTH: 52
<212> TYPE: DNA
<213> ORGANISM: Artificial
<220> FEATURE:

<223> OTHER INFORMATION: A primer

<400> SEQUENCE: 77
gctaccacca ccaccagaac caccaccacc ggatccgcgc ggaggggggg ct 52

<210> SEQ ID NO 78
<211> LENGTH: 58
<212> TYPE: DNA
<213> ORGANISM: Artificial
<220> FEATURE:
<223> OTHER INFORMATION: A primer

<400> SEQUENCE: 78
tttagatctg gtggcggagg ctcacttcct tattatgatc cccgtgctct tcttcttc 58

<210> SEQ ID NO 79
<211> LENGTH: 57
<212> TYPE: DNA
<213> ORGANISM: Artificial
<220> FEATURE:
<223> OTHER INFORMATION: A primer

<400> SEQUENCE: 79
ccgtgctctt cttcttcgtg gaggaggtgg ttcccttcca tattacgacc ctcgtgc 57

<210> SEQ ID NO 80
<211> LENGTH: 56
<212> TYPE: DNA
<213> ORGANISM: Artificial
<220> FEATURE:
<223> OTHER INFORMATION: A primer

<400> SEQUENCE: 80
tacgaccctc gtgcacttct gcttcgcgga tccgtcgacg gtggtggagg ttcagg 56

<210> SEQ ID NO 81
<211> LENGTH: 59
<212> TYPE: DNA
<213> ORGANISM: Artificial
<220> FEATURE:
<223> OTHER INFORMATION: A primer

<400> SEQUENCE: 81
tttagatctg gtggcggagg ctcccataca ccgtgtgata ctagggattg tgtgttgcg 59

<210> SEQ ID NO 82
<211> LENGTH: 58
<212> TYPE: DNA
<213> ORGANISM: Artificial
<220> FEATURE:
<223> OTHER INFORMATION: A primer

<400> SEQUENCE: 82
gggattgtgt gttgcgtgga ggaggtggtt ctcatacgcc ctgcgatact agagattg 58

<210> SEQ ID NO 83
<211> LENGTH: 58
<212> TYPE: DNA
<213> ORGANISM: Artificial
<220> FEATURE:
<223> OTHER INFORMATION: A primer

<400> SEQUENCE: 83
cctgcgatac tagagattgc gtcttgcggg gatccgtcga cggtggtgga ggttcagg 58

<210> SEQ ID NO 84

<211> LENGTH: 58
<212> TYPE: DNA
<213> ORGANISM: Artificial
<220> FEATURE:
<223> OTHER INFORMATION: A primer

<400> SEQUENCE: 84
tttagatctg gtggaggagg atcagcacct gcatgtgatt cgcggttgtg tgtgttgc 58

<210> SEQ ID NO 85
<211> LENGTH: 57
<212> TYPE: DNA
<213> ORGANISM: Artificial
<220> FEATURE:
<223> OTHER INFORMATION: A primer

<400> SEQUENCE: 85
cggttgtgtg tgttgcgtgg aggaggtggt tcagccccag cctgtgactc ccgcttg 57

<210> SEQ ID NO 86
<211> LENGTH: 56
<212> TYPE: DNA
<213> ORGANISM: Artificial
<220> FEATURE:
<223> OTHER INFORMATION: A primer

<400> SEQUENCE: 86
tgtgactccc gcttgtgtgt cctccgagga tccgtcgacg gtggtggagg ttcagg 56

<210> SEQ ID NO 87
<211> LENGTH: 57
<212> TYPE: DNA
<213> ORGANISM: Artificial
<220> FEATURE:
<223> OTHER INFORMATION: A primer

<400> SEQUENCE: 87
tttagatctg gtggaggagg ctcactgccc cacgccagcc ctcgagccct ggtgatg 57

<210> SEQ ID NO 88
<211> LENGTH: 57
<212> TYPE: DNA
<213> ORGANISM: Artificial
<220> FEATURE:
<223> OTHER INFORMATION: A primer

<400> SEQUENCE: 88
ctcgagccct ggtgatgcgg ggaggaggtg gttccttgcc ccacgccagc cctcggg 57

<210> SEQ ID NO 89
<211> LENGTH: 53
<212> TYPE: DNA
<213> ORGANISM: Artificial
<220> FEATURE:
<223> OTHER INFORMATION: A primer

<400> SEQUENCE: 89
cacgccagcc ctcgggccct ggtgatgcgg ggatccggtg gtggaggttc agg 53

<210> SEQ ID NO 90
<211> LENGTH: 25
<212> TYPE: DNA
<213> ORGANISM: Artificial
<220> FEATURE:
<223> OTHER INFORMATION: A primer

<400> SEQUENCE: 90

-continued ttgaattctt aaacaacagt agttt 25

<210> SEQ ID NO 91
<211> LENGTH: 24
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (7)..(7)
<223> OTHER INFORMATION: n is g, or t
<220> FEATURE:
<221> NAME/KEY: misc_feature
<222> LOCATION: (10)..(10)
<223> OTHER INFORMATION: n is c, or t
<220> FEATURE:
<221> NAME/KEY: misc_feature
<222> LOCATION: (22)..(22)
<223> OTHER INFORMATION: n is c, or g

<400> SEQUENCE: 91
ccgtttnatn tccagcttgg tncc 24

<210> SEQ ID NO 92
<211> LENGTH: 25
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (10)..(10)
<223> OTHER INFORMATION: n is g, or t
<220> FEATURE:
<221> NAME/KEY: misc_feature
<222> LOCATION: (14)..(14)
<223> OTHER INFORMATION: n is c, g, or t
<220> FEATURE:
<221> NAME/KEY: misc_feature
<222> LOCATION: (20)..(20)
<223> OTHER INFORMATION: n is a, or g

<400> SEQUENCE: 92
cggtgaccgn ggtnccttgn cccca 25

<210> SEQ ID NO 93
<211> LENGTH: 25
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (5)..(5)
<223> OTHER INFORMATION: n is a, or g
<220> FEATURE:
<221> NAME/KEY: misc_feature
<222> LOCATION: (11)..(11)
<223> OTHER INFORMATION: n is c, or g
<220> FEATURE:
<221> NAME/KEY: misc_feature
<222> LOCATION: (13)..(14)
<223> OTHER INFORMATION: n is g, or t
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (16)..(16)
<223> OTHER INFORMATION: n is a, or g
<220> FEATURE:
<221> NAME/KEY: misc_feature
<222> LOCATION: (22)..(22)

<223> OTHER INFORMATION: n is a, or c

<400> SEQUENCE: 93
atggnatgga ncnnnntctt tntct 25

<210> SEQ ID NO 94
<211> LENGTH: 29
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (9)..(9)
<223> OTHER INFORMATION: n is a, or t
<220> FEATURE:
<221> NAME/KEY: misc_feature
<222> LOCATION: (12)..(12)
<223> OTHER INFORMATION: n is a, or g
<220> FEATURE:
<221> NAME/KEY: misc_feature
<222> LOCATION: (22)..(22)
<223> OTHER INFORMATION: n is a, or t

<400> SEQUENCE: 94
atggatttnc angtgcagat tntcagctt 29

<210> SEQ ID NO 95
<211> LENGTH: 26
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (4)..(4)
<223> OTHER INFORMATION: n is a, or g
<220> FEATURE:
<221> NAME/KEY: misc_feature
<222> LOCATION: (9)..(9)
<223> OTHER INFORMATION: n is c, or g
<220> FEATURE:
<221> NAME/KEY: misc_feature
<222> LOCATION: (11)..(11)
<223> OTHER INFORMATION: n is c, or g
<220> FEATURE:
<221> NAME/KEY: misc_feature
<222> LOCATION: (18)..(18)
<223> OTHER INFORMATION: n is c, or t
<220> FEATURE:
<221> NAME/KEY: misc_feature
<222> LOCATION: (19)..(19)
<223> OTHER INFORMATION: n is a, or t
<220> FEATURE:
<221> NAME/KEY: misc_feature
<222> LOCATION: (21)..(21)
<223> OTHER INFORMATION: n is c, or t

<400> SEQUENCE: 95
atgnaatgna nctgggtnnt nctctt 26

<210> SEQ ID NO 96
<211> LENGTH: 31
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (7)..(7)
<223> OTHER INFORMATION: n is a, or t
<220> FEATURE:
<221> NAME/KEY: misc_feature
<222> LOCATION: (16)..(16)

-continued

```
<223> OTHER INFORMATION: n is a, or g
<220> FEATURE:
<221> NAME/KEY: misc_feature
<222> LOCATION: (24)..(24)
<223> OTHER INFORMATION: n is g, or t
<220> FEATURE:
<221> NAME/KEY: misc_feature
<222> LOCATION: (25)..(25)
<223> OTHER INFORMATION: n is a, or t
<220> FEATURE:
<221> NAME/KEY: misc_feature
<222> LOCATION: (26)..(27)
<223> OTHER INFORMATION: n is c, or t
<220> FEATURE:
<221> NAME/KEY: misc_feature
<222> LOCATION: (29)..(29)
<223> OTHER INFORMATION: n is a, or t

<400> SEQUENCE: 96

atgggcntca agatgnagtc acannnncng g                                    31
```